(12) United States Patent
Kacian et al.

(10) Patent No.: US 9,347,098 B2
(45) Date of Patent: *May 24, 2016

(54) REACTION MIXTURES FOR QUANTITATIVE AMPLIFICATION AND DETECTION OVER A WIDE DYNAMIC RANGE

(71) Applicant: Gen-Probe Incorporated, San Diego, CA (US)

(72) Inventors: Daniel L. Kacian, San Diego, CA (US); Kenneth A. Browne, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/562,922

(22) Filed: Dec. 8, 2014

(65) Prior Publication Data

US 2015/0093753 A1    Apr. 2, 2015

Related U.S. Application Data

(63) Continuation of application No. 14/064,427, filed on Oct. 28, 2013, now Pat. No. 8,932,817, which is a continuation of application No. 12/840,971, filed on Jul. 21, 2010, now Pat. No. 8,628,924.

(60) Provisional application No. 61/227,339, filed on Jul. 21, 2009, provisional application No. 61/230,938, filed on Aug. 3, 2009.

(51) Int. Cl.
*C12P 19/34* (2006.01)
*C12Q 1/68* (2006.01)

(52) U.S. Cl.
CPC ............ *C12Q 1/6865* (2013.01); *C12Q 1/6813* (2013.01); *C12Q 1/6851* (2013.01)

(58) Field of Classification Search
USPC ................................................. 435/6.12, 91.2
See application file for complete search history.

(56) References Cited

U.S. PATENT DOCUMENTS 4,486,530 A    12/1984  David et al.
4,514,505 A    4/1985   Canfield et al.
(Continued)

FOREIGN PATENT DOCUMENTS

EP    0595369 A1    5/1994
EP    1 045 036 A2  10/2000
(Continued)

OTHER PUBLICATIONS

J.K. Actor et al., "A flexible bioluminescent-quantitative polymerase chain reaction assay for analysis of competitive PCR amplicons," J. Clin. Lab. Anal. 13:40-47 (1999).

(Continued)

*Primary Examiner* — Kenneth Horlick
(74) *Attorney, Agent, or Firm* — Brian S. Sun; Nicholas V. Sherbina

(57) ABSTRACT

Disclosed are compositions and methods for making differentiable amplicon species at unequal ratios using a single amplification system in a single vessel. The number of differentiable amplicons and their ratios to one another are chosen to span the required linear dynamic range for the amplification reaction and to accommodate limitations of the measuring system used to determine the amount of amplicon generated. Unequal amounts of distinguishable amplicon species are generated by providing unequal amounts of one or more amplification reaction components (e.g., distinguishable amplification oligomers, natural and unnatural NTP in an NTP mix, or the like). The amount of target nucleic acid present in a test sample is determined using the linear detection range generated from detection of one or more amplicon species having an amount within the dynamic range of detection.

8 Claims, 13 Drawing Sheets

(56) References Cited

U.S. PATENT DOCUMENTS

| | | |
|---|---|---|
| 4,595,661 A | 6/1986 | Cragle et al. |
| 4,683,195 A | 7/1987 | Mullis et al. |
| 4,683,202 A | 7/1987 | Mullis |
| 4,745,181 A | 5/1988 | Law et al. |
| 4,766,062 A | 8/1988 | Diamond et al. |
| 4,851,330 A | 7/1989 | Kohne |
| 4,965,188 A | 10/1990 | Mullis et al. |
| 5,004,565 A | 4/1991 | Schaap |
| 5,130,238 A | 7/1992 | Malek et al. |
| 5,200,314 A | 4/1993 | Urdea |
| 5,219,727 A | 6/1993 | Wang et al. |
| 5,283,174 A | 2/1994 | Arnold, Jr. et al. |
| 5,310,652 A | 5/1994 | Gelfand et al. |
| 5,312,921 A | 5/1994 | Glazer et al. |
| 5,322,770 A | 6/1994 | Gelfand |
| 5,395,752 A | 3/1995 | Law et al. |
| 5,399,491 A | 3/1995 | Kacian et al. |
| 5,422,252 A | 6/1995 | Walker et al. |
| 5,427,930 A | 6/1995 | Birkeymeyer et al. |
| 5,447,687 A | 9/1995 | Lewis et al. |
| 5,512,445 A | 4/1996 | Yang |
| 5,516,663 A | 5/1996 | Backman et al. |
| 5,547,861 A | 8/1996 | Nadeau et al. |
| 5,648,211 A | 7/1997 | Fraiser et al. |
| 5,652,345 A | 7/1997 | Schaap et al. |
| 5,702,887 A | 12/1997 | Law et al. |
| 5,705,365 A | 1/1998 | Ryder et al. |
| 5,710,029 A | 1/1998 | Ryder et al. |
| 5,739,042 A | 4/1998 | Frengen |
| 5,741,650 A | 4/1998 | Lapidus et al. |
| 5,756,709 A | 5/1998 | Nelson et al. |
| 5,814,447 A | 9/1998 | Ishiguro et al. |
| 5,824,518 A | 10/1998 | Kacian et al. |
| 5,858,732 A | 1/1999 | Solomon et al. |
| 5,925,517 A | 7/1999 | Tyagi et al. |
| 6,037,130 A | 3/2000 | Tyagi |
| 6,040,138 A | 3/2000 | Lockhart et al. |
| 6,040,166 A | 3/2000 | Erlich et al. |
| 6,063,572 A | 5/2000 | Ishiguro et al. |
| 6,066,458 A | 5/2000 | Haaland et al. |
| 6,143,496 A | 11/2000 | Brown et al. |
| 6,156,501 A | 12/2000 | McGall et al. |
| 6,165,800 A | 12/2000 | Jiang et al. |
| 6,174,670 B1 | 1/2001 | Wittwer et al. |
| 6,177,555 B1 | 1/2001 | Jayasena |
| 6,180,340 B1 | 1/2001 | Nelson et al. |
| 6,197,563 B1 | 3/2001 | Erlich et al. |
| 6,238,869 B1 | 5/2001 | Kris et al. |
| 6,238,927 B1 | 5/2001 | Abrams et al. |
| 6,245,511 B1 | 6/2001 | Gulati |
| 6,245,517 B1 | 6/2001 | Chen |
| 6,261,783 B1 | 7/2001 | Jayasena |
| 6,268,146 B1 | 7/2001 | Shultz et al. |
| 6,294,338 B1 | 9/2001 | Nunomura |
| 6,350,579 B1 | 2/2002 | Nelson et al. |
| 6,355,421 B1 | 3/2002 | Coull et al. |
| 6,361,945 B1 | 3/2002 | Becker et al. |
| 6,514,736 B1 | 2/2003 | Erlich et al. |
| 6,541,205 B1 | 4/2003 | Yokoyama et al. |
| 6,569,627 B2 | 5/2003 | Wittwer et al. |
| 7,169,554 B2 | 1/2007 | Rutter et al. |
| 7,374,885 B2 | 5/2008 | Becker et al. |
| 7,556,923 B1 | 7/2009 | Hedgpeth et al. |
| 2001/0000148 A1 | 4/2001 | Kurane |
| 2002/0001800 A1 | 1/2002 | Lapidus |
| 2002/0058262 A1 | 5/2002 | Sagner |
| 2002/0106653 A1 | 8/2002 | Kurane |
| 2003/0105320 A1 | 6/2003 | Becker et al. |
| 2004/0029111 A1 | 2/2004 | Linnen et al. |
| 2004/0053254 A1 | 3/2004 | Wangh et al. |
| 2004/0121364 A1 | 6/2004 | Chee et al. |
| 2005/0009048 A1 | 1/2005 | Sagner |
| 2005/0064451 A1 | 3/2005 | Happe et al. |
| 2006/0024714 A1 | 2/2006 | Lao et al. |
| 2006/0057611 A1 | 3/2006 | Kao et al. |
| 2006/0088874 A1 | 4/2006 | Bacher et al. |
| 2006/0246475 A1 | 11/2006 | Peterson et al. |
| 2007/0166759 A1 | 7/2007 | Weeks et al. |
| 2008/0131875 A1 | 6/2008 | Hall et al. |
| 2008/0131892 A1 | 6/2008 | Becker et al. |
| 2009/0181389 A1 | 7/2009 | Li et al. |

FOREIGN PATENT DOCUMENTS

| | | |
|---|---|---|
| WO | 95/03430 A1 | 2/1995 |
| WO | 96/17958 A1 | 6/1996 |
| WO | 97/10365 A1 | 3/1997 |
| WO | 98/31836 A1 | 7/1998 |
| WO | 98/56954 A1 | 12/1998 |
| WO | 98/58083 A2 | 12/1998 |
| WO | 99/22018 A2 | 5/1999 |
| WO | 99/23256 A1 | 5/1999 |
| WO | 99/31276 A1 | 6/1999 |
| WO | 99/49293 A2 | 9/1999 |
| WO | 99/55912 A1 | 11/1999 |
| WO | 99/58640 A2 | 11/1999 |
| WO | 00/34521 A1 | 6/2000 |
| WO | 00/43552 A2 | 7/2000 |
| WO | 00/60126 A2 | 10/2000 |
| WO | 00/70329 A1 | 11/2000 |
| WO | 00/75378 A1 | 12/2000 |
| WO | 01/31055 A2 | 5/2001 |
| WO | 01/31062 A1 | 5/2001 |
| WO | 01/94625 A2 | 12/2001 |
| WO | 03/020952 A2 | 3/2003 |
| WO | 03/048377 A2 | 6/2003 |
| WO | 03/048377 A3 | 6/2003 |
| WO | 2006034215 A2 | 3/2006 |
| WO | 2006/079049 A2 | 7/2006 |
| WO | 2006/079049 A3 | 7/2006 |
| WO | 2006/085964 A2 | 8/2006 |
| WO | 2006/085964 A3 | 8/2006 |
| WO | 2007095923 A1 | 8/2007 |

OTHER PUBLICATIONS

I.A. Afonina et al., "Minor groove binder-conjugated DNA probes for quantitative DNA detection by hybridization-triggered fluorescence," BioTechniques 32:940-949 (2002).

S.K. Arya et al., "Homology of genome of AIDS-associated virus with genomes of human T-cell leukemia viruses," Science 225:927-930 (1984).

K. Borchers et al., "A nested PCR for the detection and differentiation of EHV-1 and EHV-4," J. Virol. Methods 45:331-336 (1993).

Morris et al., "Comparision of Transcription-Mediated Amplification and Growth-Based Methods for the Quantitation of Enterococcus Bacteria in Environmental Waters," Appl. Environ. Microbiol., May 2008, pp. 3319-3320, vol. 74(10), American Society for Microbiology, Washington, D.C.

Munoz-Jordon et al., "Highly Sensitive Detection of Dengue Virus Nucleic Acid in Samples from Clinically Ill Patients," J. Clin. Microbiol., Apr. 2009, pp. 927-931, vol. 47(4), American Society for Microbiology, Washington, D.C.

Invitation to Pay Additional Fees for PCT/US2010/042776 dated Dec. 27, 2010.

International Search Report and Written Opinion for PCT/US2010/042776 dated Feb. 24, 2011.

International Preliminary Report on Patentability for PCT/US2010/042776 dated Feb. 2, 2012.

Milligan et al., "Oligoribonucleotide synthesis using T7 RNA polymerase and synthetic DNA templates," Nucleic Acids Res., 1987, 15(21):8783-8798, Oxford University Press, Oxford, United Kingdom.

Baklanov et al., "Effect on DNA transcription of nucleotide sequences upstream to T7 promoter," Nucleic Acids Res., 1996, 24(18):3659-3660, Oxford University Press, Oxford, United Kingdom.

Bandwar et al., "Kinetic and thermodynamic basis of promoter strength: multiple steps of transcription initiation by T7 RNA polymerase are modulated by the promoter sequence," Biochemistry, 2002, 41(11):3586-3595, American Chemical Society, Washington D.C., USA.

(56) References Cited

OTHER PUBLICATIONS

Tang et al., "Extended upstream A-T sequence increases T7 promoter strength," J. Biol. Chem., 2005, 280 (49):40707-40713, American Society for Biochemistry and Molecular Biology, Baltimore, USA.
Gaal et al., "Transcription Regulation by Initiating NTP Concentration: rRNA Synthesis in Bacteria," Science, 1997, 278:2092-2097, American Association for the Advancement of Science, Washington D.C., USA.
Guajardo et al., "NTP concentration effects on initial transcription by T7 RNAP indicate that translocation occurs through passive sliding and reveal that divergent promoters have distinct NTP concentration requirements for productive initiation," J. Mol. Biol., 1996, 281:777-792, Elsevier Science, Amsterdam, Netherlands.
Schena et al., "Parallel human genome analysis: Microarray-based expression monitoring of 1000 genes," Proc. Natl. Acad. Sci. USA, 1996, 93:10614-10619, National Academy of Sciences, Washington D.C., USA.
White et al., "Chemiluminescence Involving Acidic and Ambident Ion Light Emitters. The Chemiluminescence of the 9-Acridinepercarboxylate Anion," J. Am. Chem. Soc., 1987, 109:5189-5196, American Chemical Society, Washington D.C., USa.
Brown et al., "Development and application of a novel acridinium ester for use as a chemiluminescent emitter in nucleic acid hybridization assays using chemiluminescence quenching," Org. Biomol. Chem., 2009, 7(2):386-394, Royal Society of Chemistry, Cambridge, United Kingdom.
Nelson et al., "Homogeneous and Heterogeneous Chemiluminescent DNA Probe-Based Assay Formats for the Rapid and Sensitive Detection of Target Nucleic Acids," Luminescence Immunology and Molecular Applications, 1990, 293-309, CRC Press, Boca Raton, USA.
Nelson et al., "Detection of Acridinium Esters by Chemiluminescence," Nonisotopic Probing, Blotting, and Sequencing, 1995, 391-428, Academic Press, San Diego, USa.
Nelson et al., "Detection of all single-base mismatches in solution by chemiluminescence," Nucleic Acids Res., 1996, 24:4998-5003, Oxford University Press, Oxford, United Kingdom.
Nelson et al., "Simultaneous Detection of Multiple Nucleic Acid Targets in a Homogeneous Format," Biochemistry, 1996, 35:8429-8438, American Chemical Society, Washington D.C., USA.
Kessler et al., "Nonradioactive Analysis of Biomolecules," 2nd ed., 2000, 74-80, Springer-Verlag, New York, USA.
Becker et al., "The Double Helix Is Dehydrated: Evidence from the Hydrolysis of Acridinium Ester-Labeled Probes," Biochemistry, 1999, 38:5603-5611, American Chemical Society, Washington D.C., USA.
Shinkai et al., "Chemiluminescence of 9-Methyleneacridans in Micellar and Membranous Systems," Chem. Lett., 1981, 1523-1526, The Chemical Society of Japan, Tokyo, Japan.
Beck et al., "Applications of dioxetane chemiluminescent probes to molecular biology," Anal. Chem., 1990, 62:2258-2270, American Chemical Society, Washington D.C., USA.
Grayeski et al., "Chemiluminescence Energy Transfer Processes and Micellar Effects," Langmuir, 1997, 13:2675-2680, American Chemical Society, Washington D.C., USA.
Patel et al., "Homogeneous immunoassay based on chemiluminescence energy transfer," Clin. Chem., 1983, 29:1604-1608, American Association for Clinical Chemistry, Washington D.C., USA.
Persson et al., "Four-color multiplex reverse transcription polymerase chain reaction—overcoming its limitations," Anal. Biochem., 2005, 344:33-42, Elsevier Science, Amsterdam, Netherlands.
Wolf et al., "Viral Multiplex Quantitative PCR Assays for Tracking Sources of Fecal Contamination," Appl. Environ. Microbiol., 2010, 76(5):1388-1394, American Society for Microbiology, Washington D.C., USA.
Brittain-Long et al., "Prospective evaluation of a novel multiplex real-time PCR assay for detection of fifteen respiratory pathogens—Duration of symptoms significantly affects detection rate," J. Clin. Virol., 2010, 47:263-267, Elsevier Science, Amsterdam, Netherlands.
Tyagi et al., "Wavelength-shifting molecular beacons," Nat. Biotechnol., 2000, 18(11):1191-1196, Nature America Publishing, New York, USA.
Akitaya et al., "NTP concentration switches transcriptional activity by changing the large-scale structure of DNA," Biomacromolecules, 2003, 4(5):1121-1125, American Chemical Society, Washington D.C., USA.
Silverstein et al., "Spectrometric Identification of Organic Compounds," 4th ed., 1981, ch. 6, pp. 305-331, John Wiley & Sons, New York.
Schaap et al., "Chemical and Enzymatic Triggering of 1,2-Dioxetanes. 2: Fluoride-Induced Chemiluminescence from Tert-Butyldimethylsilyloxy-Substituted Dioxetanes," Tetrahedron Lett., 1987, 28:1155-1158, Elsevier Science, Oxford, United Kingdom.
Bagazgoitia et al., "Effect of Surfactants on the Intensity of Chemiluminescence Emission from Acridinium Ester Labelled Proteins," J. Biolum. Chemilum., 1988, 2:121-128, John Wiley and Sons Ltd., Sussex, England, United Kingdom.
M. Zazzi et al., "Simultaneous amplification of multiple HIV-1 DNA sequences from clinical specimens by using nested-primer polymerase chain reaction," AIDS Res. Human Retrovir. 9:315-320 (1993).
M. Zazzi et al., "Optimal conditions for detection of human immunodeficiency virus type 1 DNA by polymerase chain reaction with nested primers," Mol. Cell. Probes 7:431-437 (1993).
X.Y. Zhang et al., "Detection and quantitation of low numbers of chromosomes containing bcl-2 oncogene translocations using semi-nested PCR," BioTechniques 16:502-507 (1994).
Z. Zhu et al., "Molecular mechanism controlling the incorporation of fluorescent nucleotides into DNA by PCR," Cytometry 28:206-211 (1997).
Non-Final Rejection, U.S. Appl. No. 12/840,971, mailed Mar. 25, 2013.
Notice of Allowance, U.S. Appl. No. 12/840,971, mailed Sep. 6, 2013.
Patent Examination Report No. 1, Australian Patent Application No. 2010276236, issued Feb. 15, 2013.
Patent Examination Report No. 2, Australian Patent Application No. 2010276236, issued Dec. 20, 2013.
Communication pursuant to Article 94(3) EPC, European Application No. 10735168.6, dated Jan. 30, 2013.
Notice of Reasons for Rejection, Japanese Patent Application No. 2012-521757, mailed Oct. 1, 2013.
Igaku to Yakugaku, Medicine and Pharmaceutical Sciences, vol. 46, p. 413-419 (2001).
Hashimoto et al., "Rapid Identification of Mycobacteria by Combined Method of Polymerase Chain Reaction and the Gen-Probe DNA Hybridization System," Kekkaku: [Tuberculosis], Aug. 31, 1994, pp. 25-30, vol. 69, No. 12.
Dhingra et al., "Hybridization Protection Assay: A Rapid, Sensitive, and Specific Method for Detection of Philadelphia Chromosome-Positive Leukemias", Blood, Jan. 15, 1991, pp. 238-242, vol. 77, No. 2.
A.P. Drabovich et al., "Smart aptamers facilitate multi-probe affinity analysis of proteins with ultra-wide dynamic range of measured concentrations," J. Am. Chem. Soc. 129:7260-7261 (2007).
J.R. Dyer et al., "Comparison of NucliSens and Roche Monitor assays for quantitation of levels of human immunodeficiency virus type 1 RNA in plasma," J. Clin. Microbiol. 37:447-449 (1999).
X. Fang et al., "Designing a novel molecular beacon for surface-immobilized DNA hybridization studies," J. Am. Chem. Soc. 121:2921-2922 (1999).
O. Grankvist et al., "Nested PCR assays with novel primers yield greater sensitivity to Tanzanian HIV-1 samples than a commercial PCR detection kit," J. Virol. Methods 62:131-141 (1996).
L.A. Haff, "Improved quantitative PCR using nested primers," PCR Methods Appl. 3:332-337 (1994).
Q. He et al., "Primers are decisive for sensitivity of PCR," BioTechniques 17:82-86 (1994).

(56) References Cited

OTHER PUBLICATIONS

T. Jalava et al., "Quantification of hepatitis B virus DNA by competitive amplification and hybridization on microplates," BioTechniques 15:134-139 (1993).

K.K. Jensen et al., "Kinetics for hybridization of peptide nucleic acids (PNA) with DNA and RNA studied with the BIAcore technique," Biochemistry 36:5072-5077 (1997).

A.A. Killeen et al., "Linked linear amplification for simultaneous analysis of the two most common hemochromatosis mutations," Clin. Chem. 49:1050-1057 (2003).

R. Knutsson et al., "Modeling of 5' nuclease real-time responses for optimization of a high-throughput enrichment PCR procedure for *Salmonella enterica*," J. Clin. Microbiol. 40:52-60 (2002).

G. Leone et al., "Molecular beacon probes combined with amplification by NASBA enable homogeneous, real-time detection of RNA," Nucleic Acids Res. 26:2150-2155 (1998).

W. Liu et al., "Validation of a quantitative method for real time PCR kinetics," Biochem. Biophys. Res. Comm. 294:347-353 (2000).

X. Liu et al., "Molecular beacons for DNA biosensors with micrometer to submicrometer dimensions," Anal. Biochem. 283:56-63 (2000).

K.J. Livak, "Allelic discrimination using fluorogenic probes and the 5' nuclease assay," Gen. Analysis: Biomol. Eng'g 14:143-149 (1999).

V. Lyamichev et al., "Polymorphism identification and quantitative detection of genomic DNA by invasive cleavage of oligonucleotide probes," Nature Biotechnol. 17:292-296 (1999).

M. Majlessi et al., "Advantages of 2'-O-methyl oligoribonucleotide probes for detecting RNA targets," Nucleic Acids Res. 26:2224-2229 (1998).

R.A. McPherson, "Evolution of polymerase chain reaction to a quantitative laboratory tool," Clin. Chem. 41:1065-1067 (1995).

H. Millward et al., "Homogeneous amplification and mutation scanning of the p53 gene using fluorescent melting curves," Clin. Chem. 48:1321-1328 (2002).

F. Miura et al., "A novel strategy to design highly specific PCR primers based on the stability and uniqueness of 3'- end subsequences," Bioinformatics 21:4363-4370 (2005).

C. Morrison et al., "The impact of the PCR plateau phase on quantitative PCR," Biochim. Biophys. Acta 1219:493-498 (1994).

M.J. Moser, "Exploiting the enzymatic recognition of an unnatural base pair to develop a universal genetic analysis system," Clin. Chem. 49:407-414 (2003).

J. Nurmi et al., "A new label technology for the detection of specific polymerase chain reaction products in a closed tube," Nucleic Acids Res. 28:e28 (2000).

N. Ohmura et al., "Combinational use of antibody affinities in an immunoassay for extension of dynamic range and detection of multiple analytes," Anal. Chem. 75:104-110 (2003).

M. Okamoto et al., "Detection of hepatitis C virus genome in human serum by multi-targeted polymerase chain reaction," J. Med. Virol. 41:6-10 (1993).

N. Okayama et al., "Evaluation of a new efficient procedure for single-nucleotide polymorphism genotyping: tetra-primer amplification refractory mutation system-polymerase chain reaction," Clin. Chem. Lab. Med. 42:13-16 (2004).

K.E. Pierce et al., "Detection of cystic fibrosis alleles from single cells using molecular beacons and a novel method of asymmetric real-time PCR," Mol. Human Reprod. 9:815-820 (2003).

K.E. Pierce et al., "Linear-after-the-exponential (LATE)-PCR: Primer design criteria for high yields of specific single-stranded DNA and improved real-time detection," Proc. Natl. Acad. Sci. USA 102:8609-8614 (2005).

K.E. Pierce et al., "Linear-after-the-exponential polymerase chain reaction and allied technologies," Methods in Molecular Medicine: Single Cell Diagnostics: Methods and Protocols 65-85 (Humana Press Inc., Totowa, NJ, 2007).

D.A. Rappolee et al., "Wound macrophages express TGF-α and other growth factors in vivo: Analysis by mRNA phenotyping," Science 241:708-712 (1988).

A.A. Reyes et al., "Linked linear amplification: A new method for the amplification of DNA," Clin. Chem. 47:31-40 (2001).

J.E. Rice et al., "Monoplex/multiplex linear-after-the-exponential-PCR assays combined with PrimeSafe and Dilute-'N'-Go sequencing," Nature Protocols 2:2429-2438 (2007).

J.J. Salk et al., "Direct amplification of single-stranded DNA for pyrosequencing using linear-after-the-exponential (LATE)-PCR," Anal. Biochem. 353:124-132 (2006).

J.A. Sanchez et al., "Linear-after-the-exponential (LATE)-PCR: An advanced method of asymmetric PCR and its uses in quantitative real-time analysis," Proc. Natl. Acad. Sci. USA 101:1933-1938 (2004).

J.A. Sanchez et al., "Two-temperature LATE-PCR endpoint genotyping," BMC Biotechnol. 6:44 (2006).

D.T. Scadden et al., "Quantitation of plasma human immunodeficiency virus type 1 RNA by competitive polymerase chain reaction," J. Infect. Dis. 165:1119-1123 (1992).

B. Schierwater et al., "The effects of nested primer binding sites on the reproducibility of PCR: mathematical modeling and computer simulation studies," J. Comp. Biol. 3:235-251 (1996).

B. Schweitzer et al., "Immunoassays with rolling circle DNA amplification: A versatile platform for ultrasensitive antigen detection," Proc. Natl. Acad. Sci. USA 97:10113-10119 (2000).

R. Sestini et al., "Measuring c-erbB-2 oncogene amplification in fresh and paraffin-embedded tumors by competitive polymerase chain reaction," Clin. Chem. 40:630-636 (1994).

R. Sestini et al., "Gene amplification for c-erbB-2, c-myc, epidermal growth factor receptor, int-2, and N-myc measured by quantitative PCR with a multiple competitor template," Clin. Chem. 41:826-832 (1995).

F.J. Steemers et al., "Screening unlabeled DNA targets with randomly ordered fiber-optic gene arrays," Nature Biotechnol. 18:91-94 (2000).

S. Tyagi et al., "Molecular beacons: Probes that fluoresce upon hybridization," Nature Biotechnol. 14:303-308 (1996).

Udaykumar et al., "Enhanced diagnostic efficiency of the polymerase chain reaction by co-amplification of multiple regions of HIV-I and HIV-2," J. Virol. Methods 49:37-46 (1994).

J.A.M. Vet et al., "Multiplex detection of four pathogenic retroviruses using molecular beacons," Proc. Natl. Acad. Sci. USA 96:6394-6399 (1999).

V.K. Viswanathan et al., "Template secondary structure promotes polymerase jumping during PCR amplification," BioTechniques 27:508-511 (1999).

A.M. Wang et al., "Quantitation of mRNA by the polymerase chain reaction," Proc. Natl. Acad. Sci. USA 86:9717-9721 (1989).

S.P. Yip et al., "Use of dual TaqMan probes to increase the sensitivity of 1-step quantitative reverse transcription-PCR: Application to the detection of SARS coronavirus," Clin. Chem. 51:1885-1888 (2005).

FIG. 1A – Amplification
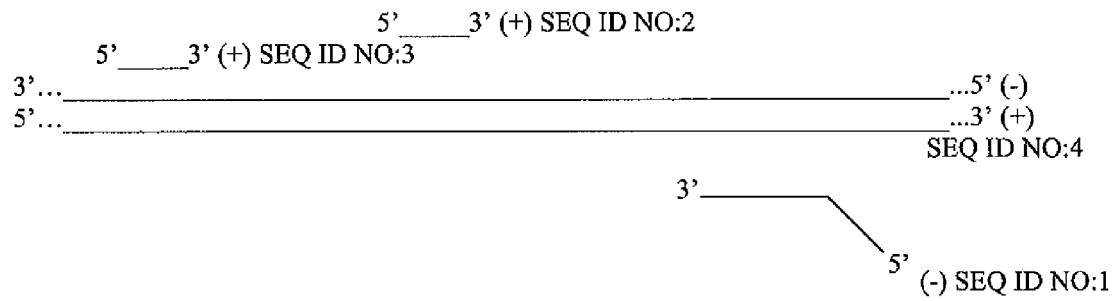
FIG. 1B – Distinguishable Amplicons
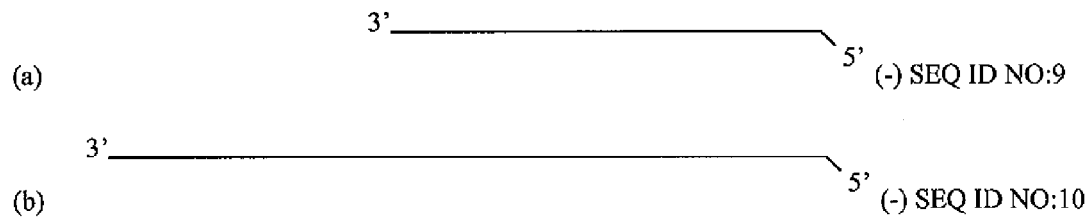
FIG. 1C – Detection
5'___3' (+) SEQ ID NO:5
or
5'___3' (+) SEQ ID NO:6
or
5'___3' (+) SEQ ID NO:5
5'___3' (+) SEQ ID NO:6

FIG. 4
FIG. 4A – Amplification
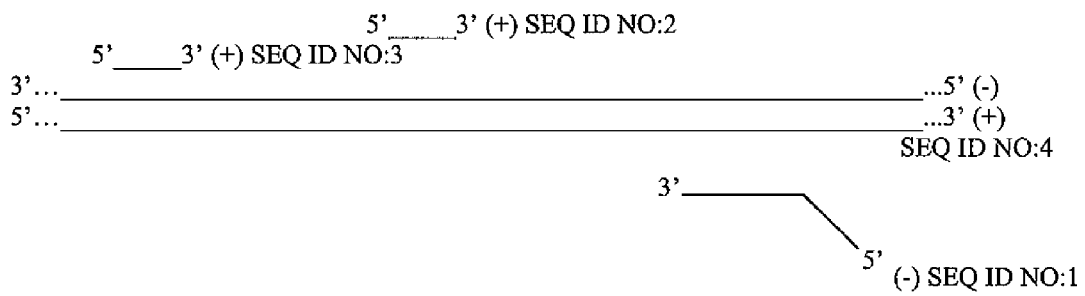
FIG. 4B – Distinguishable Amplicons
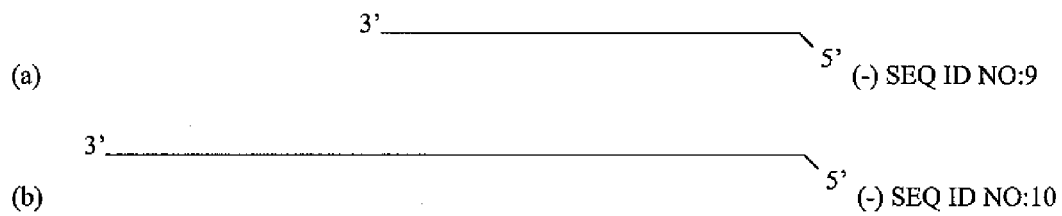
FIG. 4C – Detection
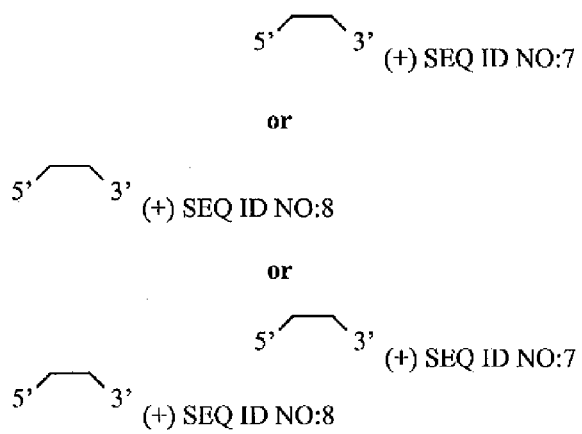

SEQUENCE LISTING

<160> NUMBER OF SEQ ID NOS: 10

<210> SEQ ID NO 1
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)
<223> OTHER INFORMATION: Promoter Sequence

<400> SEQUENCE: 1
aatttaatac gactcactat agggagagtt tgtatgtctg ttgctattat           50

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 2
acagcagtac aaatggcag                                             19

<210> SEQ ID NO 3
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 3
attccctaca atccccaaag tcaa                                       24

<210> SEQ ID NO 4
<211> LENGTH: 1016
<212> TYPE: RNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: nucleotides from cloning vector, including
      portions of the cloning vector's promoter sequence.

<400> SEQUENCE: 4
gggagacaag cuugcaugcc ugcaggucga cucuagagga uccccgggua ccagcacaca    60
aaggaauugg aggaaaugaa caaguagaua aauuagucag ugcuggaauc aggaaaauac   120
uauuuuuaga uggaauagau aaggcccaag augaacauga gaaauaucac aguaauugga   180
gagcaauggc uagugauuuu aaccugccac cuguaguagc aaaagaaaua guagccagcu   240
gugauaaaug ucagcuaaaa ggagaagcca ugcauggaca aguagacugu aguccaggaa   300
uauggcaacu agauuguaca cauuuagaag gaaaaguuau ccugguagca guucauguag   360
ccaguggaua uauagaagca gaaguuauuc cagcagaaac agggcaggaa acagcauauu   420
uucuuuuaaa auuagcagga agauggccag uaaaaacaau acauacagac aauggcagca   480
auuucaccag ugcuacgguu aaggccgccu guuggugggc gggaaucaag caggaauuug   540
gaauucccua caauccccaa agucaaggag uaguagaauc uaugaauaaa gaauuaaaga   600
aaauuauagg acagguaaga gaucaggcug aacaucuuaa gacagcagua caaauggcag   660
uauucaucca caauuuuaaa agaaaagggg gauuggggg guacagugca ggggaaagaa   720
uaguagacau aauagcaaca gacauacaaa cuaagaauu acaaaaacaa auucaaaaaa   780
uucaaaauuu ucggguuuau uacagggaca gcagaaaucc acuuuggaaa ggaccagcaa   840
agcuccucug gaaaggugaa ggggcaguag uaauacaaga uaauagugac auaaaaguag   900

```
ugccaagaag aaaagcaaag aucauuaggg auuauggaaa acagauggca ggugaugauu      960
guguggcaag uagacaggau gaggauuaga acauggaaaa guuuaguaaa acacca         1016

<210> SEQ ID NO 5
<211> LENGTH: 22
<212> TYPE: RNA
<213> ORGANISM: Artificial Sequence
<220> FEATURE:
<223> OTHER INFORMATION: Synthetic Oligomer

<400> SEQUENCE: 5
ccacaauuuu aaaagaaaag gg                                                22

<210> SEQ ID NO 6
<211> LENGTH: 22
<212> TYPE: RNA
<213> ORGANISM: Artificial Sequence
<220> FEATURE:
<223> OTHER INFORMATION: Synthetic Oligomer

<400> SEQUENCE: 6
agaaaauuau aggacaggua ag                                                22

<210> SEQ ID NO 7
<211> LENGTH: 32
<212> TYPE: RNA
<213> ORGANISM: Artificial Sequence
<220> FEATURE:
<223> OTHER INFORMATION: Synthetic Oligomer

<400> SEQUENCE: 7
cucguccaca auuuuaaaag aaaagggacg ag                                     32

<210> SEQ ID NO 8
<211> LENGTH: 32
<212> TYPE: RNA
<213> ORGANISM: Artificial Sequence
<220> FEATURE:
<223> OTHER INFORMATION: Synthetic Oligomer

<400> SEQUENCE: 8
ccucuagaaa auuauaggac agguaagaga gg                                     32

<210> SEQ ID NO 9
<211> LENGTH: 116
<212> TYPE: RNA
<213> ORGANISM: Artificial Sequence
<220> FEATURE:
<223> OTHER INFORMATION: Synthetic Oligomer

<400> SEQUENCE: 9
gggagaguuu guaugucugu ugcuauuaug ucuacuauuc uuucccugc acuguacccc        60 ccaauccccc cuuuucuuuu aaaauugugg augaauacug ccauuguac ugcugu          116

<210> SEQ ID NO 10
<211> LENGTH: 215
<212> TYPE: RNA
<213> ORGANISM: Artificial Sequence
<220> FEATURE:
<223> OTHER INFORMATION: Synthetic Oligomer

<400> SEQUENCE: 10
gggagaguuu guaugucugu ugcuauuaug ucuacuauuc uuucccugc acguacccc         60
```

```
ccaaucccccc  cuuuucuuuu  aaaauugugg  augaauacug  ccauuuguac  ugcugucuua      120
agauguucag  ccugaucucu  uaccuguccu  auaauuuucu  uuaauucuuu  auucauagau      180
ucuacuacuc  cuugacuuug  gggauuguag  ggaau                                    215
```

REACTION MIXTURES FOR QUANTITATIVE AMPLIFICATION AND DETECTION OVER A WIDE DYNAMIC RANGE

RELATED APPLICATIONS

This application is a continuation of U.S. application Ser. No. 14/064,427, filed Oct. 28, 2013, now issued as U.S. Pat. No. 8,932,817, which is a continuation of U.S. application Ser. No. 12/840,971, filed Jul. 21, 2010, now issued as U.S. Pat. No. 8,628,924, which claims priority to U.S. Provisional Application Nos. 61/227,339, filed Jul. 21, 2009, and 61/230,938, filed August 3, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII Copy, created on Oct. 16, 2013, is named GP238_03UT_SeqList_ST25.txt and is 4,100 bytes in size.

FIELD OF THE INVENTION

The present application relates to compositions and methods for amplifying and detecting a nucleic acid sequence that may be present in a test sample, more particularly, for amplifying and quantitatively detecting a nucleic acid sequence over a wide dynamic range for which the target nucleic acid sequence may be present in the sample.

BACKGROUND OF THE INVENTION

Methods that allow accurate detection and quantitation of nucleic acid sequences are invaluable tools for diagnosis and treatment of a wide range of diseases. For example, detection and quantitation of an infectious agent's nucleic acid sequence can provide diagnostic or prognostic information or allow a physician to monitor a patient's response to therapy. Further, accurate detection of low levels of viremia in infections such as human immunodeficiency virus (HIV) or hepatitis C virus helps to prevent spread of the virus, to estimate prognosis and response to therapy, and to detect the emergence of drug-resistant viruses in treated individuals. It is equally important to accurately measure high levels of viremia in untreated patients to establish initial infection levels.

Methods for amplifying a target nucleic acid sequence that may be present in a test sample are known and include methods such as the polymerase chain reaction (PCR; e.g., U.S. Pat. Nos. 4,683,195, 4,683,202, 4,965,188, 6,040,166, 6,197,563 and 6,514,736); reverse transcription polymerase chain reaction (RT-PCR; e.g., U.S. Pat. Nos. 5,310,652 and 5,322,770); transcription-mediated amplification (TMA; e.g., U.S. Pat. Nos. 5,399,491, 5,824,518 and 7,374,885); ligase chain reaction (LCR; e.g., U.S. Pat. Nos. 5,427,930 and 5,516,663); strand displacement amplification (SDA; e.g., U.S. Pat. Nos. 5,422,252, 5,547,861 and 5,648,211); rolling circle amplification (RCA; e.g., U.S. Pat. Nos. 5,648,245 and 5,854,033); helicase-dependent amplification (HDA; e.g., U.S. Pat. Nos. 7,282,328 and 7,662,594); and nucleic acid sequence based amplification (NASBA; e.g., U.S. Pat. No. 5,130,238).

Methods for detecting non-amplified or amplified target nucleic acid sequences that may be present in a test sample are also known. Some detection methods are "homogeneous" methods that do not require separation of a detection agent associated with the target nucleic acid from the detection agent that is not associated with the target nucleic acid. Such methods include use of intercalating dyes (e.g., U.S. Pat. Nos. 5,312,921, 5,814,447, 6,063,572, 6,541,205 and 6,569,627), a Hybridization Protection Assay (HPA; e.g., U.S. Pat. No. 5,283,174), and use of molecular beacon probes (e.g., U.S. Pat. No. 5,925,517) or molecular torch probes (e.g., U.S. Pat. No. 6,361,945). Other methods are "heterogeneous" and require physical separation of the detection agent associated with the target nucleic acid from the detection agent not associated with the target nucleic acid. One of the most common heterogeneous methods involves the capture of target nucleic acids onto a solid support, hybridization of a labeled detection probe, and washing under appropriately stringent conditions to remove non-specifically bound probe. The label (e.g, a radioisotope) that remains bound to the support is then measured.

While currently available amplification techniques may provide sufficient sensitivity for some applications, other diagnostic and therapeutic situations require more sensitivity than is available from these available methods. Furthermore, under certain circumstances, it is desirable to determine whether the nucleic acid sequence is present at a high or low concentration level. Thus, there is a need for methods through which target nucleic acids in a test sample can be detected and quantified accurately over a relatively large dynamic range in a single experiment.

Nucleic acid analytes of interest from a specimen may be present at concentrations that are less than can be detected by routine methods. This problem is often circumvented by implementing one of several nucleic acid amplification techniques (vide supra) prior to detection. The nucleic acid analytes of interest from a specimen may also be present in very small numbers (e.g., 1, 7, 29, etc., or zero in the case of a non-infected specimen) or larger numbers ranging into the millions, billions or more. Therefore, it is critical for quantification that the nucleic acid analytes are amplified proportionally to accurately reflect their initial numbers. Attempts to achieve reproducible quantitation of nucleic acids over a dynamic range by using nucleic acid amplification methods has been a challenging endeavor and a number of problems have been encountered including, for example, the need for amplification internal standards and (even very slightly) different amplification efficiencies of internal standards (*Clin. Chem.* 40(4): 630-636 (1994); *Clin. Chem.* 41(8): 1065-1067 (1995); *Biochim. Biophys. Acta* 1219(2): 493-498 (1994); *Biotechniques* 15(1): 134-139 (1993); *J. Infect. Dis.* 165(6): 1119-1123 (1992); *Proc. Nat. Acad. Sci. USA* 86(24): 9717-9721 (1989)). Two basic approaches have been used to solve these problems, with mixed success.

In the first basic approach, the concentration of a target nucleic acid sequence present in a test sample is determined based on the rate at which amplicons are produced over time. An example of this approach is known as "real-time PCR;" increasing amplicon levels are measured with probes that change their fluorescent properties in response to increasing amplicon concentration. The time it takes for the amplicon to reach a predefined level is correlated with the concentration of the target nucleic acid sequence present in the sample by comparing the results of the experimentally detected amplicon to results from standards that contain a range of known amounts of the target nucleic acid sequences. Multiple standards may be used, often ranging from the low to high ends of expected responses from the analyte of unknown concentration. In amplification systems in which the reaction is divided into cycles, such as the PCR or LCR, precision is limited by the amount of amplification that occurs within each cycle; for the PCR, the amount is theoretically a two-fold increase per cycle. However, for amplification systems that lack discrete amplification cycles, such as TMA or SDA, rate changes may be difficult to measure accurately because amplicon concentration can change rapidly over a very short period of time. The accuracy of time and amplicon concentration measurements greatly affects the ability to correlate measured results with an initial target nucleic acid concentration with any degree of precision.

In the second basic approach, the amplification reaction is run for a fixed time, and the amount of amplicon produced is measured and correlated to the concentration of target nucleic acid sequence present in the test sample. Such methods are sometimes referred to as "endpoint" methods because the amplicons are measured at a single point at the end of the reaction rather than at multiple time points during the amplification reaction. These methods typically require the use of an excess of nucleic acid probe relative to the target nucleic acid so that the amount of probe hybridized relates directly to the amount of target present and avoids signal saturation due to excess target, referred to as "target saturation" (e.g., U.S. Pat. No. 4,851,330). If target saturation occurs, the probe signal reaches a plateau and the upper end of the dynamic range is truncated. When large amounts of amplicon are produced, even larger amounts of probe must be used to extend the dynamic range, and the amplicon-probe hybridization signal may exceed the detector's capacity for accurate detection. Furthermore, the background signal is often elevated as probe concentration increases, which limits sensitivity of detection at the lower end of the dynamic range. Lowering the specific activity of the probe can be used to reduce the background signal; however, the sensitivity of detection at low target levels is also often decreased. Thus, optimization of endpoint detection may reduce accuracy on one or both ends of the dynamic range.

Generally, while known amplification systems have been optimized to produce amplicons quantitatively over a large dynamic range, detection systems have been unable to perform accurately over that same broad range. This limitation requires additional steps in the process, such as serial dilution of the amplicons or physical separation steps, in order to reduce non-specific background signal and to measure the amplicon concentration across the full dynamic range. Physical separation or dilution steps increase the complexity and length of the test procedure. Manipulating amplicon products increases the danger of cross-contaminating samples or amplification reaction mixtures, which could lead to false positive results. In addition, amplicon manipulation increases the possibility of errors in quantification, including false negative results. Ideally, a nucleic acid detection and quantitation system should include an amplification reaction that generates measurable amounts of one or more amplicons reproducibly and proportionately across a wide dynamic range, as well as a detection system that can quantitate the amplicons across the same dynamic range.

In certain known methods, a nucleic acid hybridization reaction is used to determine the amount of amplicon by correlating either the rate of hybridization or the extent of hybridization to the amount of amplicon present. However, kinetic measurements of hybridization pose many of the same disadvantages of kinetic measurements of amplification reactions and are thus not preferred.

In some variations of known in vitro nucleic acid amplification procedures, researchers have sought to achieve an extended dynamic range by individually adjusting the efficiencies of amplification of one or more target sequences by optimizing the reaction conditions for each target nucleic acid. However, such optimization generally requires complex and extensive experimentation and may not yield reproducible results because of slight differences between samples, presence of inhibitors in reaction mixtures, variations in test reagents and/or their quantities in individual reaction mixtures, or conditions in which the reactions are performed. Thus, there remains a need to extend the dynamic range of quantitative endpoint assays that does not require excess experimentation and provides a robust system with wide dynamic range.

Compositions and methods that respond to this need would allow quantitative measurement of a desired target nucleic acid in a sample by using nucleic acid amplification and detection of the amplified products over an extended dynamic range. The compositions and methods described herein provide a simple solution to problems associated with previous quantitative nucleic acid amplification and detection methods.

SUMMARY OF THE INVENTION

The present application provides compositions and methods for making multiple differentiable amplicon species at unequal ratios using a single amplification system in a single vessel. The number of differentiable amplicon species and their ratios to one another are chosen to span the required linear dynamic range for the amplification reaction and to accommodate limitations of the measuring system used to determine the amount of any one amplicon generated. Unequal amounts of distinguishable amplicon species are generated by providing unequal amounts of one or more amplification reaction components (e.g., unequal amounts of distinguishable amplification oligomers, unequal amounts of natural and unnatural NTP in an NTP mix, or the like). If small amounts of target nucleic acid are present in the sample, then the more abundant amplicons species is detectable within the linear dynamic range, while the lesser abundant amplicon species is/are below the detection threshold. If greater amounts of target nucleic acid are present in the sample, then less abundant amplicons species become detectable within the linear dynamic range. Here, detection of target amounts can be determined using the detection ranges generated from two or more amplicon species. At higher amounts of target nucleic acid present in the sample, the more abundant amplicon species can saturate the detection system; however, lesser abundance amplicon species are still detectable within their linear dynamic ranges. Therefore, for two amplicons, when a large amount of target nucleic acid is present in a test sample, large amounts of amplicon 1 are generated but smaller amounts of amplicon 2 is also made. If the amount of amplicon 1 is outside the dynamic range of the detection system, then the amounts of amplicon 2 may lie within the dynamic range and can be measured. The amount of original target nucleic acid sequence may then be calculated from the amount of amplicon 2. Additional amplicons can be made to further extend the dynamic range (amplicon 3, etc.).

The present application provides a method for detecting a target nucleic acid in a sample comprising the steps of: providing a sample suspected of containing a target nucleic acid; generating from the target nucleic acid, a defined ratio of at least two differentiable amplicon species, wherein the generating step is performed in a single vessel; and detecting the presence and amount of each generated amplicon species, wherein a first amplicon species is detectable in a first linear range representing a first concentration of target nucleic acid in the sample to a second concentration of target nucleic acid in the sample and a second amplicon species is detectable in a second linear range representing a third concentration of target nucleic acid in the sample to a fourth concentration of target nucleic acid in the sample, and wherein, the first concentration is less that the third concentration, which is less than the second concentration, which is less than the fourth concentration such that said first and second linear ranges overlap and provide an extended dynamic range for determining the presence and amount of the target nucleic acid in the sample, and wherein the detecting step is performed in a single vessel. Preferably, the single well used in the amplifying step and the single vessel used in the vessel are the same vessel. Thus, the amplification and detection reactions take place in the same vessel.

In some aspects of the method, a third differentiable amplicon species is generated. The third differentiable amplicon species will provide a third linear range that is different than the first and the second linear ranges, thereby further extending the dynamic range for determining the presence and amount of the target nucleic acid in the sample. In some aspects, the third amplicon is detectable in a linear range representing a representing a fifth concentration of target nucleic acid in the sample to a sixth concentration of target nucleic acid in the sample, wherein the first concentration is less than the third concentration, which is less than the second concentration, which is less than the fifth concentration, which is less than the fourth concentration, which is less than the sixth concentrations such that the first, second and third linear ranges overlap and provide an extended dynamic range for determining the presence and amount of said target nucleic acid in said sample. In some aspects n differentiable amplicon species are generated to provide n overlapping linear ranges to provide an extended dynamic range; n being equal to a positive whole number.

In some aspects of the methods the at least two differentiable amplicon species are generated using a single amplification oligomer that hybridizes to one strand of the target nucleic acid and at least two amplification oligomers that hybridize to the complementary strand of the target nucleic acid, wherein the at least two amplification oligomers hybridizing to a complementary strand of the target nucleic acid are provided in unequal amounts. In some aspects, the single amplification oligomer is a promoter-based amplification oligomer. In some aspects, the single amplification oligomer is a promoter-provider. In some aspects, the single amplification oligomer is a promoter-primer. In some aspects, the single amplification oligomer is a primer. In some aspects, the at least two amplification oligomers that hybridize to the complementary strand of the target nucleic acid are promoter-based amplification oligomers. In some aspects, the at least two amplification oligomers that hybridize to the complementary strand of the target nucleic acid are promoter-primers. In some aspects, the at least two amplification oligomers that hybridize to the complementary strand of the target nucleic acid are promoter-providers. In some aspects, the at least two amplification oligomers that hybridize to the complementary strand of the target nucleic acid are primers. In some aspects, the at least two differentiable amplicon species are generated using a single promoter based amplification oligomer that hybridizes to one strand of the target nucleic acid and at least two primer that hybridize to the complementary strand of the target nucleic acid. The single promoter-based amplification oligomer is a promoter-provider in some aspects of the methods. The single promoter-based amplification oligomer-is a promoter primer in some aspects of the methods. In some aspects, the at least two differentiable amplicon species are generated using a single primer that hybridizes to one strand of the target nucleic acid and at least two promoter-based amplification oligomers that hybridize to the complementary strand of the target nucleic acid. The at least two promoter-based amplification oligomers are promoter-providers in some aspects of the methods. The at least two promoter-based amplification oligomers are promoter primers in some aspects of the methods. In some aspects, the at least two differentiable amplicon species are generated using a single primer that hybridizes to one strand of the target nucleic acid and at least two primers that hybridize to the complementary strand of the target nucleic acid.

In some aspects of the methods wherein the at least two differentiable amplicon species are generated using a single amplification oligomer that hybridizes to one strand of the target nucleic acid and unequal amounts of at least two amplification oligomers that hybridize to the complementary strand of the target nucleic acid, the at least two amplification oligomers hybridizing to the complementary strand of the target nucleic acid hybridize to distinct sequences of said target nucleic acid, thereby generating from the target nucleic acid, a defined ratio of at least two differentiable amplicon species that differ in length. In some aspects, the distinct sequences of the target nucleic acid to which the at least two amplification oligomers hybridize, are non-overlapping sequences. In some aspects, the distinct sequences of the target nucleic acid to which the at least two amplification oligomers hybridize, are overlapping sequences.

In some aspects of the methods wherein the at least two differentiable amplicon species are generated using a single amplification oligomer that hybridizes to one strand of the target nucleic acid and unequal amounts of at least two amplification oligomers that hybridize to the complementary strand of the target nucleic acid, the at least two amplification oligomers hybridizing to the complementary strand of the target nucleic acid have distinct nucleic acid sequences, thereby generating from the target nucleic acid, a defined ratio of at least two differentiable amplicon species that differ in nucleic acid composition. In some aspects, the at least two amplification oligomers are substantially identical in nucleotide sequence except that one amplification oligomer has one or more of: at least one nucleotide mismatch, at least one nucleotide insertion, at least one nucleotide deletion and combinations thereof, thereby generating from said target nucleic acid, a defined ratio of at least two differentiable amplicon species that differ in nucleic acid composition. In some aspects, the at least two amplification oligomers each contain at least one insertion, wherein the at least one insertion in one of the at least two amplification oligomers is different from the at least one insertion of the other at least one amplification oligomers. In some aspects, each of the at least one amplification oligomers comprises a unique unhybridized nucleotide sequence that is at least one nucleobase in length and that is joined to the 5' end of the target hybridizing region of the amplification oligomer.

In some aspects of the methods, the two differentiable amplicon species are generated using an amplification method wherein said amplification method generates RNA amplicon species and DNA amplicon species to provide at least two differentiable amplicons that differ in ribose sugar composition. In some aspects, the amplification method is an isothermal amplification method that uses at least one promoter-based amplification oligomer to generate a greater amount of RNA amplicon species that of DNA amplicon species.

In some aspects of the methods, the two differentiable amplicon species are generated using a dNTP mixture wherein at least one of said dNTP species in said mix is provided in both a native form and in an analog form with one form in excess of the other form to provide at least two differentiable amplicons that differ in nucleic acid composition. In some aspects, the dNTP mix contains native dATP and an analog of dATP. In some aspects, the dNTP mix contains native dCTP and an analog of dCTP. In some aspects, the dNTP mix contains native dTTP and an analog of dTTP. In some aspects, the dNTP mix contains native dGTP and an analog of dGTP. In some aspects, the dNTP mix contains native dUTP and an analog of dUTP.

In some aspects, the amplification step is performed with an isothermal amplification reaction. In some aspects, the amplification step is performed with an cyclical amplification reaction. In some aspects, the amplification step is performed with a TMA amplification reaction. In some aspects, the amplification step is performed with a NASBA amplification reaction. In some aspects, the amplification step is performed with a PCR amplification reaction. In some aspects, the amplification step is performed with a Reverse Transcription (RT)-PCR amplification reaction. In some aspects, the amplification step is performed with a real time amplification reaction. In some aspects, the amplification step is performed with a rolling circle amplification reaction. In some aspects, the amplification step is performed with a helicase dependent amplification reaction.

The present application provides a method for amplifying a target nucleic acid sequence in a test sample comprising: (a) contacting the test sample with a nucleic acid amplification reaction mixture comprising at least two primers, wherein the at least two primers hybridize to the same strand of the target nucleic acid sequence but hybridize to distinct nucleotide sequences on the strand, and each of the at least two primers is present in the reaction mixture in a different amount; and (b) subjecting the reaction mixture to amplification conditions under which each of the at least two primers simultaneously and independently produces one of each of two distinguishable amplicons from the target nucleic acid sequence, wherein the number of copies of each amplicon produced depends on the amount of each of the at least two primers in the reaction mixture, and the number of copies of each amplicon produced differs by at least two orders of magnitude.

In some aspects, each of the at least two primers further differ from one another by having one or more of (i) one of the amplification oligomers has a modified target hybridizing sequence and the other does not and/or (ii) each of the amplification oligomers has a different unique unpaired 5' sequence.

The present application provides a method for quantitating a target nucleic acid sequence in a test sample comprising: (a) contacting the test sample with a nucleic acid amplification reaction mixture comprising at least two primers, wherein the at least two primers hybridize to the same strand of the target nucleic acid sequence but hybridize to distinct nucleotide sequences on the strand, and each of the at least two primers is present in the reaction mixture in a different amount; (b) subjecting the reaction mixture to amplification conditions under which each of the at least two primers simultaneously and independently produces one of at least two amplicons, wherein the number of copies of each amplicon produced differs by at least two orders of magnitude; (c) hybridizing the at least two amplicons with at least two probes, wherein each of the at least two probes is specific to one of the at least two amplicons, each probe is detectable within a detection range, wherein the sum of the detection ranges for each of the at least two probes is greater than the detection range for each probe, such that the at least two probes together are detectable across a wide dynamic range, and the at least two probes produce distinguishable detection signals; (d) detecting at least one of the at least two probes; and (e) determining the initial amount of target nucleic acid sequence in the test sample.

In some aspects, each of the at least two primers further differ from one another by having one or more of (i) one of the amplification oligomers has a modified target hybridizing sequence and the other does not and/or (ii) each of the amplification oligomers has a different unique unpaired 5' sequence.

The present application further provides a method for quantitating a nucleic acid in a test sample comprising: (a) providing a test sample suspected of containing a target nucleic acid in an amount $T_1$; (b) contacting the test sample with a nucleic acid amplification reaction mixture comprising at least two primers, wherein the at least two primers hybridize to the same strand of the target nucleic acid sequence but each primer hybridizes to a distinct nucleotide sequence on the strand, and wherein each primer is present in the reaction mixture in a different amount. In one aspect, each $P_x$ differs by at least two orders of magnitude, and where x is an integer between 1 and the number of primers in the mixture. (c) Subjecting the reaction mixture to amplification conditions under which each of the at least two primers simultaneously and independently produces one of at least two amplicons, wherein for each amplicon, a number of copies $A_x$ is produced, and wherein each $A_x$ differs by an amount that is approximately the same as the amount of difference in each $P_x$ for the primers present in the mix. In one aspect, the $A_x$ for each amplicon differs by at least two orders of magnitude. (d) Hybridizing the at least two amplicons with at least two probes, wherein each of the at least two probes is specific to one of the at least two amplicons, each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals; (e) detecting at least one of the at least two probes; and (f) determining the initial amount of target nucleic acid sequence in the test sample.

In some aspects, each of the at least two primers further differ from one another by having one or more of (i) one of the amplification oligomers has a modified target hybridizing sequence and the other does not and/or (ii) each of the amplification oligomers has a different unique unpaired 5' sequence.

The present application further provides a composition for amplifying a target nucleic acid sequence in a test sample comprising at least two primers, wherein (a) the at least two primers hybridize to the same strand of the target nucleic acid sequence but hybridize to distinct nucleotide sequences on the strand, and each of the at least two primers is present in the reaction mixture in a different amount; and (b) under amplification conditions, each of the at least two primers simultaneously and independently produces one of each of two detectable amplicons from the target nucleic acid sequence, wherein the number of copies of each amplicon produced depends on the amount of each of the at least two primers in the reaction mixture, the number of copies of each amplicon produced differs by at least two orders of magnitude, and the amplicons are detectable across a wide dynamic range.

In some aspects, each of the at least two primers further differ from one another by having one or more of (i) one of the amplification oligomers has a modified target hybridizing sequence and the other does not and/or (ii) each of the amplification oligomers has a different unique unpaired 5' sequence.

The present application further provides a nucleic acid amplification reaction mixture comprising at least two primers, wherein: (a) the at least two primers hybridize to the same strand of a target nucleic acid sequence but each primer hybridizes to a distinct nucleotide sequence on the strand; wherein each primer is present in the reaction mixture at a different amount $P_x$, where x is an integer between 1 and the number of primers in the mixture; (b) under amplification conditions, each primer simultaneously and independently produces one of at least two amplicons from the target nucleic acid sequence, wherein for each amplicon, a number of copies $A_x$ is produced, and wherein each $A_x$ differs by an amount that is approximately same as the amount of difference in each $P_x$ of the at least two primers. In one aspect, the difference in the $A_x$ for each amplicon is at least two orders of magnitude. (c) The at least two amplicons are detectable by hybridization with at least two probes, wherein each of the at least two probes is specific to one of the at least two amplicons, and each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals.

In some aspects, each of the at least two primers further differ from one another by having one or more of (i) one of the amplification oligomers has a modified target hybridizing sequence and the other does not and/or (ii) each of the amplification oligomers has a different unique unpaired 5' sequence.

The present application provides a method for amplifying a target nucleic acid sequence in a test sample comprising: (a) contacting the test sample with a nucleic acid amplification reaction mixture comprising at least two amplification oligomers, wherein the at least two amplification oligomers hybridize to the same strand of the target nucleic acid sequence but hybridize to distinct nucleotide sequences on the strand, and each of the at least two amplification oligomers is present in the reaction mixture in a different amount; and (b) subjecting the reaction mixture to amplification conditions under which each of the at least two amplification oligomers simultaneously and independently produces one of each of two distinguishable amplicons from the target nucleic acid sequence, wherein the number of copies of each amplicon produced depends on the amount of each of the at least two amplification oligomers in the reaction mixture, and the number of copies of each amplicon produced differs by at least two orders of magnitude.

In some aspects, the at least two amplification oligomers are promoter-based amplification oligomers. In some aspects, each of the at least two amplification oligomers further differ from one another by having one or more of (i) one of the amplification oligomers has a modified target hybridizing sequence and the other does not and/or (ii) each of the amplification oligomers has a different unique unpaired 5' sequence.

The present application provides a method for quantitating a target nucleic acid sequence in a test sample comprising: (a) contacting the test sample with a nucleic acid amplification reaction mixture comprising at least two amplification oligomers, wherein the at least two amplification oligomers hybridize to the same strand of the target nucleic acid sequence but hybridize to distinct nucleotide sequences on the strand, and each of the at least two amplification oligomers is present in the reaction mixture in a different amount; (b) subjecting the reaction mixture to amplification conditions under which each of the at least two amplification oligomers simultaneously and independently produces one of at least two amplicons, wherein the number of copies of each amplicon produced differs by at least two orders of magnitude; (c) hybridizing the at least two amplicons with at least two probes, wherein each of the at least two probes is specific to one of the at least two amplicons, each probe is detectable within a detection range, wherein the sum of the detection ranges for each of the at least two probes is greater than the detection range for each probe, such that the at least two probes together are detectable across a wide dynamic range, and the at least two probes produce distinguishable detection signals; (d) detecting at least one of the at least two probes; and (e) determining the initial amount of target nucleic acid sequence in the test sample.

In one aspect, the at least two amplification oligomers are promoter-based amplification oligomers. In some aspects, each of the at least two amplification oligomers further differ from one another by having one or more of (i) one of the amplification oligomers has a modified target hybridizing sequence and the other does not and/or (ii) each of the amplification oligomers has a different unique unpaired 5' sequence.

The present application further provides a method for quantitating a nucleic acid in a test sample comprising: (a) providing a test sample suspected of containing a target nucleic acid in an amount $T_1$; (b) contacting the test sample with a nucleic acid amplification reaction mixture comprising at least two amplification oligomers, wherein the at least two amplification oligomers hybridize to the same strand of the target nucleic acid sequence but each amplification oligomers hybridizes to a distinct nucleotide sequence on the strand, and wherein each amplification oligomers is present in the reaction mixture in a different amount. In one aspect, each $P_x$ differs by at least two orders of magnitude, and where x is an integer between 1 and the number of amplification oligomers in the mixture. (c) Subjecting the reaction mixture to amplification conditions under which each of the at least two amplification oligomers simultaneously and independently produces one of at least two amplicons, wherein for each amplicon, a number of copies $A_x$ is produced, and wherein each $A_x$ differs by an amount that is approximately the same as the amount of difference in each $P_x$ for the at least two amplification oligomers hybridizing to the same strand of the target nucleic acid sequence present in the mix. In one aspect, the $A_x$ for each amplicon differs by at least two orders of magnitude. (d) Hybridizing the at least two amplicons with at least two probes, wherein each of the at least two probes is specific to one of the at least two amplicons, each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals; (e) detecting at least one of the at least two probes; and (f) determining the initial amount of target nucleic acid sequence in the test sample.

In some aspects, the at least two amplification oligomers are promoter-based amplification oligomers. In some aspects, each of the at least two amplification oligomers further differ from one another by having one or more of (i) one of the amplification oligomers has a modified target hybridizing sequence and the other does not and/or (ii) each of the amplification oligomers has a different unique unpaired 5' sequence.

The present application further provides a composition for amplifying a target nucleic acid sequence in a test sample comprising at least two amplification oligomers, wherein: (a) the at least two amplification oligomers hybridize to the same strand of the target nucleic acid sequence but hybridize to distinct nucleotide sequences on the strand, and each of the at least two amplification oligomers is present in the reaction mixture in a different amount; and (b) under amplification conditions, each of the at least two amplification oligomers simultaneously and independently produces one of each of two detectable amplicons from the target nucleic acid sequence, wherein the number of copies of each amplicon produced depends on the amount of each of the at least two amplification oligomers in the reaction mixture, the number of copies of each amplicon produced differs by at least two orders of magnitude, and the amplicons are detectable across a wide dynamic range.

In some aspects, the at least two amplification oligomers are promoter-based amplification oligomers. In some aspects, each of the at least two amplification oligomers further differ from one another by having one or more of (i) one of the amplification oligomers has a modified target hybridizing sequence and the other does not and/or (ii) each of the amplification oligomers has a different unique unpaired 5' sequence.

The present application further provides a nucleic acid amplification reaction mixture comprising at least two amplification oligomers, wherein: (a) the at least two amplification oligomers hybridize to the same strand of a target nucleic acid sequence but each amplification oligomer hybridizes to a distinct nucleotide sequence on the strand; wherein each primer is present in the reaction mixture at a different amount $P_x$, where x is an integer between 1 and the number of primers in the mixture; (b) under amplification conditions, each primer simultaneously and independently produces one of at least two amplicons from the target nucleic acid sequence, wherein for each amplicon, a number of copies $A_x$ is produced, and wherein each $A_x$ differs by an amount that is approximately same as the amount of difference in each $P_x$ of the at least two amplification oligomers hybridizing to the same strand of the target nucleic acid sequence. In one aspect, the difference in the $A_x$ for each amplicon is at least two orders of magnitude; (c) the at least two amplicons are detectable by hybridization with at least two probes, wherein each of the at least two probes is specific to one of the at least two amplicons, and each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals.

In some aspects, the at least two amplification oligomers are promoter-based amplification oligomers. In some aspects, each of the at least two amplification oligomers further differ from one another by having one or more of (i) one of the amplification oligomers has a modified target hybridizing sequence and the other does not and/or (ii) each of the amplification oligomers has a different unique unpaired 5' sequence.

The present application provides a method for amplifying a target nucleic acid sequence in a test sample comprising: (a) contacting the test sample with a nucleic acid amplification reaction mixture comprising at least two amplification oligomers, wherein the at least two amplification oligomers hybridize to the same sequence on the same strand of the target nucleic acid sequence but each of the at least two amplification oligomers differ from one another by having one or more of (i) one of the amplification oligomers has a modified target hybridizing sequence and the other does not and/or (ii) each of the amplification oligomers has a different unique unpaired 5' sequence, and each of the at least two amplification oligomers is present in the reaction mixture in a different amount; and (b) subjecting the reaction mixture to amplification conditions under which each of the at least two amplification oligomers simultaneously and independently produces one of each of two distinguishable amplicons from the target nucleic acid sequence, wherein the number of copies of each amplicon produced depends on the amount of each of the at least two amplification oligomers in the reaction mixture, and the number of copies of each amplicon produced differs by at least two orders of magnitude.

In some aspects, the at least two amplification oligomers are promoter-based amplification oligomers. In some aspects, the at least two amplification oligomers are primers.

The present application provides a method for quantitating a target nucleic acid sequence in a test sample comprising: (a) contacting the test sample with a nucleic acid amplification reaction mixture comprising at least two amplification oligomers, wherein the at least two amplification oligomers hybridize to the same sequence on the same strand of the target nucleic acid sequence but each of the at least two amplification oligomers differ from one another by having one or more of (i) one of the amplification oligomers has a modified target hybridizing sequence and the other does not and/or (ii) each of the amplification oligomers has a different unique unpaired 5' sequence, and each of the at least two amplification oligomers is present in the reaction mixture in a different amount; (b) subjecting the reaction mixture to amplification conditions under which each of the at least two amplification oligomers simultaneously and independently produces one of at least two amplicons, wherein the number of copies of each amplicon produced differs by at least two orders of magnitude; (c) hybridizing the at least two amplicons with at least two probes, wherein each of the at least two probes is specific to one of the at least two amplicons, each probe is detectable within a detection range, wherein the sum of the detection ranges for each of the at least two probes is greater than the detection range for each probe, such that the at least two probes together are detectable across a wide dynamic range, and the at least two probes produce distinguishable detection signals; (d) detecting at least one of the at least two probes; and (e) determining the initial amount of target nucleic acid sequence in the test sample.

In one aspect, the at least two amplification oligomers are promoter-based amplification oligomers. In some aspects, the at least two amplification oligomers are primers.

The present application further provides a method for quantitating a nucleic acid in a test sample comprising: (a) providing a test sample suspected of containing a target nucleic acid in an amount $T_1$; (b) contacting the test sample with a nucleic acid amplification reaction mixture comprising at least two amplification oligomers, wherein the at least two amplification oligomers hybridize to the same sequence on the same strand of the target nucleic acid sequence but each of the at least two amplification oligomers differ from one another by having one or more of (i) one of the amplification oligomers has a modified target hybridizing sequence and the other does not and/or (ii) each of the amplification oligomers has a different unique unpaired 5' sequence, and wherein each amplification oligomers is present in the reaction mixture in a different amount. In one aspect, each $P_x$ differs by at least two orders of magnitude, and where x is an integer between 1 and the number of amplification oligomers in the mixture. (c) Subjecting the reaction mixture to amplification conditions under which each of the at least two amplification oligomers simultaneously and independently produces one of at least two amplicons, wherein for each amplicon, a number of copies $A_x$ is produced, and wherein each $A_x$ differs by an amount that is approximately the same as the amount of difference in each $P_x$ for the at least two amplification oligomers hybridizing to the same strand of the target nucleic acid sequence present in the mix. In one aspect, the $A_x$ for each amplicon differs by at least two orders of magnitude. (d) Hybridizing the at least two amplicons with at least two probes, wherein each of the at least two probes is specific to one of the at least two amplicons, each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals; (e) detecting at least one of the at least two probes; and (f) determining the initial amount of target nucleic acid sequence in the test sample.

In some aspects, the at least two amplification oligomers are promoter-based amplification oligomers. In some aspects, the at least two amplification oligomers are primers.

The present application further provides a composition for amplifying a target nucleic acid sequence in a test sample comprising at least two amplification oligomers, wherein: (a) the at least two amplification oligomers hybridize to the same sequence of the same strand of the target nucleic acid sequence but each of the at least two amplification oligomers differ from one another by having one or more of (i) one of the amplification oligomers has a modified target hybridizing sequence and the other does not and/or (ii) each of the amplification oligomers has a different unique unpaired 5' sequence, and each of the at least two amplification oligomers is present in the reaction mixture in a different amount; and (b) under amplification conditions, each of the at least two amplification oligomers simultaneously and independently produces one of each of two detectable amplicons from the target nucleic acid sequence, wherein the number of copies of each amplicon produced depends on the amount of each of the at least two amplification oligomers in the reaction mixture, the number of copies of each amplicon produced differs by at least two orders of magnitude, and the amplicons are detectable across a wide dynamic range.

In some aspect, the at least two amplification oligomers are promoter-based amplification oligomers. In some aspects, the at least two amplification oligomers are primers.

The present application further provides a nucleic acid amplification reaction mixture comprising at least two amplification oligomers, wherein: (a) the at least two amplification oligomers hybridize to the same sequence of the same strand of a target nucleic acid sequence but each of the at least two amplification oligomers differ from one another by having one or more of (i) one of the amplification oligomers has a modified target hybridizing sequence and the other does not and/or (ii) each of the amplification oligomers has a different unique unpaired 5' sequence; wherein each primer is present in the reaction mixture at a different amount $P_x$, where x is an integer between 1 and the number of primers in the mixture; (b) under amplification conditions, each primer simultaneously and independently produces one of at least two amplicons from the target nucleic acid sequence, wherein for each amplicon, a number of copies $A_x$ is produced, and wherein each $A_x$ differs by an amount that is approximately same as the amount of difference in each $P_x$ of the at least two amplification oligomers hybridizing to the same strand of the target nucleic acid sequence. In one aspect, the difference in the $A_x$ for each amplicon is at least two orders of magnitude. (c) The at least two amplicons are detectable by hybridization with at least two probes, wherein each of the at least two probes is specific to one of the at least two amplicons, and each probe is detectable within a linear detection range $C_{x(a)}$ to $C_{x(b)}$, wherein $C_{x(a)}$ is the minimum detectable number of copies of amplicon and $C_{x(b)}$ is the maximum detectable number of copies of amplicon for probe x, wherein for each probe, $C_{x+1(a)}$ is greater than $C_{x(a)}$ and $C_{x+1(b)}$ is greater than $C_{x(b)}$ such that the at least two probes together are detectable across a wide dynamic range, wherein for each amplicon-probe combination, $A_x$ is between $C_{x(a)}$ and $C_{x(b)}$, and wherein the at least two probes produce distinguishable detection signals.

In some aspects, the at least two amplification oligomers are promoter-based amplification oligomers. In some aspects, the at least two amplification oligomers are primers.

The present application further provides reaction mixtures comprising at least three amplification oligomers, wherein a one of the amplification oligomers hybridizes to one strand of a target nucleic acid and a second and a third of the amplification oligomers hybridize to the other strand of a target nucleic acid in order to produce two or more differentiable amplicons. Each species of differentiable amplicon is defined at one end by the common first amplification oligomer. The two amplification oligomers hybridizing the same strand will define the opposite end of their respective amplicon species. In some aspects, the at least three amplification oligomers are at least three primers. In some aspects, the at least three amplification oligomers are a primer hybridizing to one strand of a target nucleic acid and two promoter-based oligomers hybridizing to the other strand of a target nucleic acid. In some aspects, the at least three amplification oligomers are a promoter based amplification oligomer hybridizing to one strand of a target nucleic acid and two primers hybridizing to the other strand of a target nucleic acid. In some aspects, the second and a third of the amplification oligomers hybridizing to the same strand of a target nucleic acid, differ by hybridizing to different sequences on the target nucleic acid. In some aspects, the second and a third of the amplification oligomers hybridizing to the same strand of a target nucleic acid, differ from one another by having one or more of (i) one of the amplification oligomers has a modified target hybridizing sequence and the other does not and/or (ii) each of the amplification oligomers has a different unique unpaired 5' sequence.

The present application further provides reaction mixtures comprising at least two detection probe oligomers each of which hybridize to one of two or more differentiable amplicons generated using at least three amplification oligomers, wherein a one of the amplification oligomers hybridizes to one strand of a target nucleic acid and a second and a third of the amplification oligomers hybridize to the other strand of a target nucleic acid. In some aspects, the detectable probe oligomers are labeled different chemiluminescent labels. In some aspects the detectable probe oligomers are labeled different fluorescent labels. In some aspects the detectable probe oligomers are labeled different fluorescent labels and/or different chemiluminescent labels.

BRIEF DESCRIPTION OF THE FIGURES

FIG. 1 is a diagram that illustrates components of in vitro amplification reactions described in Example 1. FIG. 1A depicts the locations of the promoter-primer (Pr-primer; SEQ ID NO:1), Primer 1 (SEQ ID NO:2), and Primer 2 (SEQ ID NO:3) relative to a target RNA transcript (SEQ ID NO:4) (described in the "Amplification Compositions" section of the Examples). FIG. 1B shows a shorter amplicon (SEQ ID NO:9) and a longer amplicon (SEQ ID NO:10) that result from the reaction of (a) the Pr-primer and Primer 1 and (b) the Pr-primer and Primer 2, respectively, and the locations of the two amplicons relative to the sequences in FIG. 1A. FIG. 1C depicts the positions of labeled detection probes of SEQ ID NOS:5 and 6 (described in the "Detection Compositions" section of the Examples) relative to the amplicons of FIG. 1B.

FIG. 4 is a diagram that illustrates the relative alignment of the primers to the RNA transcript, the resulting amplicons, and the relative alignment of the probes to the amplicons used in Examples 2, 3 and 5. As in FIG. 1, FIG. 4A depicts the locations of the promoter primer (Pr-primer; SEQ ID NO:1), Primer 1 (SEQ ID NO:2), and Primer 2 (SEQ ID NO:3) relative to a target RNA transcript (SEQ ID NO:4), and FIG. 4B shows the two amplicons (SEQ ID NOS:9 and 10) which result from the reaction of (a) the Pr-primer and Primer 1 and (b) the Pr-primer and Primer 2, and the locations of the two amplicons relative to the sequences in FIG. 4A. FIG. 4C depicts the positions of labeled and unlabeled detection probes SEQ ID NO:7 and SEQ ID NO:8 (described in the "Detection Compositions" section of the Examples) relative to the amplicons of FIG. 4B.

DETAILED DESCRIPTION OF THE INVENTION

Figure 2:
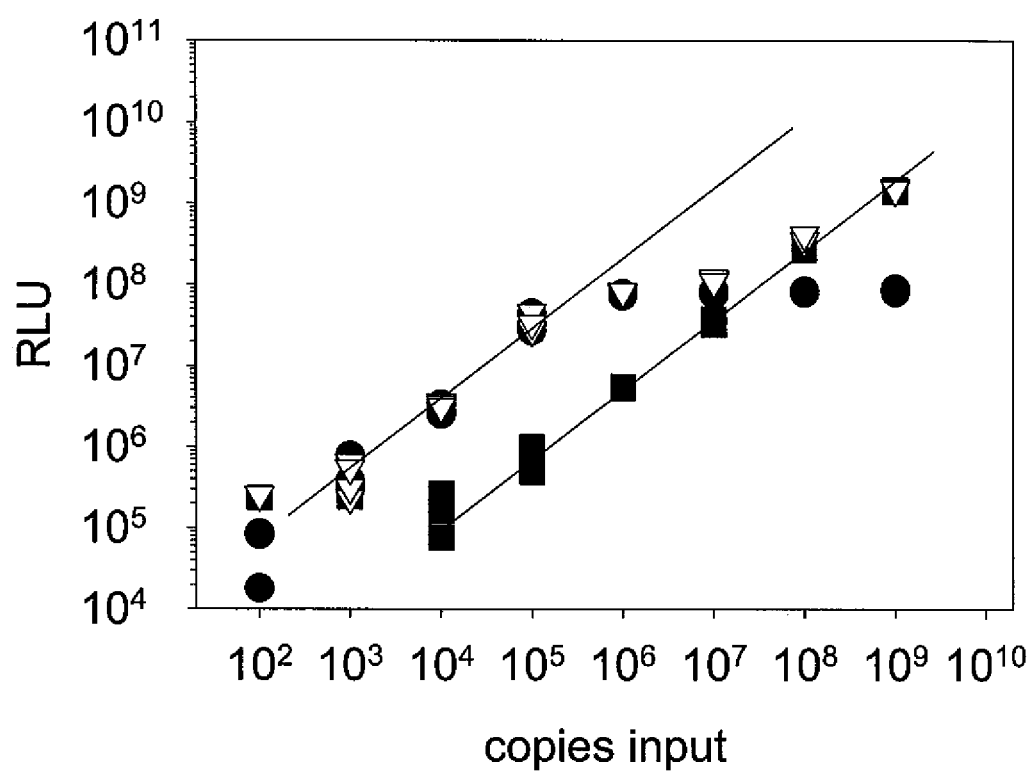
FIG. 2 is a graph that shows the mean, background-subtracted, specific activity-adjusted signal output (y-axis, reported across a range of about $10^4$ to about $10^9$ RLU for "relative light units") detected by using linear AE-labeled probes hybridized to amplicons of target RNA across a range of $10^2$ to $10^9$ input target RNA copies (x-axis) as described in Example 1. Results are shown for (a) labeled probes (1 nM; SEQ ID NO:5) mixed with unlabeled oligonucleotides (50 nM; SEQ ID NO:5) (black circles); (b) labeled probes (1 nM; SEQ ID NO:6) mixed with unlabeled oligonucleotides (200 nM; SEQ ID NO:6) (black squares); and (c) the sum of detection signals from (a) and (b) (white triangles).

As used herein, the terms "including," "containing," and "comprising" are used in their open, non-limiting sense.

As used herein, "a" or "an" means "at least one" or "one or more."

For any quantitative expression used herein, it is understood the quantity is meant to refer to the actual value and is also meant to refer to the approximation of the value that would be inferred by one of skill in the art, including approximations due to the experimental and/or measurement conditions for the given value. This inference is intended regardless of whether the term "about" is used explicitly with the quantity or not.

Target nucleic acids for the present methods and compositions include double-stranded and single-stranded targets. Target nucleic acids may be full-length sequences or fragments thereof and may be RNA or DNA. In its broadest use, the term target nucleic acids refers to the nucleic acids present in the biological sample and the amplified copy thereof. The amplified copy, may be referred to herein as "amplified copy," "amplified strand," "cDNA," "synthesized complementary sequence," "RNA transcript" or other similar term indicating that the referenced strand is not from the biological sample. Under the present method, target nucleic acid in a test sample may be detected and quantified in amounts ranging from 0 to about $10^{12}$ copies.

The term "dynamic range," as used herein, refers to the ratio between the largest and smallest concentrations or number of copies of a target nucleic acid that can be detected. In such cases, the dynamic range is used without any designated units. In some circumstances, "dynamic range" is used to refer to limiting values of detection (e.g., the high and low limits of detection), in which case the appropriate unit measure, such as µM or copies, is designated. A "wide" or "broad" dynamic range for the present invention is about $10^2$ to $10^{10}$ in terms of the detectable number of copies, or may be range of $10^3$ to $10^7$ in terms of ratio. For example, a detection method according to the invention may accurately detect amounts ranging from about $10^3$ to $10^{10}$ input target nucleic acid copies (a dynamic range of about $10^7$), from about $10^4$ to $10^{10}$ input sequence copies (a dynamic range of $10^6$), amounts ranging from $10^3$ to $10^9$ input sequence copies (a dynamic range of $10^6$), or amounts ranging from $10^6$ to $10^{10}$ input sequence copies (a dynamic range of $10^4$). Thus, in some embodiments, the methods and compositions provided herein allow for a detection range from about $10^3$ to $10^7$ or from about $10^4$ to $10^6$. Ranges are understood to be the recited values and the whole and partial values in between (e.g. $10^2$ to $10^{10}$ includes the recited values and values in between such as $10^5$, $2.5 \times 10^6$, $10^{4.5}$, $10^{8.3}$, etc.).

The term "distinguishable," as used herein, refers to the characteristic of a nucleic acid sequence that allows it to be detected in a manner that distinguishes it from another nucleic acid sequence. For example, two amplicons are distinguishable when they are capable of being independently detected by two selective probes. The two probes will generate signals that may be detected individually and without significant interference between them, e.g., through different wavelengths, different radioligands, or different chemically-detectable devices (such as a fluorophore and a chemiluminescent probe), or a mixture of such signaling mechanisms.

In particular, the term "distinguishable detection signal" refers to the signals produced by two or more probes. To be "distinguishable," the signals produced by the individual probes are differentiable by standard detection devices. The signals are readily quantifiable by a detection instrument without unwarranted interference or overlap between the signals. For example, probes that produce distinguishable detection signals are those that produce signals at wavelengths sufficiently separated to be accurately detected and quantified by a detection instrument.

The term "amplification oligomer" refers to oligonucleotide sequences useful for amplification of a target nucleic acid. Amplification oligomers include primers, promoter-based amplification oligomers, promoter primers, promoter providers and the like.

The term "promoter-based amplification oligomer" includes promoter-primers and promoter-providers. A "promoter-provider" or "provider" refers to an oligonucleotide comprising first and second regions, and which is modified to prevent the initiation of DNA synthesis from its 3'-terminus. The "first region" or "target hybridizing region" of a promoter-provider oligonucleotide comprises a base sequence which hybridizes to a DNA template, where the hybridizing sequence is situated 3', but not necessarily adjacent to, a promoter region. The target hybridizing region of a promoter-based oligonucleotide is typically at least 10 nucleotides in length, and may extend up to 50 or more nucleotides in length. The "second region" or "promoter region" comprises a promoter sequence for an RNA polymerase. A promoter provider is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" or T7 Promoter Provider is a blocked promoter-provider oligonucleotide that provides an oligonucleotide sequence that is recognized by T7 RNA polymerase. A similar oligomer that lacks modification to the 3'-terminus is called a "promoter primer." T7 or other promoter sequences are useful for promoter-based amplification oligomers. As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, the term "primer" refers to an oligonucleotide that hybridizes a target nucleic acid and produces an amplicon therefrom.

For some embodiments of the presently disclosed methods and compositions, at least three amplification oligomers are used together, one amplification oligomer hybridizing one strand and two amplification oligomers hybridizing the other strand. In any given method or composition, at least two amplification oligomers read the target nucleic acid in the same direction, i.e., either all forward amplification oligomers or all reverse amplification oligomers. The at least three amplification oligomers include, then, a forward or reverse amplification oligomer and at least two reverse or forward amplification oligomers, respectively. The at least two amplification oligomers hybridizing the same strand of the target nucleic acid (i.e. same direction) generate differentiable amplicons by hybridizing two distinct sequences within the target nucleic acid sequence, by hybridizing the same sequences within the target nucleic acid sequence but by also providing differentiable sequences (modified and unmodified sequences, unique non-hybridizing 5' sequences or the like). For the same direction amplification oligomers, their target sequences on the target nucleic acid, when distinct, may overlap. The at least two amplification oligomers are provided in unequal amounts, thereby generating their respective differentiable amplicons in approximately the same unequal amounts.

For some embodiments of the presently disclosed methods and compositions, at least two amplification oligomers are used together, one amplification oligomer hybridizing one strand and one amplification oligomer hybridizing the other strand. Using this embodiment, the differentiable amplicons generated with these amplification oligomers differ in their nucleotide composition. For example, using a dNTP mix that provides one of the dNTPs in an unequal ratio of native dNTP to analog dNTP will generate unequal amplicons species having the native or analogue residues. As a further example, using an amplification reaction that generates RNA amplicon species and DNA amplicon species will also generate unequal amplicons species comprising RNA or DNA.

As used herein, the term "amplicon" refers to the product generated from the hybridization of an amplification oligomer with its target sequence under amplification conditions. Amplicons can include double stranded DNA, as is generated in PCR amplification reactions and some steps of isothermal amplification reactions, DNA:RNA hybrids as are generated in some steps of RT-PCR and some steps of isothermal amplification reactions, or single stranded RNA as are generated in some steps of isothermal amplification.

As used herein, the term "amplification oligomer-amplicon combination" or "amplification oligomer-amplicon system" refers to an amplification oligomer and the specific amplicon produced therefrom. The amplification oligomer referred to in some embodiments is one of the differentiable same direction amplification oligomers that are described herein for generating differentiable amplicons.

As used herein, the term "probe" refers to a DNA or RNA fragment, oligonucleotide or transcript capable of detecting the presence of a particular nucleotide sequence that is complementary to the sequence in the probe. Probes are suitably tagged or labeled with a molecular marker that can be detected by a detection instrument. Suitable probes and instruments are known in the art. Probes useful in the methods and compositions described herein may be any probe which allows for quantitative detection of a nucleic acid product. Suitable probes include chemiluminescent probes (including self-quenching varieties), fluorophore-based probes, wavelength-detectable probes, radiolabelled probes, and the like. Particularly useful probes include those labeled with chemiluminescent labels, such as acridinium esters (AE), hybridization-induced chemiluminescent signal (HICS) labels, fluorophore-AE hybrid labels, and the like. In particular, HICS probes are described in, e.g., U.S. Pat. No. 7,169,554. HICS probes may include wavelength-shifted HICS (wsHICS) probes in which the emission wavelength is shifted from AE to that of a proximal fluorophore in a self-quenching probe format (e.g., U.S. Pat. No. 6,165,800). Thus, self-quenching energy transfer probes are examples of suitable probes for use in the present methods. Particularly suitable probes include acridinium ester probes or HICS probes.

Suitable amplification conditions include the amplification methods described herein. For example, the isothermal amplification or cyclical amplification methods are appropriate for use in the methods and with the compositions described herein.

The methods and compositions described herein provide quantitative amplification of target nucleic acid sequences that may be present in a test sample by using various means to produce different quantities of distinguishable detectable amplicon products in known proportions. The described methods and compositions generate multiple differentiable amplicons at ratios relative to each other and relative to the amount of target nucleic acid sequence. Amplification of a target nucleic acid sequence with a single pair of amplification oligomer could generate an amplicon with a concentration outside the accurate detection range of a probe or the detection instrument. According to the present invention, in contrast, multiple amplification oligomer-amplicon systems are used to simultaneously generate multiple differentiable amplicons at differing amplicon concentrations. Thus, rather than one narrow window of accurate detection, the present method creates multiple overlapping detection ranges, each of which is accurate for a particular species of amplicon product. The present method produces multiple differentiable amplicons in a single amplification system, which is preferably performed in a single vessel. The differentiable amplicons may differ in length, wherein the amplicon species share a common sequence, but wherein each longer amplicon species adds additional sequence that is unique to the longer species compared to the shorter. The differentiable amplicons may differ in composition, wherein one or more modified nucleobases in incorporated into a species of amplicon, but not into other(s). Similarly, the differentiable amplicons may differ in composition, wherein separately unique 5' sequences are incorporated into each species of amplicon by using amplification oligomers with 5' non-hybridizing sequences. The differentiable amplicons may differ in composition, wherein a modified nucleobase is combined with an unmodified nucleobase for incorporation into a subset of amplicons (e.g., a dNTP mix having a ratio of dATP and modified dATP or a substitute for dATP).

In these methods, the number of differentiable amplicons and their fixed ratios relative to one another are chosen to span the required dynamic range for the amplification reaction and to accommodate limitations of the measuring system that detects the amount of the amplicons generated in the amplification reaction. In essence, the amplicons are surrogate markers for the target nucleic acid sequence and appear (and are thus detectable) at a wide range of amounts rather than the single amount of the target sequence. For example, the compositions and conditions are selected to generate a large amount of amplicon 1 and a relatively smaller amount of amplicon 2 (and, optionally, a still smaller amount of amplicon 3, and etc for each amplicon species made to extend the dynamic range of detection) in a single reaction mixture. If the amount of amplicon 1 produced in the amplification reaction exceeds the dynamic range of the detection system, the amounts of amplicon 2 (and/or amplicon 3) produced may be detected instead, as their concentrations fall within the dynamic range of the system. In some embodiments, the number of copies of each amplicon species differs by two, three, four or more orders of magnitude.

The amplicons and amounts thereof are selected to ensure that one or more of the amplicons made in the amplification reaction mixture may be precisely measured in the detection system. From the precise amplicon measurements, the amount of original target nucleic acid sequence present in the test sample is calculated. Overall, then, the system is capable of accurately detecting and quantifying the target nucleic acid sequence over an extended dynamic range. In a preferred embodiment, different amounts of amplification oligomers that target the same strand of the target nucleic acid are used to produce the different amounts of distinguishable amplicons. In some embodiments, the amount of each amplification oligomer differs by at least two orders of magnitude. In some embodiments, the distinguishable amplicons are made from the same target region of the target nucleic acid sequence. In other embodiments, the distinguishable amplicons are made from overlapping target regions. In yet other embodiments, the distinguishable amplicons are made from distinct target regions.

In some embodiments, the starting target amount is determined using one or more equations that include terms containing the concentration of each primer or terms that express the relative relationship among the concentrations of the primers, such as a ratio, that lead to the formation of a distinguishable product. Relevant variables for the calculation include the concentrations of the various amplification oligomers and their amplification efficiencies.

In other embodiments, the methods use primers selected to produce distinguishable amplicons in which the amounts of those primers are chosen to stop amplification of each distinguishable amplicon at a preselected level that cannot exceed the amounts of the relevant primers for that amplicon.

The actual ratios at which the distinguishable amplification oligomer targeting the same strand of a target nucleic acid are present in the reaction will depend upon the inherent dynamic range of the detection system. The ranges of the amounts of amplicon produced by each primer may ideally overlap somewhat to produce an unbroken extended dynamic range unless there are reasons that separate dynamic ranges with a gap between them is desired. For example, if acridinium ester-labeled probes and a luminometer capable of detecting amplicon over a span of 4 logs are used in a system in which two distinguishable products are made, then the ratio of the primers used to make the two distinguishable products should be between 1,000 and 10,000 and, more preferably, about 3000, the midpoint of the logarithmic range between those two extremes.

The methods of the invention may be described according to the following exemplary scheme. Although the scheme is depicted with just two amplification oligomer-amplicon systems, one of skill in the art will recognize that additional amplification oligomer-amplicon-probe systems may be added to create an even broader dynamic range. It is also notable that the schematic below showing the two amplification oligomer-amplicon system is not showing the opposite strand amplification oligomer that works with P1 and P2 to generate A1 and A2. The variables $P_x$, $A_x$, and $C_x$ are defined above.

than $C_{x+1(a)}$ such that the ranges of detection for the probes overlap, creating a continuous dynamic range.

As used herein, the variable $T_1$ refers to the number of copies of target nucleic acid sequence in a test sample. $T_1$ falls within a range from about $T_a$ to $T_b$, wherein the range represents the amount of target nucleic acid sequence that will produce an amount of amplicon that falls within the dynamic detection range of the system. For example, according to the Scheme above, for a given $T_1$, the amounts of Amplification Oligomer 1 ($P_1$) and Amplification Oligomer 2 ($P_2$) are selected such that the resulting amounts Amplicon 1 ($A_1$) and Amplicon 2 ($A_2$) fall within the $C_{1(a)}$ to $C_{2(b)}$ range of detection for the system.

Distinguishable Products Made Using Modified and Unmodified Primers

In one embodiment of the method, the amplification oligomers generate amplicon species that differ one from the other by the presence or absence of a modified nucleobase. In one aspect, the amplification oligomers targeting the same strand of a target nucleic acid differ from one another by having one or more modified nucleobases in the target hybridizing sequence of one amplification oligomer, compared to another. The modified and unmodified amplification oligomers can hybridize to the same sequence on the same strand of a target nucleic acid, yet produce differentiable amplicons based on the incorporation of the modified nucleobase in some of the amplification products. For example, a TMA reaction is run using a single promoter-based amplification oligomer and two primer oligomers, wherein the one of the two primers is an unmodified primer and the other is a modified primer. A modified primer is derived from the sequence of the unmodified primer to contain a distinguishable modification that is incorporated into its amplicon. In a preferred embodiment of the modified primer, one or more of the nucleotides in the unmodified primer are replaced by other nucleotides. In an especially preferred embodiment, the substitution does not substantially alter the ability of the modified primer to anneal to its intended target nucleic acid sequences and promote amplification relative to the unmodified primer. The amplification reaction is then run using the unmodified primer and a small fraction, for example 1/1000, of the modified primer. Thus, the amplification reaction will generate a first amplicon corresponding to the modified primer and a second amplicon Scheme

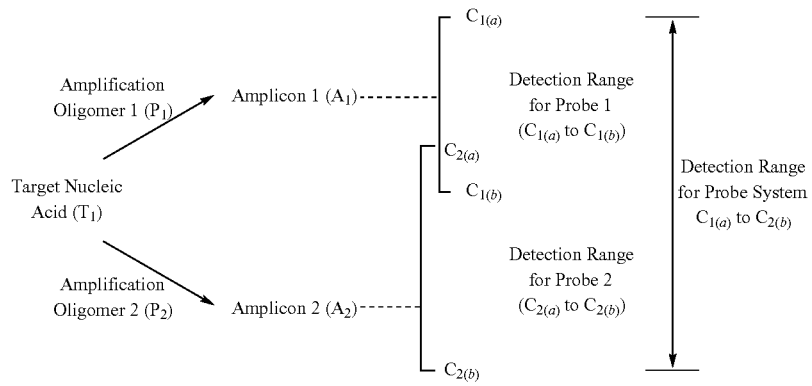

As discussed above, the detection ranges for the individual probes may be discreet (i.e., a gap between the ranges) or overlapping. The scheme above depicts the overlapping variant. Thus, in particular embodiments, each $C_{x(b)}$ is greater corresponding to the unmodified primer. Assuming the modified and unmodified primers are equally efficient, the number of first amplicon molecules with the modified sequence will be about 1/1000 of the number of second amplicon molecules with the unmodified sequence. The amplicon populations are then detected and quantified using two distinguishable probes. One probe detects the second amplicon molecules that contain the unmodified sequence; the other probe detects the first amplicon molecules that contain the modified sequence. If little amplicon is produced due to low initial target levels, only the probe complementary to the unmodified sequence will show significant hybridization because this amplicon is produced in excess over the modified amplicon species. This hybridization should be quantitative over about 3-4 logs. If, however, the amount of amplicon produced in the amplification reaction is much greater, then the probe that is complementary to the unmodified sequence will reach hybridization saturation and signal will be detected with the probe complementary to the modified sequence. The latter signal will also be quantifiable over about 3-4 logs; however, to determine the amount of amplicon generated that signal needs to be multiplied by 1000 (the "ratio factor") since it represents only 1/1000 of the number of amplicon molecules that have been produced in the amplification reaction.

Ideally, the distinguishable products will be produced in amounts equivalent to the ratios of the primers used in their synthesis, those skilled in the art however will recognize that exactly matching amplification efficiencies of different primers may be difficult and expensive. In other preferred embodiments of the invention, the efficiencies of amplification of the distinguishable products are matched to the degree desired and any difference in efficiencies is taken into account when the total amount of amplicon produced is calculated from the amounts of each distinguishable product. In the previous example in which the modified primer was present in 1000-fold smaller amount than the unmodified primer but amplification efficiencies were the same, the amount of modified amplicon was multiplied by 1000. If, however, the efficiency of amplification with the modified primer were to be only 80% of the efficiency of the unmodified primer, then only 0.8 molecules of modified product would be synthesized for each 1000 molecules of unmodified product. In that case, the amount of total amplified product would be calculated by multiplying the signal from the modified product by the ratio factor (1000) and by an "efficiency factor" (expected/actual=1.0/0.8=1.25) to take into account the lower efficiency.

For reactions in which hybridization is measured by the number of relative light units (RLU) produced from a chemiluminescent label, the amount of total amplicon would be calculated as a function of the signal from each probe as follows:

Total amplicon(probe $U$ signal)=
Net $RLU_{probe\ U} \times$(pmoles probe $U/RLU_{probe\ U}$); (1)

Total amplicon(probe $M$ signal)=
Net $RLU_{probe\ M} \times$(pmoles probe $U/RLU_{probe\ M}$)$\times$ratio factor$\times$efficiency factor (2)

where "probe U" and "probe M" target the unmodified and modified amplicons, respectively.

If both calculated values lie within the overlap region of the dynamic range, then in a preferred embodiment they are compared to determine if they are acceptably close to one another. If they do not differ by more than a predetermined acceptable amount, then they are combined to produce the best estimate of the total amplicon amount. In general, the mean value will be determined by summing the two values and dividing by 2.

In general, where the amount of amplicon produced is above the overlap range, the signal from probe M will be used to calculate the total amount of amplicon. In this case, the signal from probe U is expected to be saturated. In the case where the amount of amplicon produced is below the overlap range, the signal from probe U will be used to calculate the total amount of amplicon. In this case, the signal from probe M is expected to be less than the signal from probe U. How much less will depend upon the ratio factor, the efficiency factor, and the specific activities of the two probes as well as the amount of target.

The amount of target nucleic acid sequence in the test sample is then determined in comparison to values of total amplicon produced under the same reaction conditions from a set of standards of known target nucleic acid sequence concentration.

In the example discussed above, two distinguishable products were produced and the amount of target nucleic acid sequence in the test sample was calculated based upon the amounts of each of the two amplicons generated in the amplification reaction. Those skilled in the art will appreciate that further increases in the dynamic range of an assay can be achieved by making additional numbers of distinguishable amplicons in the amplification reaction through the use of additional primers as needed to achieve the desired dynamic range (e.g., $P_3$, $P_4$, etc.). Each new amplicon should be distinguishable from the others and be made in an amount that generates a signal within the range of the detection instrument when it is hybridized to a probe with an appropriate specific activity. The amount of primer used to generate each specific amplicon must result in an amount of product that contributes to the extension of the dynamic range. In particular embodiments, as discussed earlier for the case in which two distinguishable amplicons are used, the amount of product produced from each added primer will fall within a detection range that partially, but not completely, overlaps the detection range for product produced by any of the other primers in order to extend the dynamic range beyond the limits it had without the new primer.

In a preferred embodiment, the specific activities of the probes are similar or identical and the dynamic range is spanned by differences in the amounts of each distinguishable product that is made. However, in other embodiments both the amounts of distinguishable products made and the specific activities of the probes used to detect them may be varied to further expand the dynamic range or simply for convenience. The specific activity of each probe (that is, the amount of signal per molar amount of probe) is a term of the equations given above to calculate the amount of each distinguishable amplicon that is produced. In practice, it may be difficult to achieve similar or identical specific activities when labeling probes; therefore, the ability of the invention to accommodate some variability in specific activity is often of value.

As noted above, the modified primer may contain one or more base substitutions. These may be located at different positions within the primer with intervening unsubstituted bases or they may be clustered together in a single region. A sufficient number of nucleotides may be substituted to form a region that loops out when the primer hybridizes to the target nucleic acid sequence. Any of a large number of modifications is possible so long as they do not substantially alter the efficiency of priming and amplification. By "not substantially alter" is meant that the base substitutions do not change the efficiency of amplification so that the amounts of product produced from them are below the levels needed to span the intended dynamic range in accordance with the teachings herein of the invention or cause the amount of product synthesized from them to be excessively variable under the reaction conditions and with the target nucleic acid sequences and test sample types used. By "excessively variable" is meant that the amount of amplicon produced cannot be held within the desired range of performance needed when the assay is applied for its intended use. In the case of an assay intended for measurement of viral loads in patient blood samples, the coefficient of variation of the assay should generally be no more than about 25% and preferably less than about 10%.

The modified and unmodified amplicons could either be detected using probes that can distinguish between the two forms, or an enzyme that distinguishes the two could be used to help effect discrimination. For example, if the modified base is a methylated base, then a restriction enzyme that does not recognize the methylated sequence might be employed. Alternately, for example, if the modified base is a methylated base, then a restriction enzyme that does recognize the methylated sequence might be employed. Alternatively, the presence of the modified base may cause a different base to be inserted in the amplicon on the next round of replication. In this case, the base could be a deoxyribonucleotide or a ribonucleotide. The modified sequence that is produced could be differentiated from the unmodified sequence using two distinguishable probes that each hybridize to only one of the two forms.

Distinguishable Products Made Using Primers with 5' Unpaired Bases

Another method for providing distinguishable amplicons involves using same direction amplification oligomers with 5' unpaired bases. For example, two primers might each contain one or more originally unpaired bases at or near their 5' termini, wherein the unpaired bases of one amplification oligomer is different from the unpaired bases of the other amplification oligomer. By "originally unpaired" is meant that these bases are not hybridized when the primer anneals to the target nucleic acid sequence in the test sample. Once the primer and its 5' unpaired base is incorporated into an amplicon as the amplification reaction proceeds, then each primer will be completely complementary to those amplicon molecules that are derived from the same primer sequence but will not be completely complementary to those amplicon molecules that were derived from the other primer sequence. These two forms of primer are likely to have similar kinetics with respect to amplification.

Distinguishable Products Made Using Substituted Nucleotides

In another embodiment of the method, one of the nucleotide triphosphates (NTPs) present in the amplification reaction is replaced in part with a modified NTP analog with different hybridization or other recognition characteristics once incorporated into the amplicons. The modified NTPs are present at, for example, about $\frac{1}{1000}$ of the numbers of the unmodified NTPs. As amplicon is produced, the sequence complementary to the detection probe will contain, on average, 1 molecule with the modified base in a particular position instead of the unmodified base per 1000 nucleotides incorporated. The modified base could either be detected using probes that can distinguish between the two forms, or an enzyme that distinguishes the two could be used to help effect discrimination. For example, if the modified base is a methylated base, then a restriction enzyme that does not recognize the methylated sequence might be employed. Alternately, a probe could have a modified nucleotide at a position that is complementary to the modified nucleotide incorporated into a fraction of the amplicons but not complementary to other nucleotides incorporated in that position. Modified nucleotides, as well as enzymatic incorporation of modified nucleotide triphosphates, are known in the art (e.g., *Nucleic Acids Res.* 26(21): 4975-4982 (1998); *J. Am. Chem. Soc.* 122(32): 7621-7632 (2000); *Proc. Natl. Acad. Sci. U.S.A.* 100(8): 4469-4473 (2003); *J. Am. Chem. Soc.* 125(33): 9970-9982 (2003); *J. Am. Chem. Soc.* 126(4): 1102-1109 (2004); *J. Am. Chem. Soc.* 127(43): 15071-15082 (2005)). Alternatively, the presence of the modified base may cause a different base to be inserted in the amplicon on the next round of replication. In this case, the base could be a deoxyribonucleotide or a ribonucleotide. The modified sequence that is produced could be differentiated from the unmodified sequence using two distinguishable probes that each hybridize to only one of the two forms.

Distinguishable DNA and RNA Targets

Certain amplification systems inherently produce different amounts of distinguishable amplicons as part of the amplification process. In one embodiment of the method, differential detection of the final and intermediate products of these amplification reactions is used to extend the dynamic range. For example, in a commonly practiced variant of TMA, the most abundant amplicon is RNA that is complementary to the target nucleic acid. Double-stranded DNA is also produced in much smaller amounts, generally at levels that are about 100- to 1000-fold less. Probes can be made to detect the negative strand RNA amplicon species and either, or both, strands of the DNA amplicon species. Thus, the general principle of the invention, namely the detection of multiple forms of amplicon that are present in substantially different numbers to widen the dynamic range, can be applied provided that the ratio of negative strand RNA amplicon to positive strand DNA amplicon is constant under the conditions used to conduct the TMA reaction. The relative amounts of RNA and double-stranded DNA products that are produced in a TMA reaction can be varied by changing the sequence of the promoter used as described, for example, in *Nucleic Acids Res.* 15(13): 5413-5432 (1987), *Nucleic Acids Res.* 15(21): 8783-8798 (1987), *Nucleic Acids Res.* 20(10): 2517-2524 (1992), *Nucleic Acids Res.* 24(18): 3659-3660 (1996), *Pac. Symp. Biocomput.* 15: 433-443 (2010), *Biochemistry* 41(11): 3586-3595 (2002) and *J. Biol. Chem.* 280(49): 40707-40713 (2005). Since transcription efficiency is also dependent upon the concentration of ribonucleotides, it can be varied by changing both the total concentration of these reaction components as well as the relative amounts of each of the four ribonucleotides (*Science* 278(5346): 2092-2097 (1997); *J. Mol. Biol.* 281(5): 777-792 (1998)). The activity of reverse transcriptase in copying both the RNA and DNA templates in the reaction can be varied similarly by altering the concentrations of deoxyribonucleotides as well as the relative amounts of each of the four deoxyribonucleotides. Reducing the concentrations of all four deoxyribonucleotides will slow the reverse transcriptase DNA polymerase reaction relative to the RNA polymerase reaction. For specific target regions, analysis of the percentages of each base in the DNA and RNA components of the reaction may be used to select concentrations of each base that will increase or decrease the rate of synthesis of either the transcribed RNA or the double-stranded DNA. For example, if an amplicon contains a high percentage of cytosine nucleotides relative to another amplicon, lowering the concentration of cytosine in the reaction mixture can be used to slow synthesis of that particular amplicon. Alterations in other reaction parameters such as those described, for example, in U.S. Pat. Nos. 5,705,365 and 5,710,029 can also be used to differentially affect the ratio of synthesis of transcribed RNA and double-stranded DNA products. Detection of the positive strand DNA is complicated by the possible presence of competing negative strand RNA amplicon in substantially larger amounts; therefore, the negative strand DNA may be a preferable target. Since the DNA amplicons in TMA contain the promoter sequence, modifications of the promoter-primer that are readily detectable may be preferred. A probe may be used to confirm the presence of the promoter region, the adjacent primer region, and a portion of the desired target sequence in the amplicon. These three sequences will only be present in tandem in DNA intermediates in the reaction.

Likewise, in another commonly practiced variant of TMA, single-primer TMA described in U.S. Pat. No. 7,374,885, the most abundant amplicon is RNA that is the same sense as the target nucleic acid. Negative strand DNA is also produced in much smaller amounts. Probes can be made to detect the positive strand RNA and the negative strand DNA to widen the dynamic range.

Distinguishable Products Based Upon Differential Target Capture

In another embodiment of the method, suitable target capture oligonucleotides are made that are complementary or partially complementary to one of the primer sites and extend into a part of the desired probe-binding site. These target capture oligomers are able to serve as both target capture oligonucleotides and same direction amplification oligomers. In a small percentage of these target capture oligonucleotides, the sequence is altered so that a distinguishable amplicon is produced in the probe-binding region in the same way as described above for a primer that does not also function in target capture. After target capture and washing to remove unwanted materials, including unbound capture probe, the remaining components of the amplification reaction are added and the amplification process permitted to occur. The initial DNA:RNA (original target RNA) or DNA:DNA (original target DNA) duplexes that are generated by extension of the target capture oligonucleotides will contain the modified sequence in a known proportion of the molecules. Assuming that the two target sequences amplify at a consistent ratio thereafter, probes that distinguish between the two species can be used to quantitate the original target over a wider range as discussed above.

Distinguishable Products Made Using Semi-Nested Primers

In yet another embodiment of the method, semi-nested primers are provided in an amplification reaction at different concentrations. For example, the at least two primers comprise a first inner primer and a second outer primer. The first inner and second outer primers are both forward primers or are both reverse primers. The reaction mixture may further comprise a single promoter-based amplification oligomer that operates in a direction opposite that of the first inner and second outer primers. Thus, the at least two amplicons produced from these primers comprise a first amplicon produced from the first inner primer and a second amplicon produced from the second outer primer. The first inner primer is provided at a low concentration while the second outer, reverse primer is provided at a higher concentration. When target nucleic acid sequences are included in the reactions, shorter amplicons are synthesized from the promoter-based amplification oligomer and first inner primer while longer amplicons are synthesized from the promoter-based amplification oligomer and the second outer primer. The longer amplicons can serve as templates for further synthesis of longer or shorter amplicons. By choosing different reverse primer concentrations, differential amounts of the longer and shorter amplicons are synthesized in a single reaction. The shorter amplicons include sequences that are in common with the longer amplicons. The longer amplicons include sequences that are in common with the shorter amplicons and others that are different than those in the shorter amplicons. Because differential amounts of longer and shorter amplicons are synthesized in a single reaction, quantifying the amounts of longer and shorter amplicons can provide two overlapping ranges, effectively extending the dynamic range of detection. Quantification of different amounts of amplicons can be further brought into dynamic range of a detection system by adjustment of probe specific activity.

Alternate configurations of semi-nested amplification oligomers at different concentrations are possible in an amplification reaction at different concentrations. For example, opposite a single reverse primer, an inner forward primer is provided at a low concentration while an outer forward primer is provided at a higher concentration. When target nucleic acid sequences are included in the reactions, shorter amplicons are synthesized from the reverse primer and inner forward primer while longer amplicons are synthesized from the reverse primer and the outer forward primer. The longer amplicons can serve as templates for further synthesis of longer or shorter amplicons. From this process, differential amounts of longer and shorter amplicons are synthesized in a single reaction. Choosing different forward primer concentrations can vary these differential amounts of amplicons. The shorter amplicons include sequences that are in common with the longer amplicons. The longer amplicons include sequences that are in common with the shorter amplicons and others that are different than those in the shorter amplicons. Since differential amounts of longer and shorter amplicons are synthesized in a single reaction, quantifying the amounts of longer and shorter amplicons can provide two overlapping ranges, effectively extending the dynamic range of detection. Quantification of different amounts of amplicons can be further brought into dynamic range of a detection system by adjustment of probe specific activity.

The following examples are provided to further illustrate the present method and are not intended to limit to it.

EXAMPLES

Amplification Compositions for Examples 1-3 and 5

0.2 μm filtered water ($H_2O$)

4× Amplification Reagent: 160 mM tris(hydroxymethyl) aminomethane (Tris base), 100 mM $MgCl_2$, 70 mM KCl, 16 mM each of rATP, rCTP, rGTP and rUTP, 4 mM each of dATP, dCTP, dGTP and dTTP, 20% polyvinylpyrrolidone, 0.3% ethyl alcohol, 0.02% methyl paraben, 0.01% propyl paraben, pH 7.5

4× Enzyme Reagent: 8 mM N-(2-hydroxyethyl)piperazine-N'-(2-ethanesulfonic acid) (HEPES free acid), 140 mM Tris base, 70 mM KCl, 50 mM N-acetyl-L-cysteine, 1.04 mM ethylenediaminetetraacetic acid (EDTA), 0.04 mM zinc acetate, 10% TRITON X®-102, 80 mM trehalose, 20% glycerol, 80 units/μL Moloney murine leukemia virus (MMLV) reverse transcriptase (RT), 80 units/μL T7 RNA polymerase (T7RNAP), pH 8.0

Silicone Oil Reagent: polydimethylsiloxane, trimethylsiloxy terminated

Primers:

```
4X (Promoter primer or Pr-primer (300 nM in water)
                                           (SEQ ID NO: 1)
5'-AATTTAATACGACTCACTATAGGGAGA
GTTTGTATGTCTGTTGCTATTAT-3'

4X Primer 1 (15 nM in water)
                                           (SEQ ID NO: 2)
5'-ACAGCAGTACAAATGGCAG-3'

4X Primer 2 (285 nM in water)
                                           (SEQ ID NO: 3)
5'-ATTCCCTACAATCCCCAAAGTCAA-3'
```

Target sequence-RNA, 1,016 nt, in vitro transcript (IVT); the 51 nt from the 5' part of the IVT are from the T7 promoter and cloning vector; the remaining 965 nt include the 3' part of the HIV-1 subtype B pol gene, possibly a little of the 5' part of the subsequent gene depending on who assigned the division of genes in water (SEQ ID NO: 4)
5'-GGGAGACAAGCUUGCAUGCCUGCAGGUCGACUCUAGAGGAUCCCCG

GGUACCAGCACACAAAGGAAUUGGAGGAAAUGAACAAGUAGAUAAAUUA

GUCAGUGCUGGAAUCAGGAAAAUACUAUUUUUAGAUGGAAUAGAUAAGG

CCCAAGAUGAACAUGAGAAAUAUCACAGUAAUUGGAGAGCAAUGGCUAG

UGAUUUUAACCUGCCACCUGUAGUAGCAAAAGAAAUAGUAGCCAGCUGU

GAUAAAUGUCAGCUAAAAGGAGAAGCCAUGCAUGGACAAGUAGACUGUA

GUCCAGGAAUAUGGCAACUAGAUUGUACACAUUUAGAAGGAAAAGUUAU

CCUGGUAGCAGUUCAUGUAGCCAGUGGAUAUAUAGAAGCAGAAGUUAUU

CCAGCAGAAACAGGGCAGGAAACAGCAUAUUUUCUUUUAAAAUUAGCAG

GAAGAUGGCCAGUAAAAACAAUACAUCAGACAAUGGCAGCAAUUUCAC

CAGUGCUACGGUUAAGGCCGCCUGUUGGUGGGCGGGAAUCAAGCAGGAA

UUUGGAAUUCCCUACAAUCCCCAAAGUCAAGGAGUAGUAGAAUCUAUGA

AUAAAGAAUUAAAGAAAAUUAUAGGACAGGUAAGAGAUCAGGCUGAACA

UCUUAAGACAGCAGUACAAAUGGCAGUAUUCAUCCACAAUUUUAAAAGA

AAAGGGGGGAUUGGGGGGUACAGUGCAGGGGAAAGAAUAGUAGACAUAA

UAGCAACAGACAUACAAACUAAAGAAUUACAAAAACAAAUUACAAAAAU

UCAAAAUUUUCGGGUUUAUUACAGGGACAGCAGAAAUCCACUUUGGAAA

GGACCAGCAAAGCUCCUCUGGAAAGGUGAAGGGGCAGUAGUAAUACAAG

AUAAUAGUGACAUAAAAGUAGUGCCAAGAAGAAAAGCAAAGAUCAUUAG

GGAUUAUGGAAAACAGAUGGCAGGUGAUGAUUGUGUGGCAAGUAGACAG

GAUGAGGAUUAGAACAUGGAAAAGUUUAGUAAAACACCA-3'

Detection Compositions for Examples 1-3 and 5
  Hybridization Reagent: 100 mM succinic acid, 2% (w/v) lithium lauryl sulfate (LLS), 230 mM LiOH, 15 mM Aldrithiol-2, 1.2 M LiCl, 20 mM ethylene glycol-bis(2-aminoethylether)-N,N,N',N'-tetraacetic acid (EGTA), 20 mM EDTA, 3% (v/v) ethyl alcohol, pH 4.7
  Hybridization Diluent: 0.1% (w/v) LLS, 10 mM succinic acid, pH 5
  Alkaline Reagent: 600 mM boric acid, 182 mM NaOH, 1% TRITON X®-100, pH 8.5
  TMA Separation Suspension Reagent: 0.25 µg/µL magnetic particles (BioMag M4100), 0.2 mM EDTA, 0.08% (w/v) LLS, 8 mM succinic acid, pH 5
  Separation Reagent: 1.25 µg/µL magnetic particles (BioMag M4100), 1 mM EDTA
  Read Reagent: 125 mM LiOH, 1.5 mM EGTA, 1.5 mM EDTA, 95 mM succinic acid, 8.5% (w/v) LLS, pH 5.2
  Detection Reagents
    Detection Reagent 1: 32 mM $H_2O_2$, 1 mM $HNO_3$
    Detection Reagent 2: 1.5 M NaOH
    Detection Reagent 3: 240 mM $H_2O_2$, 1 mM $HNO_3$
    Detection Reagent 4: 2 M Tris base, pH 9.0 with HCl
    Detection Reagent 5: 1 mM $HNO_3$ Probes:

```
acridinium ester (AE)-labeled linear
oligonucleotide probe 1
                                       (SEQ ID NO: 5)
5'-CCACAAUUUUAAAAGAAAAGGG-3'

AE-labeled linear oligonucleotide probe 2
                                       (SEQ ID NO: 6)
5'-AGAAAAUUAUAGGACAGGUAAG-3' unlabeled oligonucleotide probe 3
                                       (SEQ ID NO: 5)
5'-CCACAAUUUUAAAAGAAAAGGG-3' unlabeled oligonucleotide probe 4
                                       (SEQ ID NO: 6)
5'-AGAAAAUUAUAGGACAGGUAAG-3'

AE-labeled, Hybridization Induced
Chemiluminescent Signal (HICS) probe 5 with a 5'-
AE and a 3'-[4-(dimethylamino)azobenzene-4'-
carboxylic acid] (dabcyl) moiety
                                       (SEQ ID NO: 7)
5'-C6amine(LiAE)-CUCGUCCACAAUUUUAAAAGAAAAGGGACGAG-
D-3'

AE-labeled, wavelength-shifted Hybridization
Induced Chemiluminescent Signal (wsHICS) probe
6 with a 5'-tetramethylrhodamine (TAMRA), 5'-
penultimate AE and a 3'-dabcyl moiety
                                       (SEQ ID NO: 8)
5'-TAMRA-rxl(LiAE)-CCUCUAGAAAAUUAUAGGACAGGUAAGAGA
GG-D-3'
```

Amplification Methods for Examples

Replicate TMA reactions were performed in Examples 1-3 and 5 as follows: 25 µL volumes each of 4× Amplification Reagent, primers in water, and RNA transcripts in water plus 100 µL volumes of Silicone Oil Reagent were mixed and incubated at 60° C. for 10 minutes then at 42° C. for 5 minutes; 25 µL volumes of 4× Enzyme Reagent were added to the solutions, the solutions were mixed and then incubated at 42° C. for 90 minutes. The relative placement of the Pr-primer and Primers 1 and 2 on the RNA transcript and the resulting amplicons are shown diagrammatically in FIGS. 1 and 4. Because different concentrations of Primers 1 and 2 were used, different amounts of the respective amplicons and probe binding regions were synthesized in a single reaction.

Example 1

Quantitative Detection of Amplicons with AE Probes Over a Dynamic Range in Separate Reaction Chambers This example demonstrates quantitative detection of amplicons over a range of $10^3$ to $10^9$ copies of target nucleic acid in separate reaction tubes.

At the completion of the TMA amplification reactions, 100 µL volumes of probes in Hybridization Reagent were added to the amplification reaction mixtures, which were mixed and incubated at 60° C. for 15 minutes to allow hybridization of probes specific for complementary sequences in the synthesized amplicons. The probes used were: (a) AE-labeled probe of SEQ ID NO:5 (1 nM) plus unlabeled probe of SEQ ID NO:5 (50 nM), which was used to attenuate the specific activity of the labeled probe; or (b) AE-labeled probe of SEQ ID NO:6 (1 nM) plus unlabeled probe of SEQ ID NO:6 (200 nM), which was used to attenuate the specific activity of the labeled probe. The relative placement of the probes on the distinguishable amplicons is shown diagrammatically in FIG.

1. In this example, the AE-labeled probe of SEQ ID NO:5 is able to detect both amplicons, whereas the AE-labeled probe of SEQ ID NO:6 is only able to detect the longer amplicon.

The initial specific activities for the AE-labeled probes of SEQ ID NO:5 and SEQ ID NO:6 were about $1.1 \times 10^8$ and $1.6 \times 10^8$ RLU/pmol, respectively. The specific activities were adjusted by adding various amounts of unlabeled oligonucleotides of the same sequence as the labeled probe to balance the dynamic range of the probes and the amplicon output. The amount of amplicon produced by the end of the amplification reaction was empirically determined by titrating each detection region with its respective probe plus increasing amounts of unlabeled probe until the highest amount of amplicon output was slightly less than the amount of total probe. For the probe of SEQ ID NO:6, 20 pmol total probe/100 μL Hybridization Reagent (200 nM with specific activity=$8 \times 10^5$ RLU/pmol) was needed to exceed amplicon from $10^9$ copies input. For probe of SEQ ID NO:5, 5 pmol total probe/100 μL Hybridization Reagent (50 nM with specific activity=$2.2 \times 10^6$ RLU/pmol) was needed to exceed amplicon from $10^5$ copies input.

At the completion of the hybridization reactions, 300 μL volumes of Alkaline Reagent were added to the hybridization reactions, and the resulting mixtures were incubated at 60° C. for 20 minutes to selectively hydrolyze AE-labeled probes that were not hybridized to complementary amplicons.

Chemiluminescence from these reactions was initiated in a GEN-PROBE® LEADER® HC+ Luminometer with addition of 200 μL Detection Reagent 1, a two second pause prior to addition of 200 μL Detection Reagent 2, a 0.04 second pause, then acquisition of 50×0.04 second intervals with no delays between intervals. The chemiluminescent output in relative light units (RLUs) from these intervals was summed and the mean values from replicates was calculated (Tables 1 and 2).

TABLE 1

| 1 nM AE-labeled probe of SEQ ID NO: 5 + 50 nM unlabeled probe of SEQ ID NO: 5 | | | |
| --- | --- | --- | --- |
| copies input | mean RLU | mean RLU - bkgd | specific activity-adjusted, mean RLU - bkgd |
| 0 | 4,677 | | |
| $10^2$ | 5,625 | 948 | 47,388 |
| $10^3$ | 13,639 | 8,962 | 448,100 |
| $10^4$ | 64,087 | 59,410 | 2,970,500 |
| $10^5$ | 679,369 | 674,691 | 33,734,563 |
| $10^6$ | 1,508,029 | 1,503,351 | 75,167,563 |
| $10^7$ | 1,606,846 | 1,602,169 | 80,108,438 |
| $10^8$ | 1,645,605 | 1,640,928 | 82,046,375 |
| $10^9$ | 1,715,148 | 1,710,471 | 85,523,538 |

TABLE 2

| 1 nM AE-labeled probe of SEQ ID NO: 6 + 200 nM unlabeled probe of SEQ ID NO: 6 | | | | |
| --- | --- | --- | --- | --- |
| copies input | mean RLU | mean RLU - bkgd | specific activity-adjusted, mean RLU - bkgd | specific activity-adjusted, mean RLU - bkgd, x k = 46.6 |
| 0 | 6,963 | | | |
| $10^2$ | 6,667 | | | |
| $10^3$ | 6,859 | | | |
| $10^4$ | 7,912 | 949 | 189,750 | 8,842,350 |
| $10^5$ | 10,583 | 3,621 | 724,100 | 33,743,060 |

TABLE 2-continued

| 1 nM AE-labeled probe of SEQ ID NO: 6 + 200 nM unlabeled probe of SEQ ID NO: 6 | | | | |
| --- | --- | --- | --- | --- |
| copies input | mean RLU | mean RLU - bkgd | specific activity-adjusted, mean RLU - bkgd | specific activity-adjusted, mean RLU - bkgd, x k = 46.6 |
| $10^6$ | 34,004 | 27,041 | 5,408,150 | 252,019,790 |
| $10^7$ | 180,227 | 173,264 | 34,652,800 | 1,614,820,480 |
| $10^8$ | 956,357 | 1,496,352 | 299,270,400 | 13,946,000,640 |
| $10^9$ | 7,175,753 | 7,168,790 | 1,433,757,950 | 66,813,120,470 |

The mean RLU from the zero RNA transcript input (first entry in each table) was used as the background ("bkgd") measurement and was subtracted from the results of experiments containing $10^2$, $10^3$, $10^4$, $10^5$, $10^6$, $10^7$, $10^8$ and $10^9$ copies RNA transcripts input (mean RLU minus bkgd). The mean background-subtracted values (mean RLU-bkgd) were adjusted to account for the specific activity of the linear AE-labeled probes by multiplying by the fold excess of the linear probes without AE, resulting in specific activity-adjusted, mean background-subtracted values (specific activity-adjusted, mean RLU-bkgd). The specific activity-adjusted, mean background-subtracted values for the two probes measured from separate tubes were added, leading to summed specific activity-adjusted, mean background-subtracted values (Table 3, specific activity-adjusted, mean RLU-bkgd).

TABLE 3

| Sum of Tables 1 & 2 | | |
| --- | --- | --- |
| copies input | specific activity-adjusted, mean RLU - bkgd | specific activity-adjusted, mean RLU - bkgd, x k = 46.6 |
| 0 | | |
| $10^2$ | 47,388 | 47,388 |
| $10^3$ | 448,100 | 448,100 |
| $10^4$ | 3,160,250 | 11,812,850 |
| $10^5$ | 34,458,663 | 67,477,623 |
| $10^6$ | 80,575,713 | 327,187,353 |
| $10^7$ | 114,761,238 | 1,694,928,918 |
| $10^8$ | 381,316,755 | 14,028,047,015 |
| $10^9$ | 1,519,281,488 | 66,898,644,008 |

Figure 3:
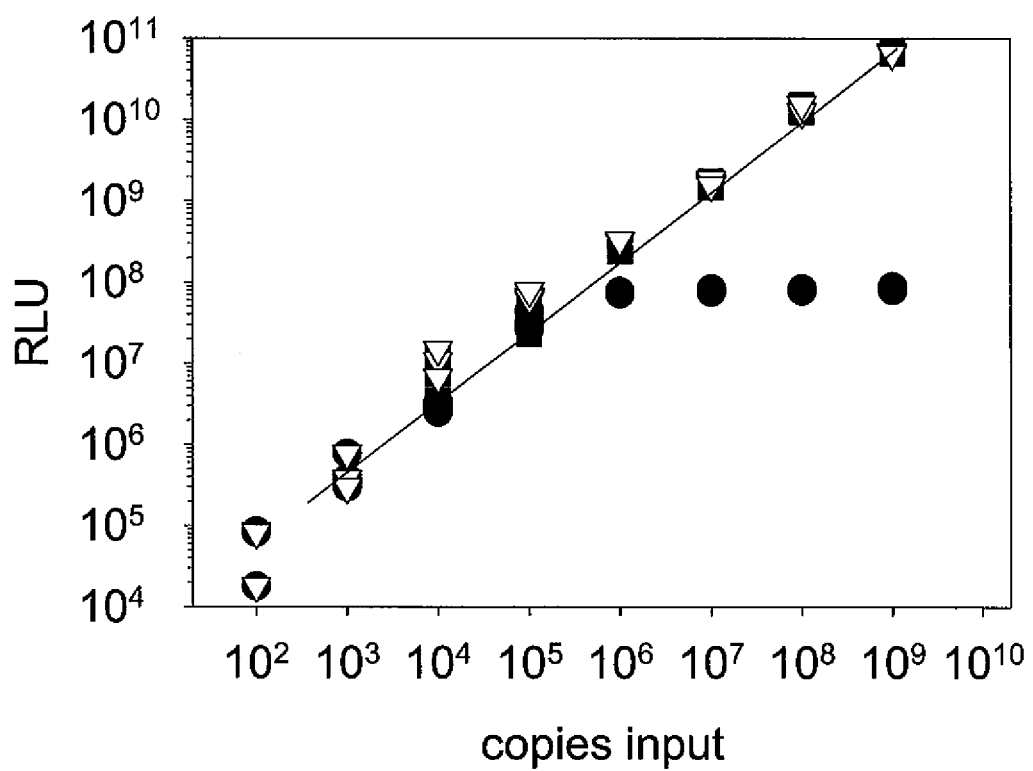
FIG. 3 is a graph that shows the mean, background-subtracted, specific activity-adjusted signal output (y-axis, reported across a range of about $10^4$ to about $10^{11}$ RLU) detected by using linear AE-labeled probes hybridized to amplicons of target RNA across a range of $10^2$ to $10^9$ input target RNA copies (x-axis). In this Figure, values obtained in Example 1 for the reactions of labeled and unlabeled probes of SEQ ID NO:6 have been multiplied by a factor "k" of 46.6 (results shown as black squares) to allow direct visual comparison of these results to those obtained from the reaction of labeled and unlabeled probes of SEQ ID NO:5 (black circles). The sum of the two sets of detection signals (white triangles) demonstrate that the reaction system creates a continuous linear dynamic range of at least $10^3$ to $10^9$ input copies.

Each of the replicates for the specific activity-adjusted, mean background-subtracted values for each probe and for the summed probe values is shown in FIG. 2. Chemiluminescence from AE-labeled probe of SEQ ID NO:5 plus unlabeled probe of SEQ ID NO:5 demonstrated a linear increase in RLU from about $10^3$ to $10^5$ copies per reaction of RNA transcript input. Chemiluminescence from AE-labeled probe of SEQ ID NO:6 plus unlabeled probe of SEQ ID NO:6 demonstrated a linear increase in RLU from about $10^5$ to $10^9$ copies per reaction of RNA transcript input. The slopes of responses from the two sets of probes were about collinear. Their summed RLU values demonstrate two discontinuous linear increases in RLU from about $10^3$ to $10^5$ copies per reaction and from about $10^4$ to $10^9$ copies per reaction. However, transforming the RLU values from AE-labeled probe of SEQ ID NO:6 plus unlabeled probe of SEQ ID NO:6 by a multiplying by a constant (k), in this case 46.6, demonstrated the continuous linear dynamic range of detection from these two sets of probes from about $10^3$ to $10^9$ copies per reaction (Tables 2 and 3, FIG. 3). The constant (k) is a visualization tool used to adjust the slopes of both linear regression to a common x-intercept, but is not necessary for the quantification of the two regions of amplicons. The constant (k) was calculated by dividing the mean RLU value from a first probe by the mean RLU value from a second probe taken at a target input concentration in which RLU values from both probes are part of the same linear regression. The value varies depending on at least the primer concentrations, probe specific activities, and amplification efficiencies.

Example 2

Quantitative Detection of Amplicons with AE-HICS Probes Over a Dynamic Range in the Same Reaction Chamber This example demonstrates an embodiment that provides quantitative detection of amplicons over a dynamic range from $10^6$ to $10^{10}$ copies of target input in the same reaction chamber.

At the completion of TMA reactions, 100 µL volumes of Hybridization Reagent were added, mixed and incubated at room temperature for 20 minutes. TMA Separation Suspension Reagent (250 µL) was added, mixed and incubated at 60° C. for 10 minutes. The tubes containing the above solutions were placed on a magnetic separation rack at room temperature for 5 minutes, the liquid phase was removed, 100 µL of probes in half-strength Hybridization Reagent were added, and the resulting mixtures were incubated at 60° C. for 30 minutes and at room temperature for 5 minutes. The probes used were (a) 10 nM self-quenching AE-labeled HICS probe of SEQ ID NO:7, (b) 100 nM self-quenching, wavelength-shifted AE-labeled wsHICS probe of SEQ ID NO:8, or (c) both probes at the concentrations indicated in (a) and (b). The relative placement of the probes on the distinguishable amplicons is shown diagrammatically in FIG. 4. Labeled probe of SEQ ID NO:7 detects both amplicons, whereas the labeled probe of SEQ ID NO:8 detects only the longer amplicons.

At the completion of the hybridization reactions, 100 µL volumes of Hybridization Diluent were added to the hybridization reactions, and the resulting mixtures were incubated at 60° C. for 10 minutes. The tubes containing the above solutions were placed on a magnetic separation rack at room temperature for 5 minutes, the liquid phase was removed, and 100 µL volumes of Read Reagent were added and mixed.

Chemiluminescence from these reactions was initiated in a modified luminometer equipped with two high-count photomultiplier tube modules (PMT; 28 mm diameter, head-on, bialkali cathode; Hamamatsu Photonics, Hamamatsu City, Japan) on opposite sides of and directed towards a light-tight detection chamber fitted with injector tubing from two reagent pumps. Filters (25.4 mm diameter; 430AF60 from Omega Optical (Brattleboro, Vt.) and OG550 from Newport Corp. (Franklin, Mass.)) were fitted between the PMTs and the detection chamber to allow discrimination of emissions from the two probes. Similar multiple wavelength luminometers are known in the art (e.g., U.S. Pat. No. 5,447,687 and *Clin. Chem.* 29(9), 1604-1608 (1983)). Chemiluminescence from these reactions was initiated by addition of 200 µL Detection Reagent 3, a two second pause prior to addition of 200 µL Detection Reagent 4, then simultaneous acquisition of 100×0.4 second intervals of time-resolved chemiluminescent data from both channels with no delays between intervals.

The chemiluminescent output in RLUs from these intervals is reported in Tables 4 and 5. The last column in each table reflects the sum of the individual results.

TABLE 4

| PMT1 copies input | rep | 10 nM AE-labeled probe of SEQ ID NO: 7 | | 100 nM AE-labeled probe of SEQ ID NO: 8 | | 10 nM AE-labeled probe of SEQ ID NO: 7 100 nM AE-labeled probe of SEQ ID NO: 8 | |
|---|---|---|---|---|---|---|---|
| | | RLU | RLU-bkgd | RLU | RLU-bkgd | RLU | RLU-bkgd |
| 0 | 1 | 377 | | 1,176 | | 1,487 | |
| 0 | 2 | 390 | | 1,117 | | 1,498 | |
| $10^2$ | 1 | 465 | 82 | | | 1,544 | 52 |
| $10^2$ | 2 | 622 | 239 | | | 2,161 | 669 |
| $10^3$ | 1 | 526 | 143 | | | 1,868 | 376 |
| $10^3$ | 2 | 669 | 286 | | | 1,632 | 140 |
| $10^4$ | 1 | 641 | 258 | | | 1,529 | 37 |
| $10^4$ | 2 | 705 | 322 | | | 1,823 | 331 |
| $10^5$ | 1 | 660 | 277 | 1,405 | 259 | 1,631 | 139 |
| $10^5$ | 2 | 836 | 453 | 1,165 | 19 | 1,783 | 291 |
| $10^6$ | 1 | 1,128 | 745 | 1,072 | −75 | 1,974 | 482 |
| $10^6$ | 2 | 1,389 | 1,006 | 1,154 | 8 | 2,160 | 668 |
| $10^7$ | 1 | 2,973 | 2,590 | 1,448 | 302 | 3,376 | 1,884 |
| $10^7$ | 2 | 2,667 | 2,284 | 1,312 | 166 | 3,741 | 2,249 |
| $10^8$ | 1 | | | 1,376 | 230 | 7,624 | 6,132 |
| $10^8$ | 2 | | | 1,423 | 277 | 8,208 | 6,716 |
| $10^9$ | 1 | | | 2,027 | 881 | 11,281 | 9,789 |
| $10^9$ | 2 | | | 2,343 | 1,197 | 13,897 | 12,405 |
| $10^{10}$ | 1 | | | 5,496 | 4,350 | 19,736 | 18,244 |
| $10^{10}$ | 2 | | | 5,726 | 4,580 | 20,159 | 18,667 |

TABLE 5

| PMT2 copies input | rep | 10 nM AE-labeled probe of SEQ ID NO: 7 | | 100 nM AE-labeled probe of SEQ ID NO: 8 | | 10 nM AE-labeled probe of SEQ ID NO: 7 100 nM AE-labeled probe of SEQ ID NO: 8 | |
|---|---|---|---|---|---|---|---|
| | | RLU | RLU-bkgd | RLU | RLU-bkgd | RLU | RLU-bkgd |
| 0 | 1 | 314 | | 16,147 | | 16,464 | |
| 0 | 2 | 767 | | 15,321 | | 16,006 | |
| $10^2$ | 1 | 633 | 93 | | | 18,291 | 2,056 |
| $10^2$ | 2 | 642 | 102 | | | 26,609 | 10,374 |
| $10^3$ | 1 | 614 | 74 | | | 19,620 | 3,385 |
| $10^3$ | 2 | 630 | 90 | | | 18,419 | 2,184 |
| $10^4$ | 1 | 613 | 73 | | | 17,711 | 1,476 |
| $10^4$ | 2 | 629 | 89 | | | 21,987 | 5,752 |
| $10^5$ | 1 | 642 | 102 | 21,097 | 5,363 | 17,883 | 1,648 |
| $10^5$ | 2 | 629 | 89 | 16,355 | 621 | 19,147 | 2,912 |
| $10^6$ | 1 | 689 | 149 | 15,224 | −510 | 14,504 | −1731 |
| $10^6$ | 2 | 642 | 102 | 17,258 | 1,524 | 16,087 | −148 |
| $10^7$ | 1 | 702 | 162 | 24,409 | 8,675 | 20,506 | 4,271 |
| $10^7$ | 2 | 719 | 179 | 20,781 | 5,047 | 24,571 | 8,336 |
| $10^8$ | 1 | | | 28,655 | 12,921 | 39,411 | 23,176 |
| $10^8$ | 2 | | | 26,900 | 11,166 | 49,451 | 33,216 |
| $10^9$ | 1 | | | 70,691 | 54,957 | 92,458 | 76,223 |
| $10^9$ | 2 | | | 80,236 | 64,502 | 118,738 | 102,503 |
| $10^{10}$ | 1 | | | 283,009 | 267,275 | 273,576 | 257,341 |
| $10^{10}$ | 2 | | | 308,126 | 292,392 | 309,765 | 293,530 |

Figure 5:
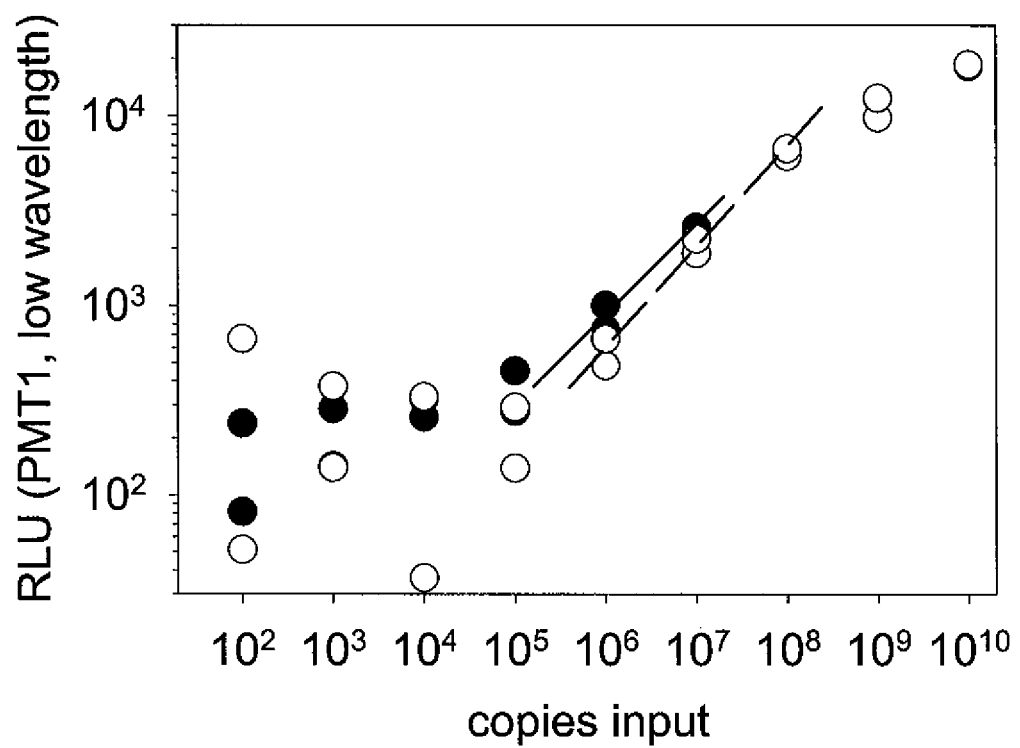
FIG. 5 is a graph showing the mean, background-subtracted PMT 1 (low wavelength) RLU output from reactions of self-quenching AE probes with amplicons of RNA transcripts at the indicated range of copy inputs as obtained in Example 2 for (a) 10 nM labeled probe of SEQ ID NO:7 (black circles) and (b) 10 nM labeled probe of SEQ ID NO:7 plus 100 nM labeled probe of SEQ ID NO:8 (white circles).
Figure 6:
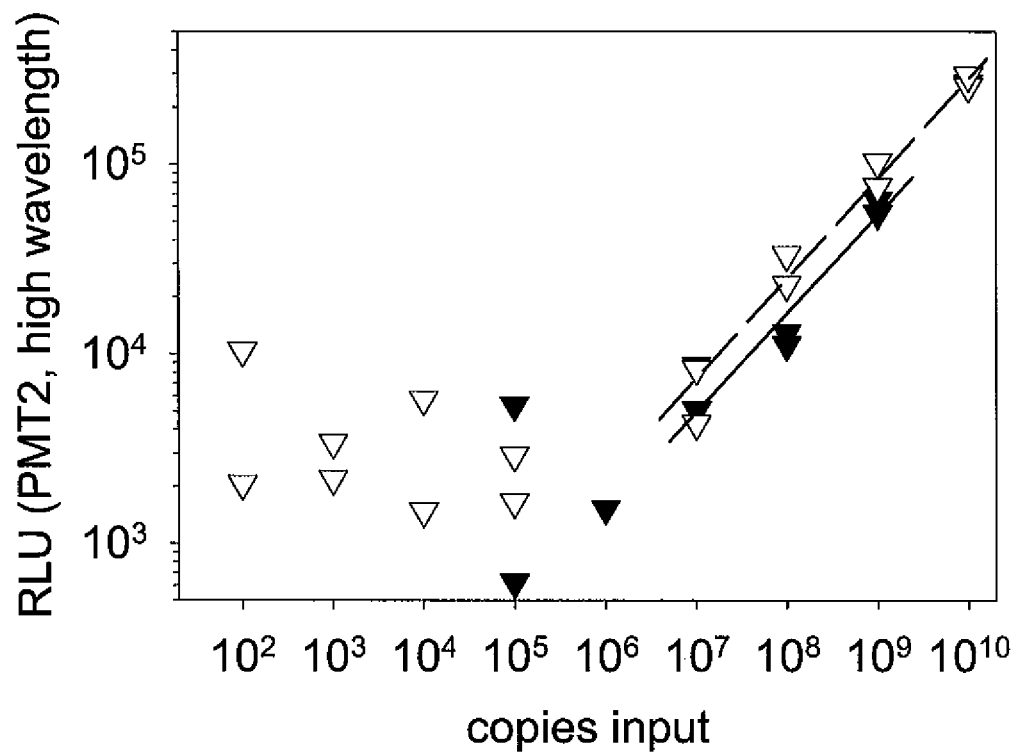
FIG. 6 is a graph showing the mean background-subtracted PMT 2 (high wavelength) RLU output from reactions of self-quenching AE probes with amplicons of RNA transcripts at the indicated range of copy inputs as obtained in Example 2. Results are shown for (a) 100 nM labeled probe of SEQ ID NO:8 (black triangles) and (b) 100 nM labeled probe of SEQ ID NO:8 plus 10 nM labeled probe of SEQ ID NO:7 (white triangles).

The mean RLU from the zero RNA transcript input (first entry in each table) was used as the background ("bkgd")

measurement and was subtracted from the results of experiments containing (a) $10^2$, $10^3$, $10^4$, $10^5$, $10^6$ and $10^7$ copies RNA transcripts input for AE-labeled probe of SEQ ID NO:7, (b) $10^5$, $10^6$, $10^7$, $10^8$, $10^9$ and $10^{10}$ copies RNA transcripts input for AE-labeled probe of SEQ ID NO:8, or (c) $10^2$, $10^3$, $10^4$, $10^5$, $10^6$, $10^7$, $10^8$, $10^9$ and $10^{10}$ copies RNA transcripts input for both probes (Tables 4 and 5, FIGS. 5 and 6).

FIG. 5 demonstrates that low wavelength RLU (captured by filtered PMT1) response from AE-labeled probe of SEQ ID NO:7 corresponds linearly from at least about $10^6$ to $10^7$ copies per reaction of RNA transcript input and that this response is very similar when the probe was used alone or in concert with AE-labeled probe of SEQ ID NO:8.

FIG. 6 demonstrates that high wavelength RLU (captured by filtered PMT2) response from AE-labeled probe of SEQ ID NO:8 corresponds linearly from at least about $10^7$ to $10^9$ copies per reaction of RNA transcript input and that this response is very similar whether the probe was used alone or in concert with AE-labeled probe of SEQ ID NO:7.

Figure 7:
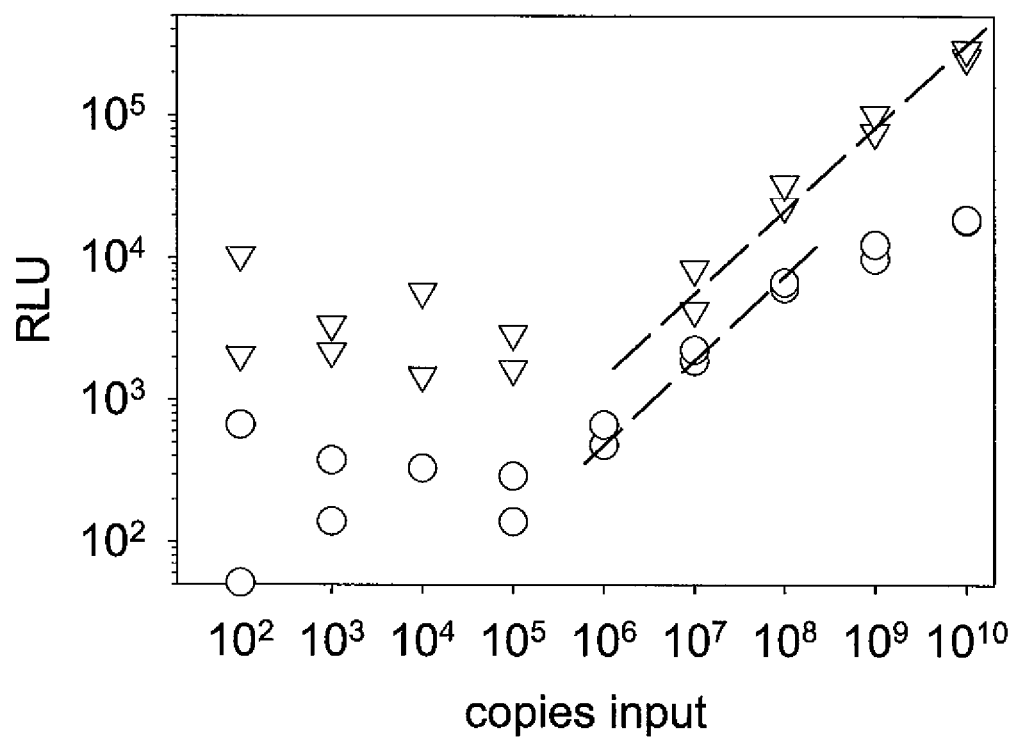
FIG. 7 is a graph depicting the mean, background-subtracted RLU output from the reactions of self-quenching AE probes with amplicons of RNA transcripts at the indicated range of copy inputs as obtained in Example 2. Results shown are (a) PMT 1 RLU for 10 nM labeled probe of SEQ ID NO:7 plus 100 nM labeled probe of SEQ ID NO:8 (white circles) and (b) PMT 2 RLU for 10 nM labeled probe of SEQ ID NO:7 plus 100 nM labeled probe of SEQ ID NO:8 (white triangles).

FIG. 7 demonstrates that when each reaction is simultaneously treated with both probes, chemiluminescent data acquired from single tubes was separated into low and high wavelength emissions by filtered PMT1 and filtered PMT2. FIG. 7 clearly demonstrates that RLU from these two sets of emissions in single tubes allows linear quantitative detection of amplicons from about $10^6$ to $10^{10}$ copies per reaction of RNA transcript input.

Example 3

Quantitative Detection of Amplicons with AE-HICS Probes Over a Dynamic Range in the Same Reaction Chamber This example demonstrates an embodiment that provides quantitative detection of amplicons over a dynamic range from $10^4$ to $10^{10}$ copies of target input in the same reaction chamber.

At the completion of TMA reactions, 100 µL volumes of Hybridization Reagent were added and mixed. Separation Reagent (50 µL) was added, and the resulting mixtures were incubated at 60° C. for 10 minutes and at room temperature for 10 minutes. The tubes containing the above solutions were placed on a magnetic separation rack at room temperature for 5 minutes, the liquid phase was removed, 100 µL of probes in Hybridization Reagent were added, mixed and incubated at 60° C. for 15 minutes and at room temperature for 5 minutes. The same probes, combinations of probes, and concentrations were used as in Example 2.

At the completion of the hybridization reactions, the tubes containing the above solutions were placed on a magnetic separation rack at room temperature for 5 minutes and the liquid phase was removed. Next, 100 µL of Hybridization Reagent was added, mixed, placed on a magnetic separation rack at room temperature for 5 minutes and the liquid phase was removed. Finally, 100 µL volumes of Read Reagent were added and mixed.

Chemiluminescence from these reactions was acquired as in Example 2. The chemiluminescent output in RLUs from these intervals is reported in Tables 6 and 7. The last column in each table reflects the sum of the individual results.

TABLE 6

| PMT1 copies input | rep | 10 nM AE-labeled probe of SEQ ID NO: 7 RLU | RLU-bkgd | 100 nM AE-labeled probe of SEQ ID NO: 8 RLU | RLU-bkgd | 10 nM AE-labeled probe of SEQ ID NO: 7 100 nM AE-labeled probe of SEQ ID NO: 8 RLU | RLU-bkgd |
|---|---|---|---|---|---|---|---|
| 0 | 1 | 241 | | 2,186 | | 2,083 | |
| 0 | 2 | 274 | | 2,205 | | 2,044 | |
| $10^2$ | 1 | 265 | 8 | | | 2,005 | −59 |
| $10^2$ | 2 | 285 | 28 | | | 2,108 | 45 |
| $10^3$ | 1 | 282 | 25 | | | 2,091 | 28 |
| $10^3$ | 2 | 308 | 51 | | | 2,075 | 12 |
| $10^4$ | 1 | 345 | 88 | | | 2,289 | 226 |
| $10^4$ | 2 | 350 | 93 | | | 2,042 | −22 |
| $10^5$ | 1 | 949 | 692 | 2,103 | −93 | 2,600 | 537 |
| $10^5$ | 2 | 877 | 620 | 2,027 | −169 | 2,594 | 531 |
| $10^6$ | 1 | 2,481 | 2,224 | 2,138 | −58 | 4,386 | 2,323 |
| $10^6$ | 2 | 2,685 | 2,428 | 2,066 | −130 | 4,514 | 2,451 |
| $10^7$ | 1 | 6,093 | 5,836 | 2,458 | 263 | 8,162 | 6,099 |
| $10^7$ | 2 | 6,044 | 5,787 | 2,347 | 152 | 7,431 | 5,368 |
| $10^8$ | 1 | | | 3,570 | 1,375 | 12,833 | 10,770 |
| $10^8$ | 2 | | | 3,188 | 993 | 13,244 | 11,181 |
| $10^9$ | 1 | | | 7,238 | 5,043 | 22,468 | 20,405 |
| $10^9$ | 2 | | | 6,904 | 4,709 | 21,679 | 19,616 |
| $10^{10}$ | 1 | | | 18,439 | 16,244 | 35,697 | 33,634 |
| $10^{10}$ | 2 | | | 18,364 | 16,169 | 37,785 | 35,722 |

TABLE 7

| PMT2 copies input | rep | 10 nM AE-labeled probe of SEQ ID NO: 7 RLU | RLU-bkgd | 100 nM AE-labeled probe of SEQ ID NO: 8 RLU | RLU-bkgd | 10 nM AE-labeled probe of SEQ ID NO: 7 100 nM AE-labeled probe of SEQ ID NO: 8 RLU | RLU-bkgd |
|---|---|---|---|---|---|---|---|
| 0 | 1 | 408 | | 49,859 | | 47,502 | |
| 0 | 2 | 443 | | 49,554 | | 44,108 | |
| $10^2$ | 1 | 465 | 40 | | | 44,440 | −1365 |
| $10^2$ | 2 | 456 | 31 | | | 45,037 | −768 |
| $10^3$ | 1 | 471 | 46 | | | 44,644 | −1161 |
| $10^3$ | 2 | 458 | 33 | | | 45,240 | −565 |
| $10^4$ | 1 | 492 | 67 | | | 48,723 | 2,918 |
| $10^4$ | 2 | 509 | 84 | | | 41,912 | −3893 |
| $10^5$ | 1 | 479 | 54 | 50,653 | 947 | 49,501 | 3,696 |
| $10^5$ | 2 | 527 | 102 | 48,818 | −889 | 44,034 | −1771 |
| $10^6$ | 1 | 551 | 126 | 50,255 | 549 | 51,810 | 6,005 |
| $10^6$ | 2 | 566 | 141 | 48,679 | −1028 | 51,876 | 6,071 |
| $10^7$ | 1 | 645 | 220 | 64,907 | 15,201 | 67,800 | 21,995 |
| $10^7$ | 2 | 673 | 248 | 59,778 | 10,072 | 61,545 | 15,740 |
| $10^8$ | 1 | | | 143,945 | 94,239 | 114,205 | 68,400 |
| $10^8$ | 2 | | | 113,554 | 63,848 | 127,507 | 81,702 |
| $10^9$ | 1 | | | 393,948 | 344,242 | 383,192 | 337,387 |
| $10^9$ | 2 | | | 351,286 | 301,580 | 376,625 | 330,820 |
| $10^{10}$ | 1 | | | 1,029,786 | 980,080 | 997,605 | 951,800 |
| $10^{10}$ | 2 | | | 1,034,798 | 985,092 | 1,011,646 | 965,841 |

Figure 8:
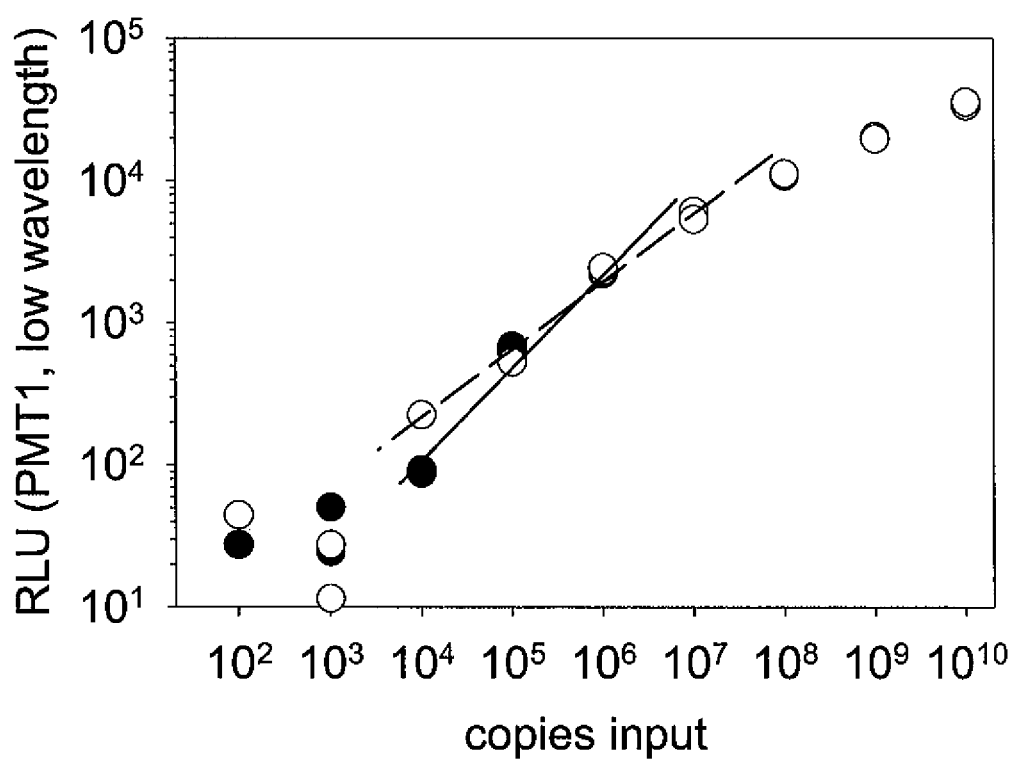
FIG. 8 is a graph showing the mean, background-subtracted PMT 1 RLU output from the reactions of self-quenching AE probes with amplicons of RNA transcripts at the indicated range of copy inputs as obtained in Example 3. Results shown are for (a) 10 nM labeled probe of SEQ ID NO:7 (black circles) and (b) 10 nM labeled probe of SEQ ID NO:7 plus 100 nM labeled probe of SEQ ID NO:8 (white circles).
Figure 9:
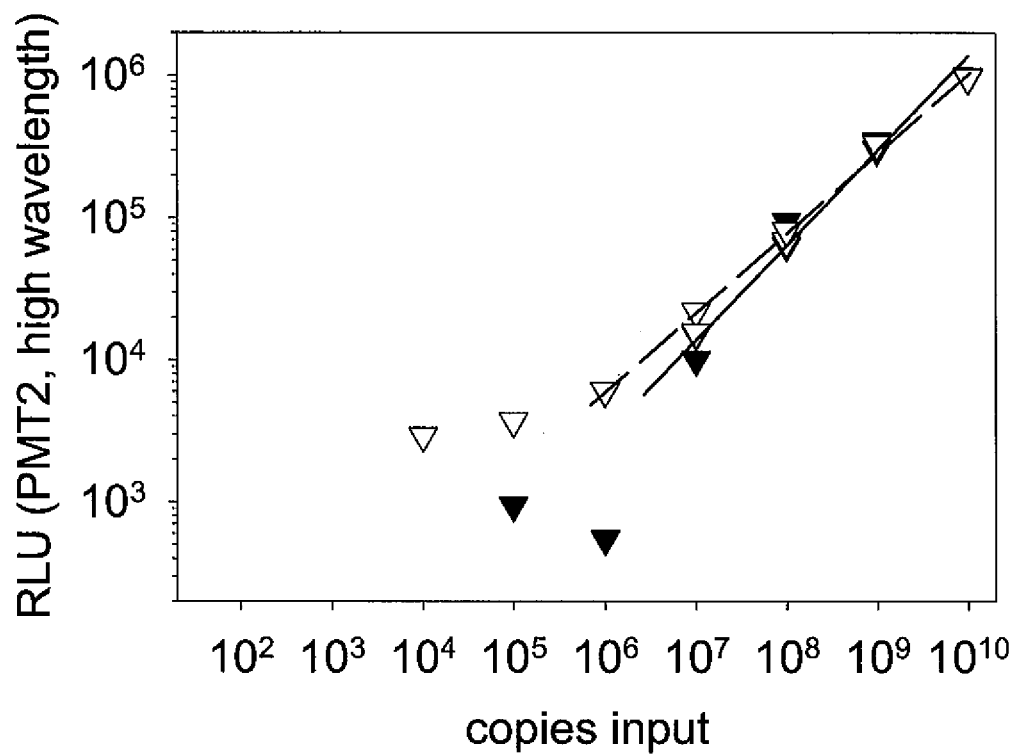
FIG. 9 is a graph showing the mean, background-subtracted PMT 2 RLU output from the reactions of self-quenching AE probes with amplicons of RNA transcripts at the indicated range of copy inputs as obtained in Example 3. Results shown are from (a) 100 nM labeled probe of SEQ ID NO:8 (black triangles) and (b) 100 nM labeled probe of SEQ ID NO:8 plus 10 nM labeled probe of SEQ ID NO:7 (white triangles).

The mean RLU from the zero RNA transcript input (first entry in each table) was used as the background ("bkgd") measurement and was subtracted from the results of experiments containing (a) $10^2$, $10^3$, $10^4$, $10^5$, $10^6$, and $10^7$ copies RNA transcripts input for AE-labeled probe of SEQ ID NO:7, (b) $10^5$, $10^6$, $10^7$, $10^8$, $10^9$ and $10^{10}$ copies RNA transcripts for AE-labeled probe of SEQ ID NO:8, or (c) $10^2$, $10^3$, $10^4$, $10^5$, $10^6$, $10^7$, $10^8$, $10^9$ and $10^{10}$ copies RNA transcripts for both probes (Tables 6 and 7, FIGS. 8 and 9).

FIG. 8 demonstrates that low wavelength RLU (captured by filtered PMT1) response from AE-labeled probe of SEQ ID NO:7 corresponds linearly from at least about $10^4$ to $10^6$ copies per reaction of RNA transcript input and that this response is similar whether the probe is used alone or in concert with AE-labeled probe of SEQ ID NO:8.

FIG. 9 demonstrates that high wavelength RLU (captured by filtered PMT2) response from AE-labeled probe of SEQ ID NO:8) corresponds linearly from at least about $10^7$ to $10^{10}$ copies per reaction of RNA transcript input and that this response is very similar whether the probe is used alone or in concert with AE-labeled probe of SEQ ID NO:7.

Figure 10:
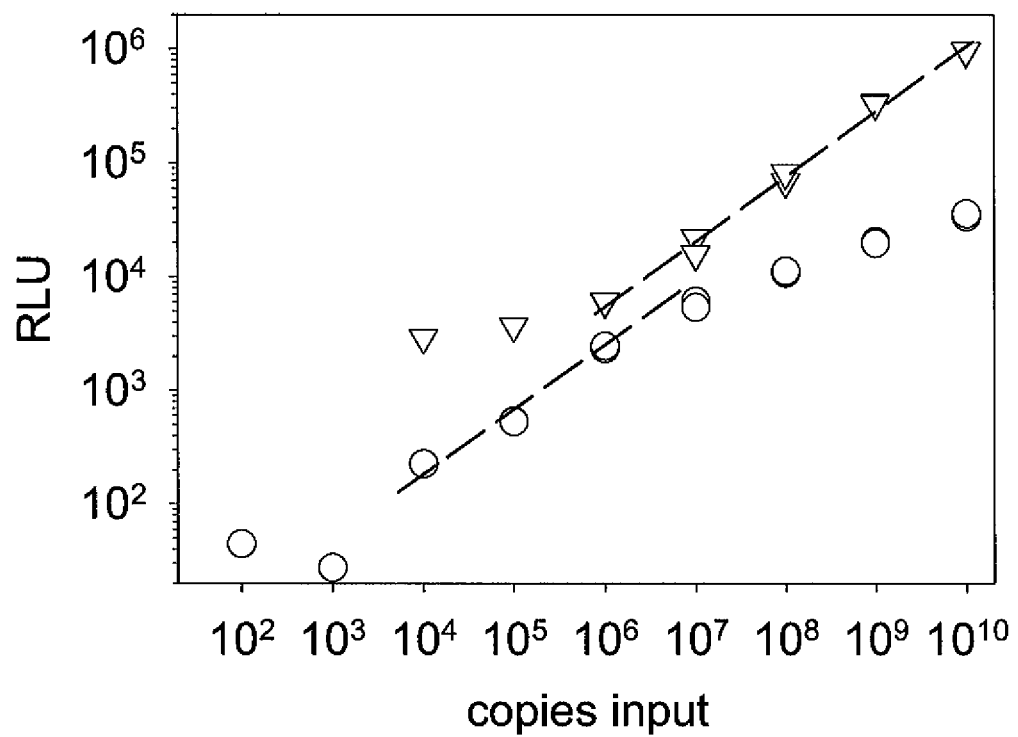
FIG. 10 is a graph showing the mean, background-subtracted RLU output from the reactions of self-quenching AE probes with amplicons of RNA transcripts at the indicated range of copy inputs as obtained in Example 3. Results shown are (a) PMT1 RLU for 10 nM labeled probe of SEQ ID NO:7 plus 100 nM labeled probe of SEQ ID NO:8 (white circles), and (b) PMT 2 RLU for 100 nM labeled probe of SEQ ID NO:8 plus 10 nM labeled probe of SEQ ID NO:7 (white triangles).

FIG. 10 demonstrates that when each reaction is simultaneously treated with both probes, chemiluminescent data acquired from single tubes was separated into low and high wavelength emissions by filtered PMT1 and filtered PMT2. FIG. 10 clearly demonstrates that RLU from these two sets of emissions in single tubes allows linear quantitative detection of amplicons from at least about $10^4$ to $10^{10}$ copies per reaction of RNA transcript input.

Example 4

Quantitative Detection of Amplicons with AE-Fluorophore Probes Over a Dynamic Range in the Same Reaction Chamber This example describes steps for detection of amplified products over a broad dynamic range of input target nucleic acids in the same reaction chamber.

TMA reactions are performed as described in the "Amplification Methods" section above. Hybridization workup and probe selection is performed as in Examples 2 or 3. The probes are present in total concentrations similar to those in the previous examples, i.e., sufficient to span the ranges of the amplicons synthesized and the detection apparatus. One of the probes has a standard type of AE attached to an oligonucleotide, as in Example 1. The other probe has a conjugate of an AE linked to a fluorophore, similar to AE conjugates with rhodamine and Texas Red described in U.S. Pat. No. 6,165,800 (emission spectra in FIGS. 1B and 1C), with the AE-fluorophore moiety attached to an oligonucleotide.

The luminescent probes are distinguishable from one another by different wavelength ranges of electromagnetic radiation emitted by each probe after initiation by addition and mixing of appropriate chemicals similar to those described in the previous examples, especially Example 1. Output emissions from a single detection vessel containing both the longer and shorter amplicons are simultaneously collected and separated into their respective wavelength ranges with, for example, a multiple wavelength luminometer like the one described in Example 2. The output from the first wavelength range corresponds to the first probe hybridized to both amplicons; the output from the second wavelength range corresponds to the second probe hybridized only to one of the amplicons. Alternately, the output from the second wavelength range corresponds to the first probe hybridized to both amplicons; the output from the first wavelength range corresponds to the second probe hybridized only to one of the amplicons. Unhybridized probes yield low emissions due to designs in the previous examples, especially due to treatment with Alkaline Reagent as in Example 1.

The mean RLU from the zero RNA transcript input (background or bkgd) is subtracted from the results of experiments containing $10^2$, $10^3$, $10^4$, $10^5$, $10^6$, $10^7$, $10^8$ and $10^9$ copies RNA transcripts input. Background-subtracted chemiluminescence from the first probe demonstrates a linear increase in RLU from about $10^2$ to about $10^6$ copies per reaction of RNA transcript input; background-subtracted chemiluminescence from the second probe demonstrates a linear increase in RLU from about $10^5$ to about $10^9$ copies per reaction of RNA transcript input. Alternately, background-subtracted chemiluminescence from the second probe demonstrates a linear increase in RLU from about $10^2$ to about $10^6$ copies per reaction of RNA transcript input; background-subtracted chemiluminescence from the first probe demonstrates a linear increase in RLU from about $10^5$ to about $10^9$ copies per reaction of RNA transcript input. The slopes of responses from the two sets of probes are co-linear. Linear output responses from these two probes overlap. However, taken together, the output from these two probes demonstrates quantitative detection of amplicons from about $10^2$ to about $10^9$ copies per reaction of RNA transcript input.

Example 5

Quantitative Detection of Amplicons with AE-HICS Probes Over a Dynamic Range in the Same Reaction Chamber This example demonstrates methods that show quantitative detection of amplified nucleic acid sequences resulting from target nucleic acids over a dynamic range from about $10^2$ to $10^9$ copies of input target nucleic acid in the same reaction chamber.

At the completion of TMA reactions, samples were processed using methods substantially similar to those described in Examples 2 and 3. The probes used were (a) 10 nM self-quenching AE-labeled probe of SEQ ID NO:7, (b) 100 nM self-quenching, wavelength-shifted AE-labeled probe of SEQ ID NO:8, or (c) both probes at the concentrations indicated for individual probes in (a) and (b). The relative placement of the probes on the distinguishable amplicons is shown diagrammatically in FIG. 4. The AE-labeled probe of SEQ ID NO:7 is able to detect both amplicons, whereas the AE-labeled probe of SEQ ID NO:8 is only able to detect one of the amplicons.

Chemiluminescence from these reactions was acquired as in Examples 2 and 3 except the probes were pretreated and then the detection reactions were initiated by addition of 200 µL of Detection Reagent 5 instead of Detection Reagent 3 followed by addition of 200 µL Detection Reagent 4. The chemiluminescent output in RLUs from these intervals is reported in Tables 8 and 9. The last column in each table reflects the sum of the individual probe outputs.

TABLE 8

| PMT1 copies input | rep | 10 nM AE-labeled probe of SEQ ID NO: 7 | | 100 nM AE-labeled probe of SEQ ID NO: 8 | | 10 nM AE-labeled probe of SEQ ID NO: 7 100 nM AE-labeled probe of SEQ ID NO: 8 | |
|---|---|---|---|---|---|---|---|
| | | RLU | RLU-bkgd | RLU | RLU-bkgd | RLU | RLU-bkgd |
| 0 | 1 | 14,562 | | 26,106 | | 36,423 | |
| 0 | 2 | 14,438 | | 24,472 | | 36,827 | |
| 0 | 3 | 14,082 | | 26,331 | | 36,803 | |
| $10^2$ | 1 | 14,794 | 433 | 25,179 | −457 | 35,358 | −1326 |
| $10^2$ | 2 | 14,929 | 568 | 27,807 | 2,171 | 37,238 | 554 |
| $10^2$ | 3 | 14,862 | 501 | 27,130 | 1,494 | 37,488 | 804 |
| $10^3$ | 1 | 15,678 | 1,317 | 25,340 | −296 | 39,793 | 3,109 |
| $10^3$ | 2 | 21,002 | 6,641 | 27,005 | 1,369 | 38,311 | 1,627 |
| $10^3$ | 3 | 16,434 | 2,073 | 26,027 | 391 | 38,101 | 1,417 |
| $10^4$ | 1 | 24,766 | 10,405 | 25,362 | −274 | 51,125 | 14,441 |
| $10^4$ | 2 | 23,483 | 9,122 | 25,919 | 283 | 47,760 | 11,076 |
| $10^4$ | 3 | 26,572 | 12,211 | 25,078 | −558 | 54,378 | 17,694 |
| $10^5$ | 1 | 72,559 | 58,198 | 26,854 | 1,218 | 121,786 | 85,102 |
| $10^5$ | 2 | 78,041 | 63,680 | 25,406 | −230 | 106,645 | 69,961 |
| $10^5$ | 3 | 95,444 | 81,083 | 23,635 | −2001 | 115,123 | 78,439 |
| $10^6$ | 1 | 186,102 | 171,741 | 25,108 | −528 | 203,978 | 167,294 |
| $10^6$ | 2 | 191,297 | 176,936 | 26,075 | 439 | 271,260 | 234,576 |
| $10^6$ | 3 | 199,336 | 184,975 | 24,664 | −972 | 255,668 | 218,984 |
| $10^7$ | 1 | 588,202 | 573,841 | 27,084 | 1,448 | 586,704 | 550,020 |
| $10^7$ | 2 | 413,767 | 399,406 | 26,679 | 1,043 | 602,568 | 565,884 |
| $10^7$ | 3 | 450,198 | 435,837 | 28,763 | 3,127 | 526,836 | 490,152 |
| $10^8$ | 1 | 723,259 | 708,898 | 37,317 | 11,681 | 961,790 | 925,106 |
| $10^8$ | 2 | 723,269 | 708,908 | 39,453 | 13,817 | 944,710 | 908,026 |
| $10^8$ | 3 | 763,899 | 749,538 | 37,161 | 11,525 | 984,831 | 948,147 |
| $10^9$ | 1 | 1,034,534 | 1,020,173 | 55,336 | 29,700 | 1,100,567 | 1,063,883 |
| $10^9$ | 2 | 994,327 | 979,966 | 54,090 | 28,454 | 1,136,950 | 1,100,266 |
| $10^9$ | 3 | 1,076,328 | 1,061,967 | 52,833 | 27,197 | 1,130,972 | 1,094,288 |
| $10^{10}$ | 1 | 1,110,316 | 1,095,955 | 60,085 | 34,449 | 1,106,720 | 1,070,036 |
| $10^{10}$ | 2 | 1,080,085 | 1,065,724 | 59,140 | 33,504 | 1,149,267 | 1,112,583 |
| $10^{10}$ | 3 | 1,136,136 | 1,121,775 | 56,674 | 31,038 | 1,112,549 | 1,075,865 |

TABLE 9

| PMT2 copies input | rep | 10 nM AE-labeled probe of SEQ ID NO: 7 | | 100 nM AE-labeled probe of SEQ ID NO: 8 | | 10 nM AE-labeled probe of SEQ ID NO: 7 100 nM AE-labeled probe of SEQ ID NO: 8 | |
|---|---|---|---|---|---|---|---|
| | | RLU | RLU-bkgd | RLU | RLU-bkgd | RLU | RLU-bkgd |
| 0 | 1 | 2,952 | | 236,010 | | 208,897 | |
| 0 | 2 | 2,913 | | 232,904 | | 221,790 | |
| 0 | 3 | 3,112 | | 227,080 | | 233,341 | |
| $10^2$ | 1 | 3,013 | 21 | 196,451 | −35547 | 206,041 | −15302 |
| $10^2$ | 2 | 3,063 | 71 | 315,433 | 83,435 | 203,440 | −17903 |
| $10^2$ | 3 | 3,159 | 167 | 223,865 | −8133 | 194,955 | −26388 |
| $10^3$ | 1 | 3,126 | 134 | 200,219 | −31779 | 238,950 | 17,607 |
| $10^3$ | 2 | 3,231 | 239 | 218,126 | −13872 | 201,506 | −19837 |
| $10^3$ | 3 | 3,165 | 173 | 216,653 | −15345 | 210,847 | −10496 |
| $10^4$ | 1 | 3,335 | 343 | 242,834 | 10,836 | 254,037 | 32,694 |
| $10^4$ | 2 | 3,388 | 396 | 230,274 | −1724 | 189,268 | −32075 |
| $10^4$ | 3 | 3,507 | 515 | 231,765 | −233 | 299,412 | 78,069 |
| $10^5$ | 1 | 4,250 | 1,258 | 262,302 | 30,304 | 199,632 | −21711 |
| $10^5$ | 2 | 4,139 | 1,147 | 262,013 | 30,015 | 211,301 | −10042 |
| $10^5$ | 3 | 4,527 | 1,535 | 203,150 | −28848 | 220,057 | −1286 |
| $10^6$ | 1 | 5,777 | 2,785 | 250,081 | 18,083 | 224,196 | 2,853 |
| $10^6$ | 2 | 5,973 | 2,981 | 257,312 | 25,314 | 229,233 | 7,890 |
| $10^6$ | 3 | 6,076 | 3,084 | 246,642 | 14,644 | 227,106 | 5,763 |
| $10^7$ | 1 | 12,273 | 9,281 | 453,599 | 221,601 | 461,451 | 240,108 |
| $10^7$ | 2 | 9,704 | 6,712 | 373,223 | 141,225 | 646,791 | 425,448 |
| $10^7$ | 3 | 10,029 | 7,037 | 521,274 | 289,276 | 332,741 | 111,398 |
| $10^8$ | 1 | 14,422 | 11,430 | 1,326,590 | 1,094,592 | 1,280,870 | 1,059,527 |
| $10^8$ | 2 | 14,559 | 11,567 | 1,466,518 | 1,234,520 | 1,238,109 | 1,016,766 |
| $10^8$ | 3 | 15,583 | 12,591 | 1,368,674 | 1,136,676 | 1,283,745 | 1,062,402 |
| $10^9$ | 1 | 19,047 | 16,055 | 4,248,797 | 4,016,799 | 4,424,877 | 4,203,534 |
| $10^9$ | 2 | 19,191 | 16,199 | 4,357,020 | 4,125,022 | 4,280,862 | 4,059,519 |

TABLE 9-continued

| PMT2 | | 10 nM AE-labeled probe of SEQ ID NO: 7 | | 100 nM AE-labeled probe of SEQ ID NO: 8 | | 10 nM AE-labeled probe of SEQ ID NO: 7 100 nM AE-labeled probe of SEQ ID NO: 8 | |
|---|---|---|---|---|---|---|---|
| copies input | rep | RLU | RLU-bkgd | RLU | RLU-bkgd | RLU | RLU-bkgd |
| $10^9$ | 3 | 20,178 | 17,186 | 4,228,440 | 3,996,442 | 3,605,149 | 3,383,806 |
| $10^{10}$ | 1 | 20,793 | 17,801 | 6,357,492 | 6,125,494 | 6,096,242 | 5,874,899 |
| $10^{10}$ | 2 | 21,125 | 18,133 | 6,265,950 | 6,033,952 | 6,208,776 | 5,987,433 |
| $10^{10}$ | 3 | 20,856 | 17,864 | 6,316,084 | 6,084,086 | 5,881,110 | 5,659,767 |

Figure 11:
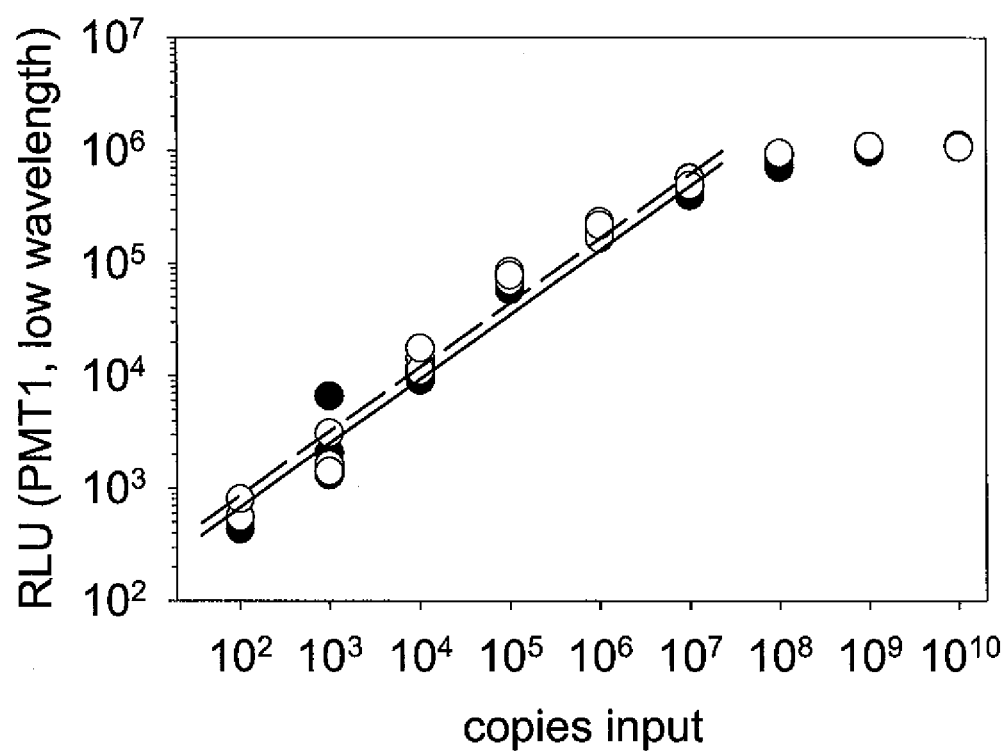
FIG. 11 is a graph showing the mean, background-subtracted PMT 1 RLU output from the reactions of self-quenching AE probes with amplicons of RNA transcripts at the indicated range of copy inputs as obtained in Example 5. Results shown are (a) 10 nM labeled probe of SEQ ID NO:7 (black circles) and (b) 10 nM labeled probe of SEQ ID NO:7 plus 100 nM labeled probe of SEQ ID NO:8 (white circles).
Figure 12:
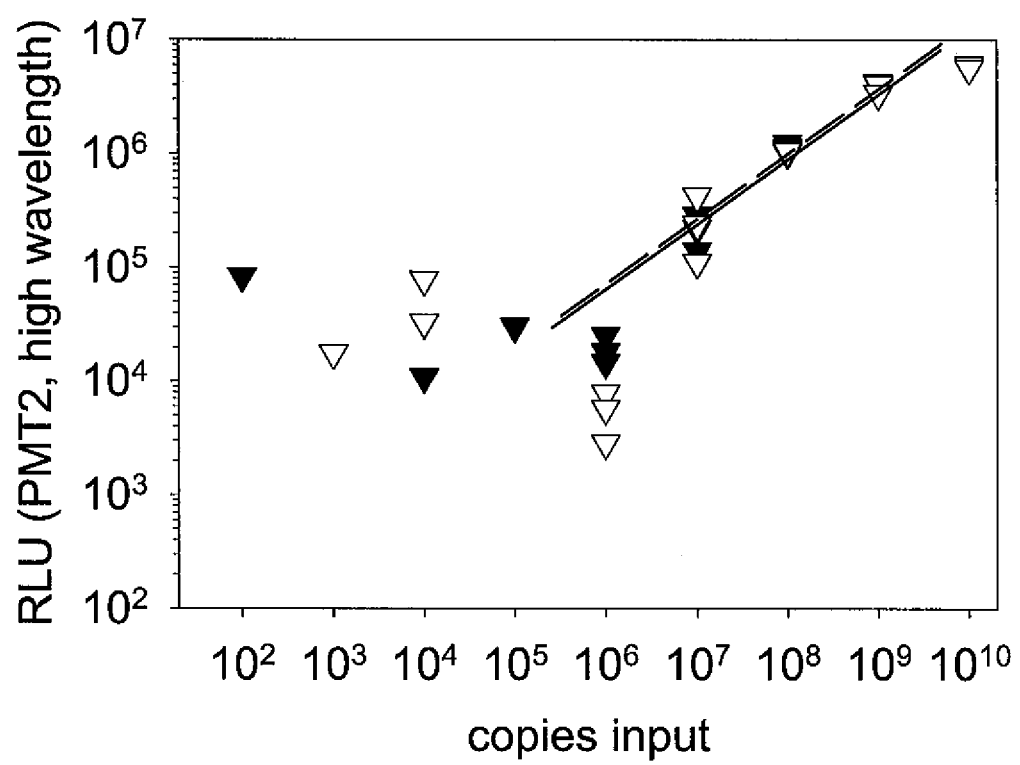
FIG. 12 is a graph showing the mean, background-subtracted PMT 2 RLU output from the reactions of self-quenching AE probes with amplicons of RNA transcripts at the indicated range of copy inputs as obtained in Example 5. Results shown are (a) 100 nM labeled probe of SEQ ID NO:8 (black triangles) and (b) 100 nM labeled probe of SEQ ID NO:8 plus 10 nM labeled probe of SEQ ID NO:7 (white triangles).

The mean RLU from the zero RNA transcript input (first entry in each table) was used as the background ("bkgd") measurement and was subtracted from the results of experiments containing $10^2$, $10^3$, $10^4$, $10^5$, $10^6$, $10^7$, $10^8$, $10^9$ and $10^{10}$ copies RNA transcripts input for AE-labeled probes of SEQ ID NO:7, SEQ ID NO:8, or both probes (Tables 8 and 9, FIGS. 11 and 12).

FIG. 11 demonstrates that low wavelength RLU (captured by filtered PMT1) response from AE-labeled probe of SEQ ID NO:7 corresponds linearly from at least about $10^2$ to $10^7$ copies per reaction of RNA transcript input and that this response is similar whether the probe is used alone or in concert with AE-labeled probe of SEQ ID NO:8.

FIG. 12 demonstrates that high wavelength RLU (captured by filtered PMT2) response from AE-labeled probe of SEQ ID NO:8 corresponds linearly from at least about $10^7$ to $10^9$ copies per reaction of RNA transcript input and that this response is very similar whether the probe is used alone or in concert with AE-labeled probe of SEQ ID NO:7.

Figure 13:
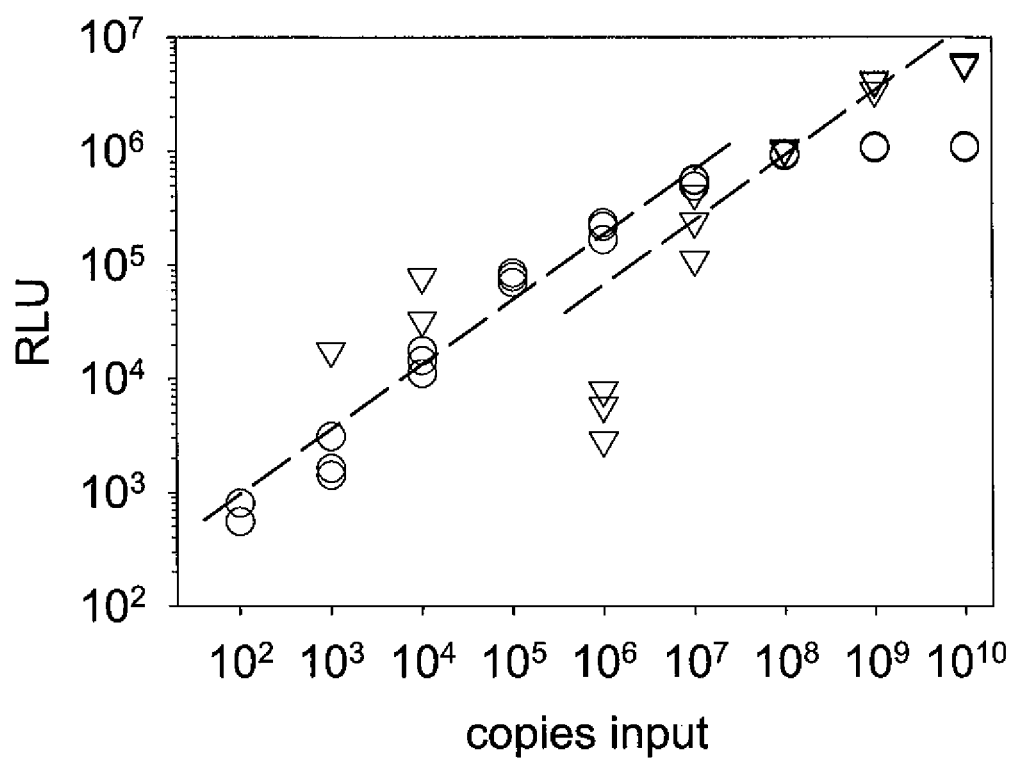
FIG. 13 is a graph depicting the mean, background-subtracted RLU output from the reactions of self-quenching AE probes with amplicons of RNA transcripts at the indicated range of copy inputs as obtained in Example 5. Results shown are (a) PMT1 RLU for 10 nM labeled probe of SEQ ID NO:7 plus 100 nM labeled probe of SEQ ID NO:8 (white circles), and (b) PMT 2 RLU for 100 nM labeled probe of SEQ ID NO:8 plus 10 nM labeled probe of SEQ ID NO:7 (white triangles).

FIG. 13 demonstrates that when each reaction is simultaneously treated with both probes, chemiluminescent data acquired from single tubes was separated into low and high wavelength emissions by filtered PMT1 and filtered PMT2. FIG. 13 clearly demonstrates that RLU from these two sets of emissions in single tubes allows linear quantitative detection of amplicons from about $10^2$ to $10^9$ copies per reaction of RNA transcript input.

Example 6

Detection of Distinguishable Amplicons Made Using Modified and Unmodified Primers This example demonstrates quantitative detection of amplicons from over a range of $10^3$ to $10^9$ copies of target nucleic acid in the same reaction tubes. The amplification oligonucleotides are a first promoter provider and a second promoter provider wherein the two promoter providers comprise substantially identical nucleotide sequences except that at least one of the two promoter providers is modified so to produce a distinguishable amplicon relative to that produced by the other promoter provider. The first and the second promoter providers are also present in the TMA reaction in different concentrations so as to generate a differentiable ratio of their respective amplicons.

Using the illustrative amplification system described above, the first promoter provider is SEQ ID NO:1 and the second promoter provider is substantially identical to SEQ ID NO:1 except that the target hybridizing sequence contains a modified nucleobase. The first promoter provider is present in the amplification reaction at a concentration that is 1000 times in excess as the concentration for the second promoter provider. In addition, SEQ ID NO:2 is used as the amplification oligonucleotide member in conjunction with both the first and the second promoter providers. Isothermal amplification is performed.

At the completion of the TMA amplification reactions, 100 µL volumes of probes in Hybridization Reagent is added to the amplification reaction mixtures, which are mixed and incubated at 60° C. for 15 minutes, which will allow hybridization of probes specific for complementary sequences in the synthesized amplicons. The probes are: (a) an AE-labeled probe that hybridizes to the amplicon produced using the first promoter provider but not the amplicon produced using the second promoter provider; and (b) AE-labeled probe that hybridizes to the amplicon produced using the second promoter provider but not the amplicon produced using the first promoter provider. These AE-labeled probes hybridize their respective amplicons at a position that includes the distinguishable position represented by the modification present in the second promoter provider but not the first promoter provider.

Chemiluminescence from these reactions is acquired essentially as in Example 5. Reactions can be initiated by addition of 200 µL Detection Reagent 5 instead of Detection Reagent 3.

Example 7

Detection of Distinguishable Products Made Using Promoter-Based Amplification Oligomers with 5' Unpaired Base(s) Provided Between the 3' End of their Promoter Sequences and the 5' End of their Target Hybridizing Sequences This example demonstrates quantitative detection of amplicons over a range of $10^3$ to $10^9$ copies of target nucleic acid in the same reaction tubes. The amplification oligonucleotides are a first promoter amplification oligonucleotide and a second promoter oligonucleotide, wherein the two promoter amplification oligonucleotides comprise substantially identical nucleotide sequences except that each of the two promoter amplification oligonucleotides comprise between the 5' end of their target hybridizing sequences and the 3' end of their promoter sequences, at least one separately unique unpaired base so to produce a distinguishable amplicon relative to that produced by the other promoter amplification oligonucleotide. The first and the second promoter oligonucleotides are also present in the TMA reaction in different concentrations so as to generate a differentiable ratio of their respective amplicons.

Using the illustrative amplification system described above, the first promoter oligonucleotide is SEQ ID NO:1 further comprising a 5' unpaired base (5'-AATTAATAC- GACTCACTATAGGGAGA(X)GTTTGTATGTCTGTTGC-TATTAT-3' (5' unpaired base X version of SEQ ID NO:1, wherein X represents one or more unpaired bases)) and the second promoter oligonucleotide is also SEQ ID NO:1 further comprising a 5' unpaired base that is distinguishable from that present on the first promoter oligonucleotide (5'-AATT-TAATACGACTCACTATAGGGAGA(Y)GTTTGTAT-GTCTGTTGCTATTAT-3' (5' unpaired base Y version of SEQ ID NO:1, wherein Y represents one or more unpaired bases and wherein the contiguous nucleotide sequence Y is not the same as the contiguous nucleotide sequence X)). The first promoter oligonucleotide is present in the amplification reaction at a concentration that is 1000 times in excess as the concentration for the second promoter oligonucleotide. In addition, SEQ ID NO:2 is used as the amplification oligonucleotide member in conjunction with both the first and the second promoter oligonucleotides. Isothermal amplification is performed.

At the completion of the TMA amplification reactions, 100 μL volumes of probes in Hybridization Reagent are added to the amplification reaction mixtures, which are mixed and incubated at 60° C. for 15 minutes to allow hybridization of probes specific for complementary sequences in the synthesized amplicons. The probes are: (a) an AE-labeled probe that hybridizes to the amplicon produced using the first promoter oligonucleotide but not the amplicon produced using the second promoter oligonucleotide; and (b) AE-labeled probe that hybridizes to the amplicon produced using the second promoter oligonucleotide but not the amplicon produced using the first promoter oligonucleotide. These AE-labeled probes hybridize their respective amplicons at a position that includes the distinguishable position represented by the modification present in the second promoter oligonucleotide but not the first promoter oligonucleotide.

Chemiluminescence from these reactions is acquired essentially as in Example 5.

Example 8

Detection of Distinguishable Products Made Using Amplification Oligonucleotides with 5' Unpaired Bases This example demonstrates quantitative detection of amplicons over a range of $10^3$ to $10^9$ copies of target nucleic acid in the same reaction tubes. The amplification oligonucleotides are a first amplification oligonucleotide and a second oligonucleotide wherein the two amplification oligonucleotides comprise substantially identical nucleotide sequences except that each of the two amplification oligonucleotides comprise a separately unique 5' unpaired base so to produce a distinguishable amplicon relative to that produced by the other amplification oligonucleotide. The first and the second amplification oligonucleotides are also present in the TMA reaction in different concentrations so as to generate a differentiable ratio of their respective amplicons.

Using the illustrative amplification system described above, the first amplification oligonucleotide is SEQ ID NO:2 further comprising a 5' unpaired base (5'-(X)ACAGCAGTA-CAAATGGCAG-3' (5' unpaired base X version of SEQ ID NO:2, wherein X represents one or more unpaired bases)) and the second amplification oligonucleotide is also SEQ ID NO:2 further comprising a 5' unpaired base that is distinguishable from that present on the first promoter oligonucleotide (5'-(Y)ACAGCAGTACAAATGGCAG-3' (5' unpaired base Y version of SEQ ID NO:2, wherein Y represents one or more unpaired bases and wherein the contiguous nucleotide sequence Y is not the same as the contiguous nucleotide sequence X)). In this example, X is a contiguous nucleic acid sequence that is 5 nucleobases in length and Y is a contiguous nucleic acid sequence that is 5 nucleobases in length, wherein the contiguous nucleic acid sequences of X and Y are dissimilar thus allowing for separately detecting and distinguishing each subsequent amplicon species. The first amplification oligonucleotide is present in the amplification reaction at a concentration that is 1000 times in excess as the concentration for the second amplification oligonucleotide. In addition, SEQ ID NO:1 is used as the promoter amplification oligonucleotide member in conjunction with both the first and the second amplification oligonucleotides. Isothermal amplification is performed.

At the completion of the TMA amplification reactions, 100 μL volumes of probes in Hybridization Reagent are added to the amplification reaction mixtures, which are mixed and incubated at 60° C. for 15 minutes, which allows hybridization of probes specific for complementary sequences in the synthesized amplicons. The probes are: (a) an AE-labeled probe that hybridizes to the amplicon produced using the first amplification oligonucleotide but not the amplicon produced using the second amplification oligonucleotide; and (b) AE-labeled probe that hybridizes to the amplicon produced using the second amplification oligonucleotide but not the amplicon produced using the first amplification oligonucleotide. These AE-labeled probes hybridize their respective amplicons at a position that includes the distinguishable position represented by the modification present in the second promoter amplification oligonucleotide but not the first promoter amplification oligonucleotide.

Chemiluminescence from these reactions is acquired essentially as in Example 5.

Example 9

Detection of Distinguishable Products Made Using Promoter Amplification Oligonucleotides with Different Promoter Sequences This example demonstrates quantitative detection of amplicons over a range of $10^3$ to $10^9$ copies of target nucleic acid in the same reaction tubes. The amplification oligonucleotides are a first promoter-based amplification oligonucleotide and a second promoter-based amplification oligonucleotide wherein the two promoter-based amplification oligonucleotides comprise substantially identical nucleotide sequences except that at least one of the two promoter-based amplification oligonucleotides is modified so to produce a distinguishable amplicon relative to that produced by the other promoter-based amplification oligonucleotide (for example, as in Example 6). The first and the second promoter-based amplification oligonucleotides are present in the TMA reaction in similar concentrations. The promoter sequence of the second promoter-based amplification oligonucleotide is modified relative to the promoter sequence of the first promoter-based amplification oligonucleotide so as to generate a differentiable ratio of their respective amplicons.

Using the illustrative amplification system described above, the first promoter-based amplification oligonucleotide is SEQ ID NO:1 and the second promoter-based amplification oligonucleotide is substantially identical to SEQ ID NO:1 except that the target hybridizing sequence contains a modified nucleobase. In addition, the second promoter-based amplification oligonucleotide contains a change to its promoter sequence (e.g., a modified nucleobase, missing nucleobase, extra nucleobase or non-deoxyribonucleotide nucleobase, e.g., a ribonucleotide nucleobase). The promoter sequence of the second promoter-based amplification oligonucleotide is about 1000 times less efficient in synthesizing RNA transcripts than the unmodified promoter sequence of the first promoter-based amplification oligonucleotide. In addition, SEQ ID NO:2 is used as the amplification oligonucleotide member in conjunction with both the first and the second promoter-based amplification oligonucleotides. Isothermal amplification is performed.

At the completion of the TMA amplification reactions, 100 μL volumes of probes in Hybridization Reagent are added to the amplification reaction mixtures, which are mixed and incubated at 60° C. for 15 minutes, which allows hybridization of probes specific for complementary sequences in the synthesized amplicons. The probes are: (a) an AE-labeled probe that hybridizes to the amplicon produced using the first promoter-based amplification oligonucleotide but not the amplicon produced using the second promoter-based amplification oligonucleotide; and (b) AE-labeled probe that hybridizes to the amplicon produced using the second promoter-based amplification oligonucleotide but not the amplicon produced using the first promoter-based amplification oligonucleotide. These AE-labeled probes hybridize their respective amplicons at a position that includes the distinguishable position represented by the modification present in the second promoter-based amplification oligonucleotide but not the first promoter-based amplification oligonucleotide.

Chemiluminescence from these reactions is acquired essentially as in Example 5.

Example 10

Distinguishable DNA and RNA Products

This example demonstrates quantitative detection of amplicons over a range of $10^3$ to $10^9$ copies of target nucleic acid in the same reaction tubes. The amplification oligonucleotides used herein are a single primer and a single promoter provider. The distinguishable amplification products are (i) the DNA amplicons made during some of the steps of the TMA reaction, and (ii) the RNA transcripts made during some of the steps of the TMA reaction. DNA and RNA are generated in TMA such that the RNA amplification products are in excess compared to the DNA amplification products so as to generate a differentiable ratio of these respective amplicons.

Using the illustrative amplification system described above, the amplification oligonucleotide is SEQ ID NO:2, and SEQ ID NO:1 is used as the promoter amplification oligonucleotide member. Isothermal amplification is performed.

At the completion of the TMA amplification reactions, 100 μL volumes of probes in Hybridization Reagent are added to the amplification reaction mixtures, which are mixed and incubated at 60° C. for 15 minutes, which allows hybridization of probes specific for complementary sequences in the synthesized amplicons. The probes are: (a) an AE-labeled probe that hybridizes to the DNA amplicon; and (b) an AE-labeled probe that hybridizes to the RNA amplicon. The probe hybridizing to the DNA amplicon preferably hybridizes to the strand that is antisense to the RNA amplicon. These AE-labeled probes hybridize their respective amplicons at positions that are distinguishable.

Chemiluminescence from these reactions is acquired essentially as in Example 5.

Example 11

Detection of Distinguishable Products Made Using Distinguishable Nucleotide Triphosphates (NTPs)

This example demonstrates quantitative detection of amplicons over a range of $10^3$ to $10^9$ copies of target nucleic acid in the same reaction tubes. The amplification oligonucleotides used herein are a single amplification oligonucleotide and a single promoter amplification oligonucleotide. A fifth NTP is included in the amplification composition. The NTP mix, then, is A, T, G and a ratio of C and IsoC, wherein the amount of C is greater than the amount of IsoC. Amplicons species incorporate the C of the IsoC at an unequal ratio that approximately equals the unequal ratio of C:IsoC provided into the amplification reaction. Therefore, the probe binding site on each amplicon species has either a C or an IsoC, which provides differentiable amplicons species at unequal amounts (e.g., (i) the RNA amplicon species having A, C, T and G incorporated into the probe binding site, and (ii) the RNA amplicon species having A, IsoC, T and G incorporated into the probe binding site).

Using the illustrative amplification system described above, the amplification oligonucleotide is SEQ ID NO:2, and SEQ ID NO:1 is used as the promoter amplification oligonucleotide member. The NTP mix is A, T, G, and C:IsoC in an 1000:1 ratio. Isothermal amplification is performed.

At the completion of the TMA amplification reactions, 100 μL volumes of probes in Hybridization Reagent are added to the amplification reaction mixtures, which are mixed and incubated at 60° C. for 15 minutes, which allows hybridization of probes specific for complementary sequences in the synthesized amplicons. The probes are: (a) an AE-labeled probe that is 12-nt in length and comprises a contiguous nucleotide sequence that is made of the natural NTPs so that the probe hybridizes and detects the more abundant amplicon species that incorporate the native C residue into their primer binding site; and (b) an AE-labeled probe that is 12-nt in length and comprises a contiguous nucleotide sequence that is made of the natural A, T and C residues and IsoG residues so that the probe hybridizes and detects the less abundant amplicon species that incorporate the IsoC residue into their primer binding site. These AE-labeled probes hybridize their respective amplicons at positions that are distinguishable.

Chemiluminescence from these reactions is acquired essentially as in Example 5.

Example 12

Detection of Distinguishable Products Made Using Two Pairs of Amplification Oligonucleotides that Synthesize Amplicons that do not Overlap This example demonstrates quantitative detection of amplicons over a range of $10^3$ to $10^9$ copies of target nucleic acid in the same reaction tubes. The amplification oligonucleotides are a first set comprising a first amplification oligonucleotide and a first promoter amplification oligonucleotide, and a second set comprising a second amplification oligonucleotide and a second promoter amplification oligonucleotide, wherein the two sets of amplification oligonucleotides comprise substantially non-overlapping target binding sites such that each of the two sets of amplification oligonucleotides produce a distinguishable amplicon relative to that produced by the other amplification oligonucleotide. The first and the second sets of amplification oligonucleotides are also present in the TMA reaction in different concentrations so as to generate a differentiable ratio of their respective amplicons.

Using the illustrative amplification system described above, the first amplification oligonucleotide is SEQ ID NO:2 and the first promoter amplification oligonucleotide is SEQ ID NO:1, and the second amplification oligonucleotide is SEQ ID NO:3 and the second promoter amplification oligomer has a target binding sequence that is complementary to the target sequence between SEQ ID NO:2 and SEQ ID NO:3 and that is near the target sequence complementary to SEQ ID NO:2. The first amplification oligonucleotide is present in the amplification reaction at a concentration that is 1000 times in excess as the concentration for the second amplification oligonucleotide. Isothermal amplification is performed.

At the completion of the TMA amplification reactions, 100 µL volumes of probes in Hybridization Reagent are added to the amplification reaction mixtures, which are mixed and incubated at 60° C. for 15 minutes, which allows hybridization of probes specific for complementary sequences in the synthesized amplicons. The probes are: (a) an AE-labeled probe that hybridizes to the amplicon produced using the first set of amplification oligonucleotides but not the amplicon produced using the second set of amplification oligonucleotides; and (b) AE-labeled probe that hybridizes to the amplicon produced using the second set of amplification oligonucleotides but not the amplicon produced using the first set of amplification oligonucleotides. These AE-labeled probes hybridize to their respective amplicons at a position that includes the distinguishable position represented by the unique sequences synthesized between the first set of amplification oligonucleotides or between the second set of amplification oligonucleotides.

Chemiluminescence from these reactions is acquired essentially as in Example 5.

TABLE 10

| SEQ ID NO: | Sequence (5' to 3') | Comment |
|---|---|---|
| 1 | AATTTAATACGACTCACTATAGGGAGAGTTTGT ATGTCTGTTGCTATTAT | Promoter-primer |
| 2 | ACAGCAGTACAAATGGCAG | Primer |
| 3 | ATTCCCTACAATCCCCAAAGTCAA | Primer |
| 4 | GGGAGACAAGCUUGCAUGCCUGCAGGUCGACUC UAGAGGAUCCCCGGGUACCAGCACACAAAGGAA UUGGAGGAAAUGAACAAGUAGAUAAAUUAGUCA GUGCUGGAAUCAGGAAAAUACUAUUUUUAGAUG GAAUAGAUAAGGCCCAAGAUGAACAUGAGAAAU AUCACAGUAAUUGGAGAGCAAUGGCUAGUGAUU UUAACCUGCCACCUGUAGGUAGCAAAAGAAAUA GUAGCCAGCUGUGAUAAAUUCAGCUAAAAGGAG AAGCCAUGCAUGGACAAGUAGACUGUAGUCCAG GAAUAUGGCAACUAGAUUGUACACAUUUAGAAG GAAAAGUUAUCCUGGUAGCAGUUCAUGUAGCCA GUGGAUAUAUAGAAGCAGAAGUUAUUCCAGCAG AAACAGGGCAGGAAACAGCAUAUUUUCUUUUAA AAUUAGCAGGAAGAUGGCCAGUAAAACAAUAC AUACAGACAAUGGCAGCAAUUUCACCAGUGCUA CGGUUAAGGCCGCCUGUUGGUGGGCGGGAAUCA AGCAGGAAUUUGGAAUUCCCUACAAUCCCCAAA GUCAAGGAGUAGUAGAAUCUAUGAAUAAAGAAU UAAAGAAAAUUAAGGACAGGUAAGAGAUCAGG CUGAACAUCUUAAGACAGCAGUACAAAUGGCAG UAUUCAUCCACAAUUUUAAAAGAAAAGGGGGGA UUGGGGGGUACAGUGCAGGGGAAAGAAUAGUAG ACAUAAUAGCAACAGACAUACAAACUAAAGAAU UACAAAAACAAAUUACAAAAAUUCAAAAUUUUC | in vitro transcript |

TABLE 10-continued

| SEQ ID NO: | Sequence (5' to 3') | Comment |
|---|---|---|
| | GGGUUUAUUACAGGGACAGCAGAAAUCCACUUU GGAAAGGACCAGCAAAGCUCCUCUGGAAAGGUG AAGGGGCAGUAGUAAUACAAGAUAAUAGUGACA UAAAAGUAGUGCCAAGAAGAAAAGCAAAGAUCA UUAGGGAUUAUGGAAAACAGAUGGCAGGUGAUG AUUGUGUGGCAAGUAGACAGGAUGAGGAUUAGA ACAUGGAAAAGUUUAGUAAAACACCA | |
| 5 | CCACAAUUUUAAAAGAAAAGGG | Probe |
| 6 | AGAAAAUUAUAGGACAGGUAAG | Probe |
| 7 | CUCGUCCACAAUUUUAAAAGAAAAGGGACGAG | Probe |
| 8 | CCUCUAGAAAAUUAUAGGACAGGUAAGAGAGG | Probe |
| 9 | GGGAGAGUUUGUAUGUCUGUUGCUAUUAUGUCU ACUAUUCUUUCCCCUGCACUGUACCCCCCAAUC CCCCCUUUUCUUUUAAAAUUGUGGAUGAAUACU GCCAUUUGUACUGCUGU | Amplicon |
| 10 | GGGAGAGUUUGUAUGUCUGUUGCUAUUAUGUCU ACUAUUCUUUCCCCUGCACUGUACCCCCCAAUC CCCCCUUUUCUUUUAAAAUUGUGGAUGAAUACU GCCAUUUGUACUGCUGUCUUAAGAUGUUCAGCC UGAUCUCUUACCUGUCCUAUAAUUUUCUUUAAU UCUUUAUUCAUAGAUUCUACUACUCCUUGACUU UGGGGAUUGUAGGGAAU | Amplicon |

SEQ ID NO:1 is a sequence of a 50-nucleotide Promoter-primer. It may be comprised of one or more deoxyribonucleotides. Nucleotides 1-27 are one strand of a T7 RNA polymerase promoter sequence, and nucleotides 27-50 are complementary to a region of SEQ ID NO:4. SEQ ID NO:2 is a sequence of a 19-nucleotide Primer. It may be comprised of one or more deoxyribonucleotides. Nucleotides 1-19 are complementary to a complementary sequence of a region of SEQ ID NO:4. SEQ ID NO:3 is a sequence of a 24-nucleotide Primer. It may be comprised of one or more deoxyribonucleotides. Nucleotides 1-24 are complementary to a complementary sequence of a region of SEQ ID NO:4. SEQ ID NO:4 is a sequence of a 1,016 nucleotide RNA in vitro transcript (IVT). Nucleotides 1-51 are from an RNA polymerase promoter sequence and a cloning vector, and nucleotides 52-1,016 are from an HIV-1 genome that includes a 3' region of the HIV-1 subtype B pol gene.

SEQ ID NO:5 is a sequence of a 22-nucleotide Probe. It may be comprised of one or more 2'-O-methyl ribonucleotides. Nucleotides 1-22 are complementary to regions of SEQ ID NOS:9 and 10. It may have an attached, detectable label. The attached detectable label may be an acridinium ester. The acridinium ester may be of a composition to include a fluoro moiety at the ortho position of the phenyl ring as disclosed in U.S. Pat. No. 5,840,873. The acridinium ester may be attached to a linker such as those derived from internucleotidyl linker intermediates such as those described in U.S. Pat. No. 5,585,481. The acridinium ester may be attached to the linker from the direction of the C9 position of the acridinium ester substantially as described in U.S. Pat. No. 5,185,439. The linker may be inserted between two nucleotides of SEQ ID NO:5. The linker may be inserted between nucleotides 10 and 11 of SEQ ID NO:5. SEQ ID NO:6 is a sequence of a 22-nucleotide Probe. It may be comprised of one or more 2'-O-methyl ribonucleotides. Nucleotides 1-22 are complementary to a region of SEQ ID NO:10. It may have an attached, detectable label. The attached detectable label may be an acridinium ester. The acridinium ester may be of a composition to include a methyl moiety at the 2 position of the acridinium ring system as disclosed in U.S. Pat. No. 5,840,873. The acridinium ester may be attached to a linker such as those derived from internucleotidyl linker intermediates such as those described in U.S. Pat. No. 5,585,481. The acridinium ester may be attached to the linker from the direction of the C9 position of the acridinium ester substantially as described in U.S. Pat. No. 5,185,439. The linker may be inserted between two nucleotides of SEQ ID NO:6. The linker may be inserted between nucleotides 8 and 9 of SEQ ID NO:6. SEQ ID NO:7 is a sequence of a 32-nucleotide Probe. It may be comprised of one or more 2'-O-methyl ribonucleotides. Nucleotides 5-27 are complementary to regions of SEQ ID NOS:9 and 10, and nucleotides 1-7 and 26-32 are complementary to each other. It may have an attached, detectable label. The attached detectable label may be an acridinium ester. The acridinium ester may be of a composition as disclosed in US Published Patent Appl. No. US 2007-0166759 A1. The acridinium ester may be attached to a linker such as those derived from internucleotidyl linker intermediates such as those described in U.S. Pat. No. 5,585,481 or from terminal linker intermediates such as 5'-Amino-Modifier C6 (part number 10-1906-90) or 3'-Amino-Modifier C7 CPG (part number 20-2958-01) from Glen Research Corporation, Sterling, Va. The acridinium ester may be attached to the linker from the direction of the N10 position of the acridinium ester substantially as described in US Published Patent Appl. No. US 2007-0166759 A1. The linker may be inserted between two nucleotides or at one of the termini of SEQ ID NO:7. The linker may be at the 5' terminus of SEQ ID NO:7. The probe may also have an attached quencher moiety that accepts the energy from the acridinium ester but does not reemit the energy as light. The quencher may attached through an internucleotidyl or terminal linker alternate to that used for the acridinium ester, through a linker on a nucleotide base or as a dedicated phosphoramidite. The quencher may be from the precursor 3'-BHQ-2 CPG (part number 20-5932-01) or 3'-Dabcyl CPG (part number 20-5912-01) from Glen Research Corporation, Sterling, Va. The quencher may be at the 3' terminus of SEQ ID NO:7. SEQ ID NO:8 is a sequence of a 32 nucleotide Probe. It may be comprised of one or more 2'-O-methyl ribonucleotides. Nucleotides 6-30 are complementary to a region of SEQ ID NO:10, and nucleotides 1-5 and 28-32 are complementary to each other. It may have an attached, detectable label. The attached detectable label may be an acridinium ester. The acridinium ester may be of a composition as disclosed in US Published Patent Appl. No. US 2007-0166759 A1. The acridinium ester may be attached to a linker such as those derived from internucleotidyl linker intermediates such as those described in U.S. Pat. No. 5,585,481 or from terminal linker intermediates such as 5'-Amino-Modifier C6 (part number 10-1906-90) or 3'-Amino-Modifier C7 CPG (part number 20-2958-01) from Glen Research Corporation, Sterling, Va. The acridinium ester may be attached to the linker from the direction of the N10 position of the acridinium ester substantially as described in US Published Patent Appl. No. US 2007-0166759 A1. The linker may be inserted between two nucleotides or at one of the termini of SEQ ID NO:8. The linker may be at the penultimate position to the 5' terminus of SEQ ID NO:8. An energy acceptor moiety capable of accepting energy from the acridinium ester and reemission of a detectable form of energy (e.g., "light"), preferably of reemission of a detectable form of energy that can be distinguished from the light emissions of the acridinium ester (e.g., light of wavelengths different from those of the acridinium ester) may be attached to the probe near the acridinium ester. The just described energy acceptor may be a fluorophore moiety. The just described energy acceptor may be at the 5' terminus of SEQ ID NO:8. The just described energy acceptor may attached through an internucleotidyl or terminal linker alternate to that used for the acridinium ester, through a linker on a nucleotide base or as a dedicated phosphoramidite. The fluorophore may be a fluorescein or tetramethylrhodamine moiety. The probe may also have an attached quencher moiety that accepts the energy from the acridinium ester and/or from the energy acceptor attached near the acridinium ester but does not reemit the energy as light. The quencher may attached through an internucleotidyl or terminal linker alternate to those used for the acridinium ester or above described energy acceptor, through a linker on a nucleotide base or as a dedicated phosphoramidite. The quencher may be from the precursor 3'-BHQ-2 CPG (part number 20-5932-01) or 3'-Dabcyl CPG (part number 20-5912-01) from Glen Research Corporation, Sterling, Va. The quencher may be at the 3' terminus of SEQ ID NO:8.

SEQ ID NO:9 is a sequence of a 116-nucleotide amplicon. It may be comprised of one or more ribonucleotides. Nucleotides 1-5 are from an RNA polymerase promoter sequence, and nucleotides 6-116 are complementary to a region of SEQ ID NO:4. Probes of SEQ ID NOS: 5 and 7 are at least partially complementary to a region of SEQ ID NO:9. SEQ ID NO:10 is a sequence of a 215-nucleotide amplicon. It may be comprised of one or more ribonucleotides. Nucleotides 1-5 are from an RNA polymerase promoter sequence, and nucleotides 6-215 are complementary to a region of SEQ ID NO:4. The sequence of nucleotides 1-116 is shared with SEQ ID NO:9. Probes of SEQ ID NOS:5 and 7 are at least partially complementary to a region of SEQ ID NO:10, and probes of SEQ ID NOS:6 and 8 are at least partially complementary to a different region of SEQ ID NO:10.

All publications and patents mentioned in the above specification are herein incorporated by reference in their entirety for all purposes whatsoever. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A nucleic acid amplification reaction mixture comprising at least two primers and at least two probes, wherein:
   (a) the at least two primers hybridize to the same strand of a target nucleic acid sequence but each primer hybridizes to a distinct nucleotide sequence on the strand, wherein each primer is present in the reaction mixture at a different amount $P_x$, where x is an integer between 1 and the number of primers in the mixture, and wherein the at least two primers comprise a first inner primer and a second outer primer;
   (b) each primer is capable of simultaneously and independently producing one of at least two amplicons from the target nucleic acid sequence under amplification conditions,
      wherein for each amplicon, a number of copies $A_x$ is capable of being produced, wherein each $A_x$ differs by at least two orders of magnitude, and
      wherein the at least two amplicons comprise a first amplicon capable of being produced from the first inner primer and a second amplicon capable of being produced from the second outer primer, wherein the first amplicon is shorter than the second amplicon;
   (c) the at least two amplicons are detectable by hybridization with the at least two probes, wherein one of the at least two probes is specific to a nucleotide sequence common to both the first and second amplicons and another of the at least two probes is specific to a nucleotide sequence contained within the second amplicon but not within the first amplicon, and each probe is detectable within a detection range $C_{x(a)}$ to $C_{x(b)}$,
      wherein $C_{x(a)}$ is the minimum detectable number of copies of amplicon and $C_{x(b)}$ is the maximum detectable number of copies of amplicon for probe x,
      wherein for each probe, $C_{x+1(a)}$ is greater than $C_{x(a)}$ and $C_{x+1(b)}$ is greater than $C_{x(b)}$ such that the at least two probes together are detectable across a dynamic range of from about $10^3$ to $10^7$, wherein for each amplicon-probe combination, $A_x$ is between $C_{x(a)}$ and $C_{x(b)}$, and wherein the at least two probes are capable of producing distinguishable detection signals.

2. The reaction mixture of claim 1, wherein the reaction mixture further comprises a promoter-primer which operates in a direction opposite the first inner and second outer primers.

3. The reaction mixture of claim 1, wherein the number of copies of each amplicon $A_x$ differs by at least three orders of magnitude.

4. The reaction mixture of claim 1, wherein the number of copies of each amplicon $A_x$ differs by at least four orders of magnitude.

5. The reaction mixture of claim 1, wherein the amount of each primer differs by at least two orders of magnitude.

6. The reaction mixture of claim 1, wherein the at least two probes are acridinium ester probes.

7. The reaction mixture of claim 1, wherein the at least two probes are HICS probes.

8. The reaction mixture of claim 1, wherein the dynamic range is from about $10^4$ to $10^6$.

* * * * *